United States Patent [19]
Foster et al.

[11] Patent Number: 5,846,514
[45] Date of Patent: Dec. 8, 1998

[54] ENHANCEMENT OF THE EFFICACY OF NIFEDIPINE BY DEUTERATION

[75] Inventors: Robert T. Foster; Richard Lewanczuk, both of Edmonton; Gilles Caille, Outremont, all of Canada

[73] Assignee: Isotechnika, Inc., Edmonton, Canada

[21] Appl. No.: 725,992

[22] Filed: Oct. 4, 1996

Related U.S. Application Data

[63] Continuation-in-part of Ser. No. 401,530, Mar. 27, 1995, abandoned, which is a continuation-in-part of Ser. No. 217,897, Mar. 25, 1994, abandoned.

[51] Int. Cl.⁶ .................................................. A61K 51/04
[52] U.S. Cl. ......................................................... 424/1.81
[58] Field of Search .......................... 424/1.81; 514/356, 514/458; 546/167, 256, 263, 321

[56] References Cited

U.S. PATENT DOCUMENTS

| | | | |
|---|---|---|---|
| 3,314,827 | 4/1967 | de Vries | 148/13.1 |
| 4,304,782 | 12/1981 | Dumont et al. | |
| 4,412,986 | 11/1983 | Kawata et al. | 424/80 |
| 4,636,509 | 1/1987 | Phillipps et al. | |
| 4,675,338 | 6/1987 | Bommer et al. | |
| 4,874,780 | 10/1989 | Borretzen et al. | |
| 4,898,855 | 2/1990 | Baggiolini et al. | |
| 5,012,052 | 4/1991 | Hayes | 250/288 |
| 5,049,396 | 9/1991 | Oftebro et al. | |
| 5,122,511 | 6/1992 | Patchette et al. | |
| 5,130,145 | 7/1992 | Oftebro et al. | |
| 5,149,820 | 9/1992 | Borretzen et al. | |
| 5,149,846 | 9/1992 | Baggiolini et al. | |
| 5,169,773 | 12/1992 | Rosenthaler et al. | |
| 5,227,467 | 7/1993 | Durette et al. | |
| 5,247,123 | 9/1993 | Baggiolini et al. | |
| 5,314,827 | 5/1994 | Schmidt | 436/106 |
| 5,318,901 | 6/1994 | Patchett et al. | |
| 5,376,540 | 12/1994 | Kyle | 435/134 |
| 5,424,539 | 6/1995 | Brand et al. | 250/288 |
| 5,432,058 | 7/1995 | Lange et al. | 435/11 |
| 5,525,590 | 6/1996 | Bollinger et al. | |
| 5,604,254 | 2/1997 | Quadro | |

FOREIGN PATENT DOCUMENTS

| | | |
|---|---|---|
| 2673291 | 8/1992 | France . |
| 89/09486 | 10/1989 | WIPO . |

OTHER PUBLICATIONS

Rampe, D., et al., "Deuterated analogs of verapamil and nifedipine", European Journal of Medicinal Chemistry (1993), vol. 28, pp. 259–263.

Chemical Abstracts Tenth Collective Index, 1982, p. 46167cs.

Chemical Abstracts Eleventh Collective Index, 1987, pp. 58923cs.

Chemical Abstracts Twelfth Collective Index, 1992, p. 79669cs.

Stone–Elander, S., et al., "Synthesis of [isopropyl–11C] nimodipinefor in vivo studies of dihydropyridine binding in man using positron emission tomography", International Journal of Radiation Applications and Instrumentation Part A: Applied Radiation and isotopes (1991), vol. 42, pp. 871–875.

Funaki et al., "In Vivo Oxidative Cleavage of a Pyridine–Carboxylic Acid Ester Metabolitic of Nifedipine," Biochemical Pharmacolgy, vol. 38, No. 23, pp. 4213–4216, 1989.

*Primary Examiner*—Gary E. Hollinden
*Assistant Examiner*—Michael G. Hartley
*Attorney, Agent, or Firm*—Beveridge, deGrandi, Weilacher & Young, LLP

[57] ABSTRACT

A method of enhancing the efficiency and increasing the duration of action of drugs (e.g. dihydropyridines and antibacterials) and particularly of nifedipine and penicillins wherein one or more hydrogen atoms are deuterated and wherein the deuterated drug has unexpectedly improved properties when used in much lower concentrations than unmodified drug. A method for determining the identity and bioequivalency of a new drug is also disclosed wherein the molecular and isotope structure of a new drug is determined by isotope ratio mass spectrometry and compared with the molecular and isotope structure of a known human drug.

10 Claims, 41 Drawing Sheets

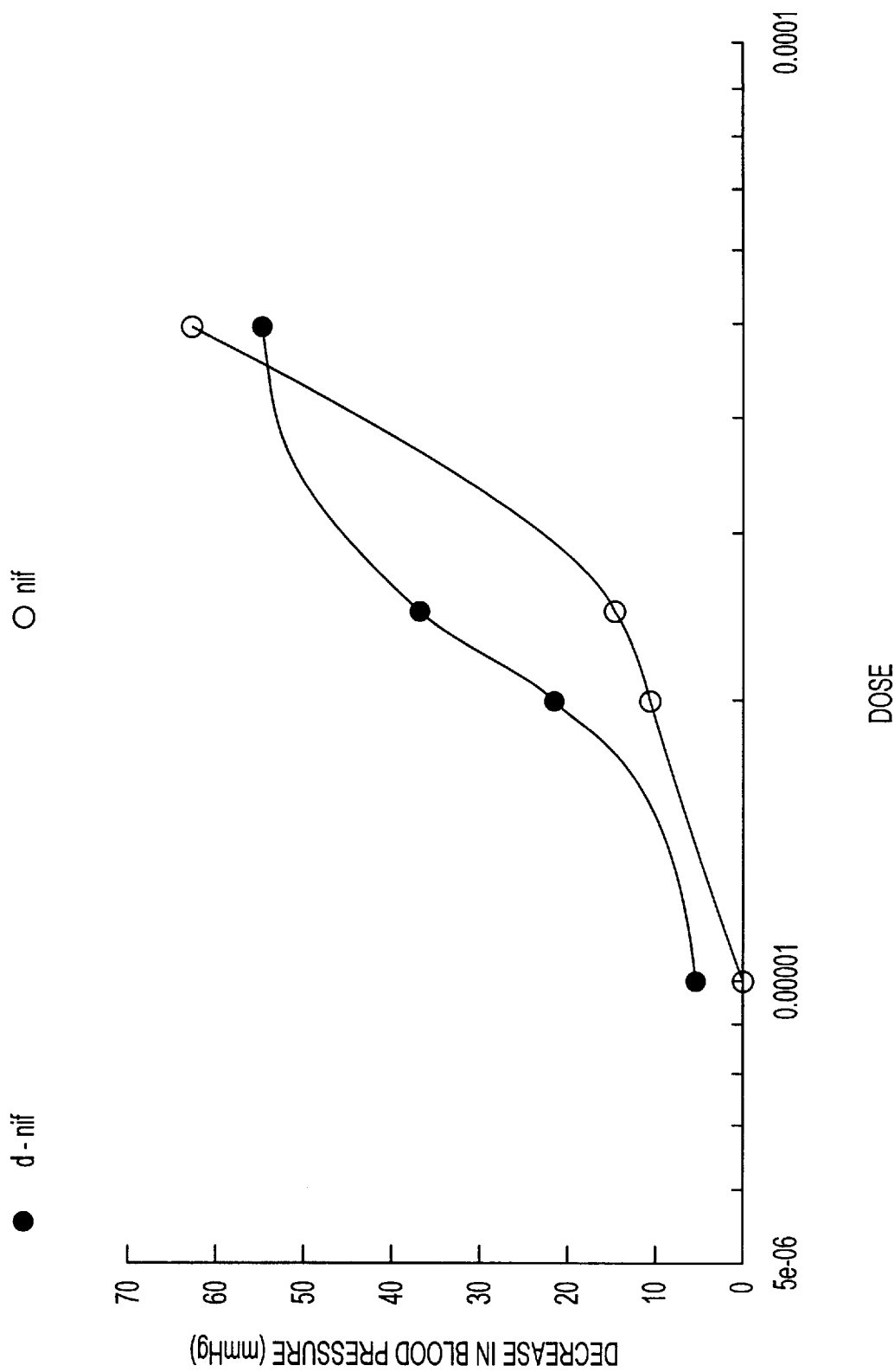

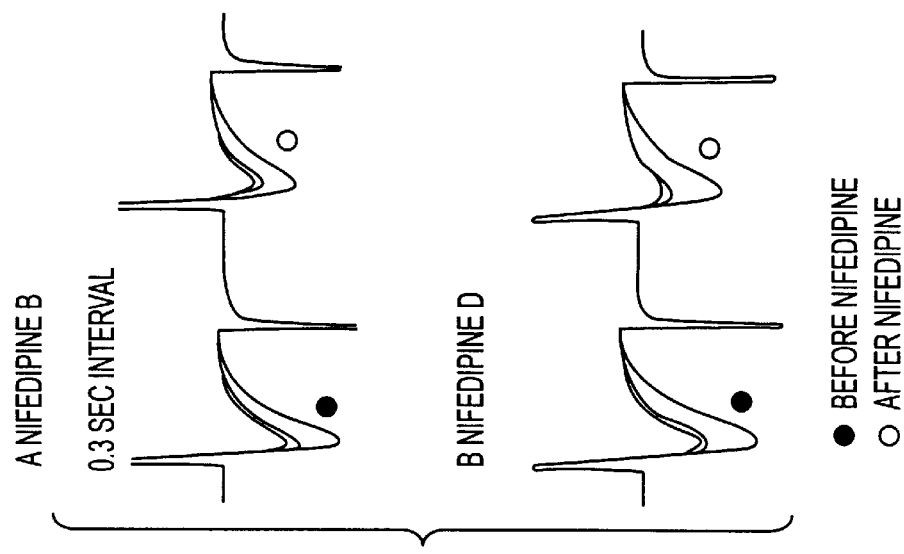
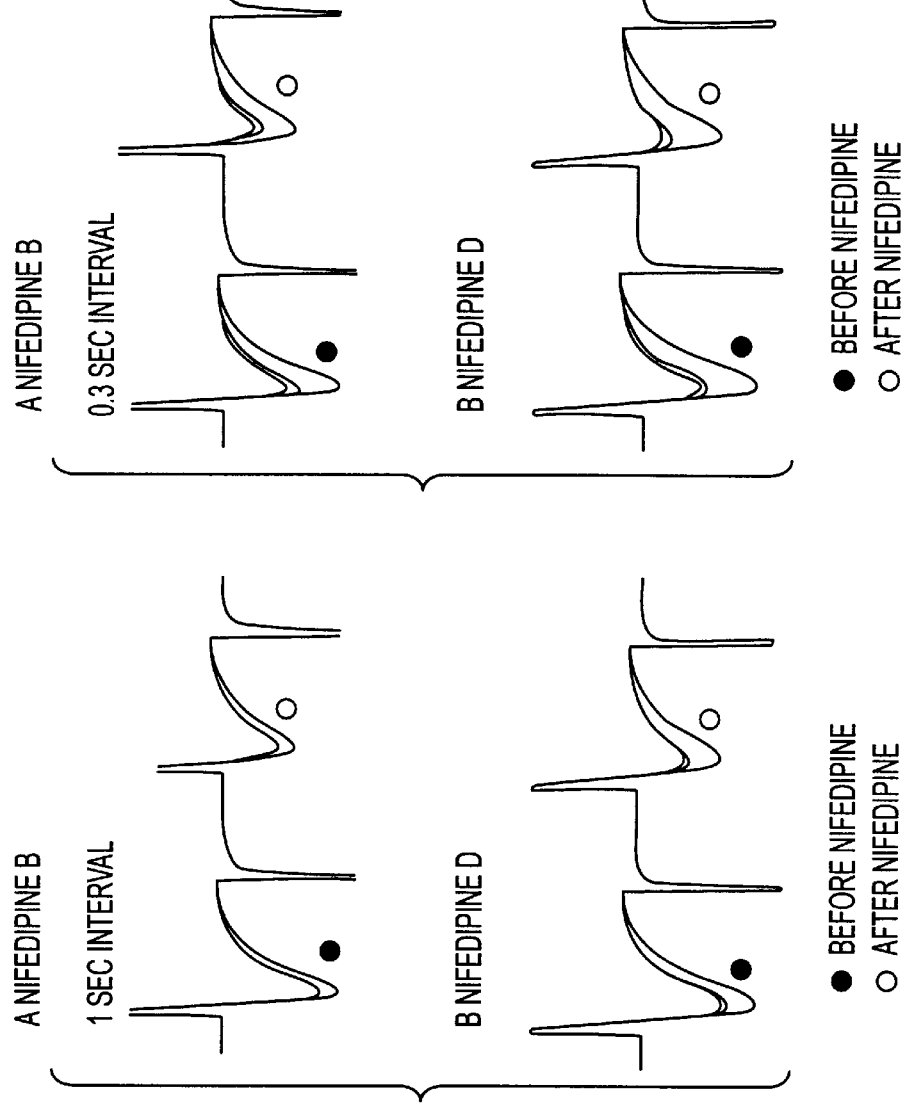
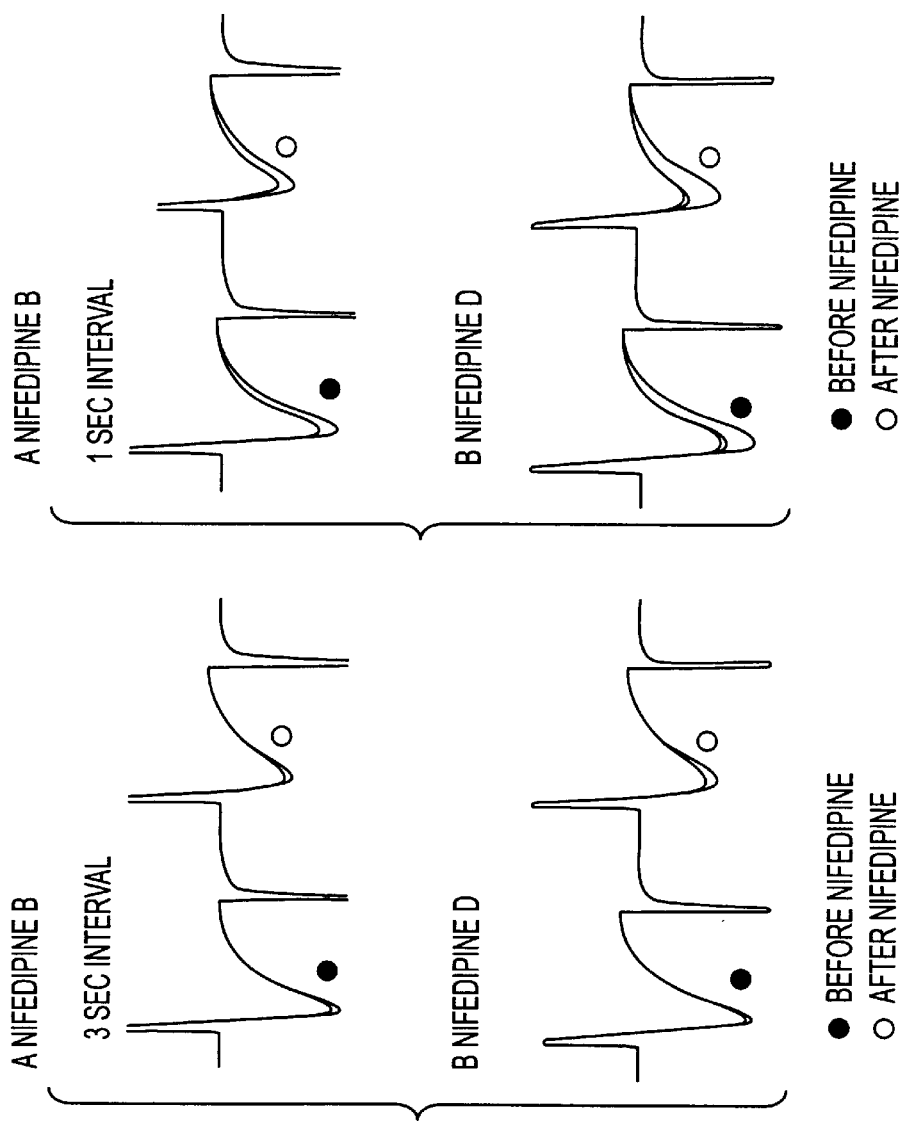

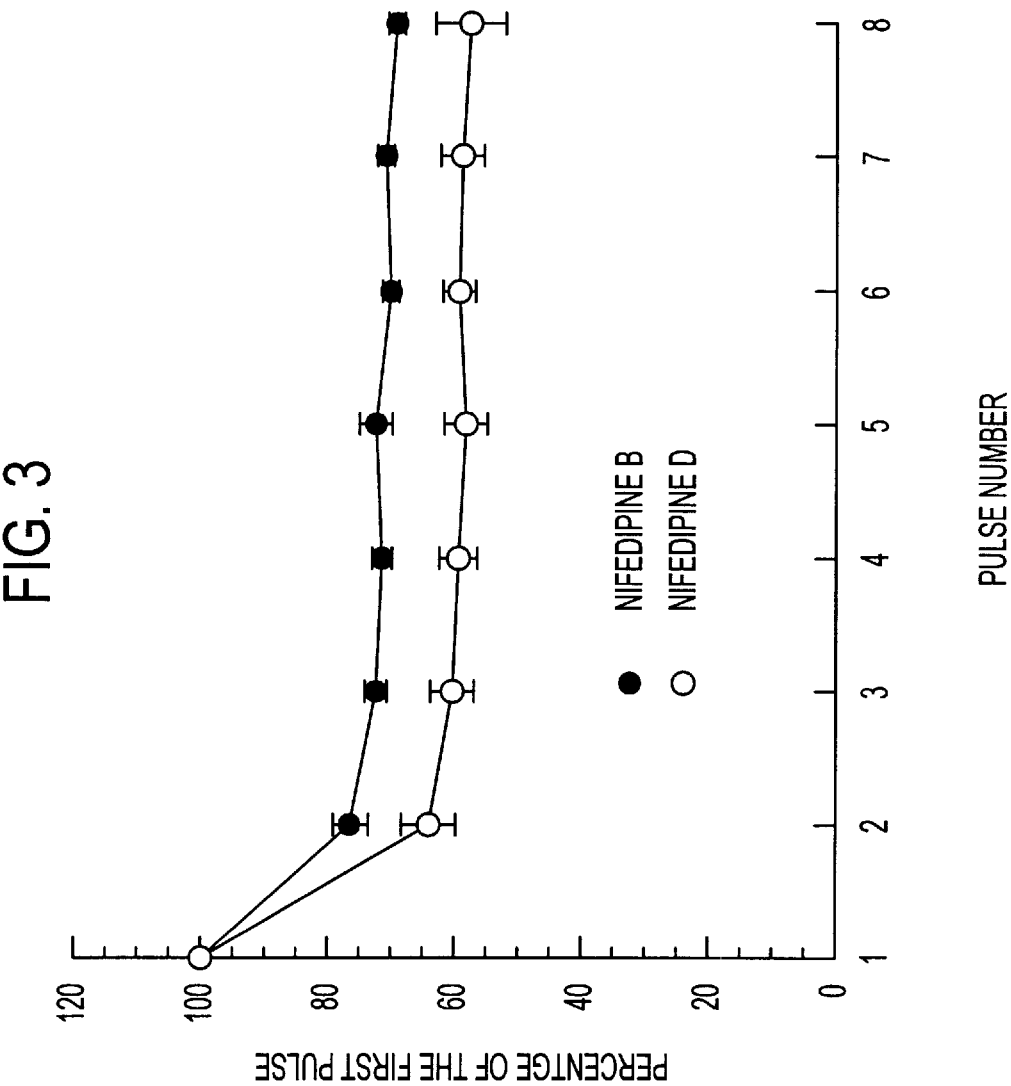

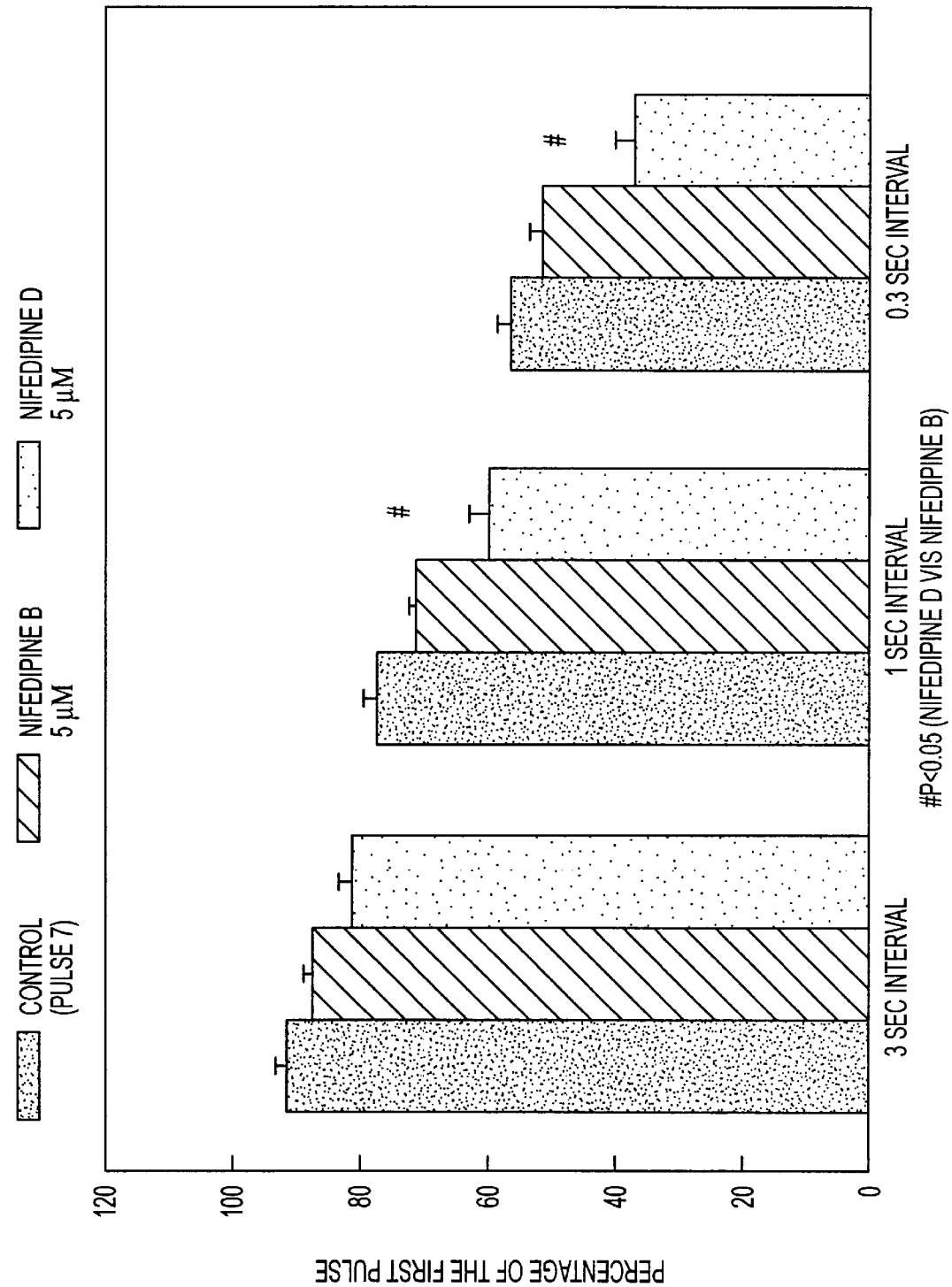

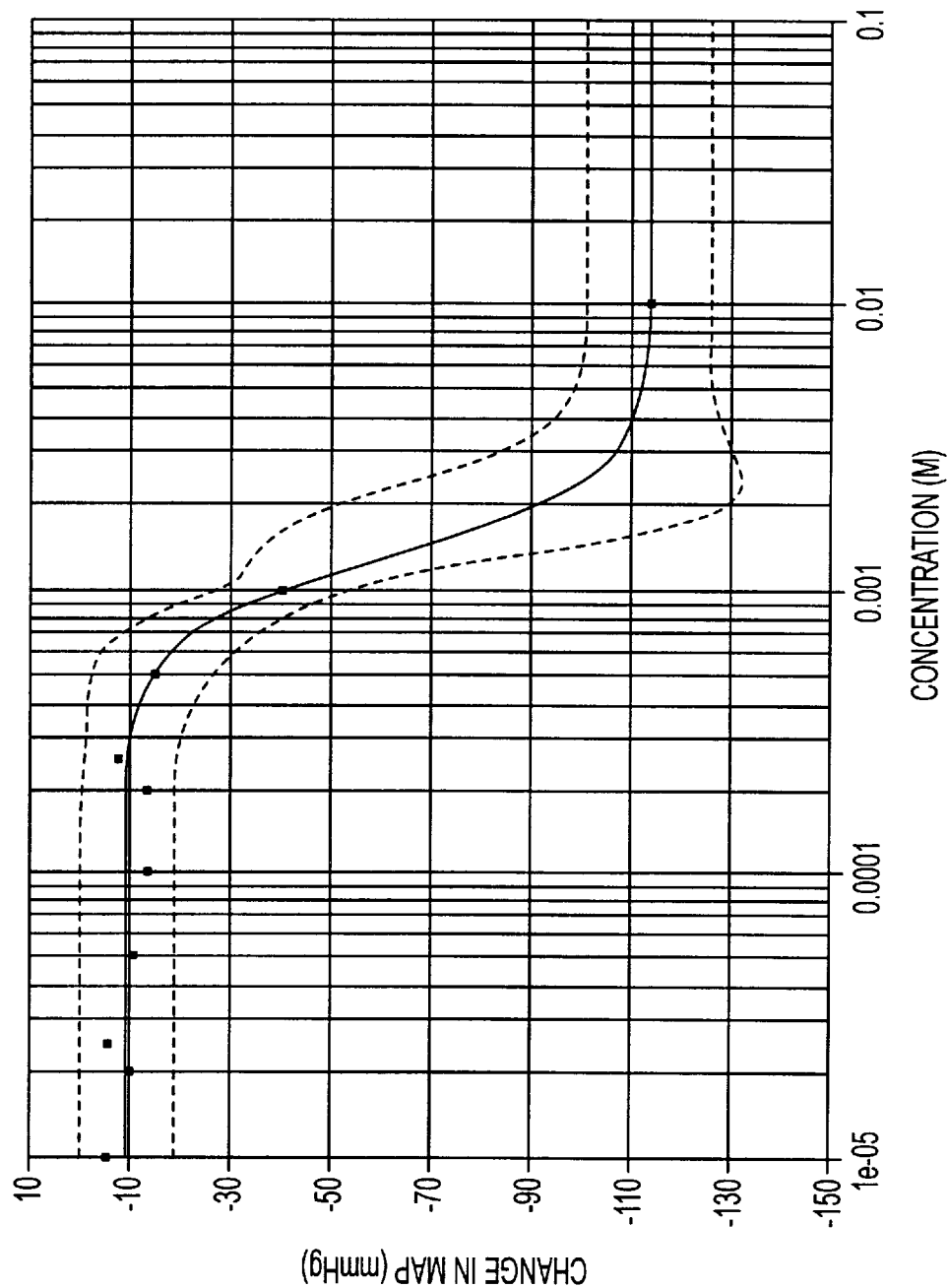

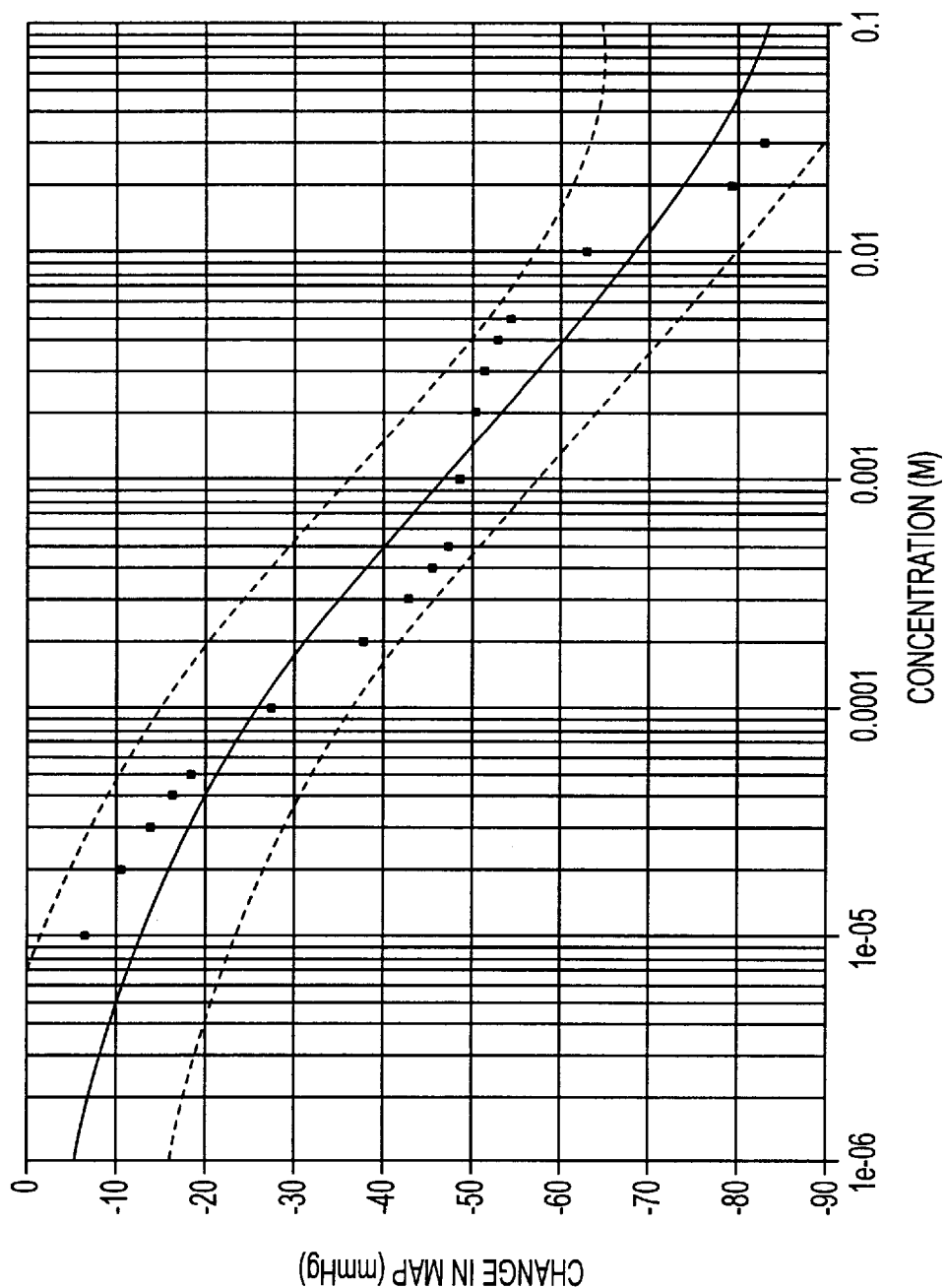

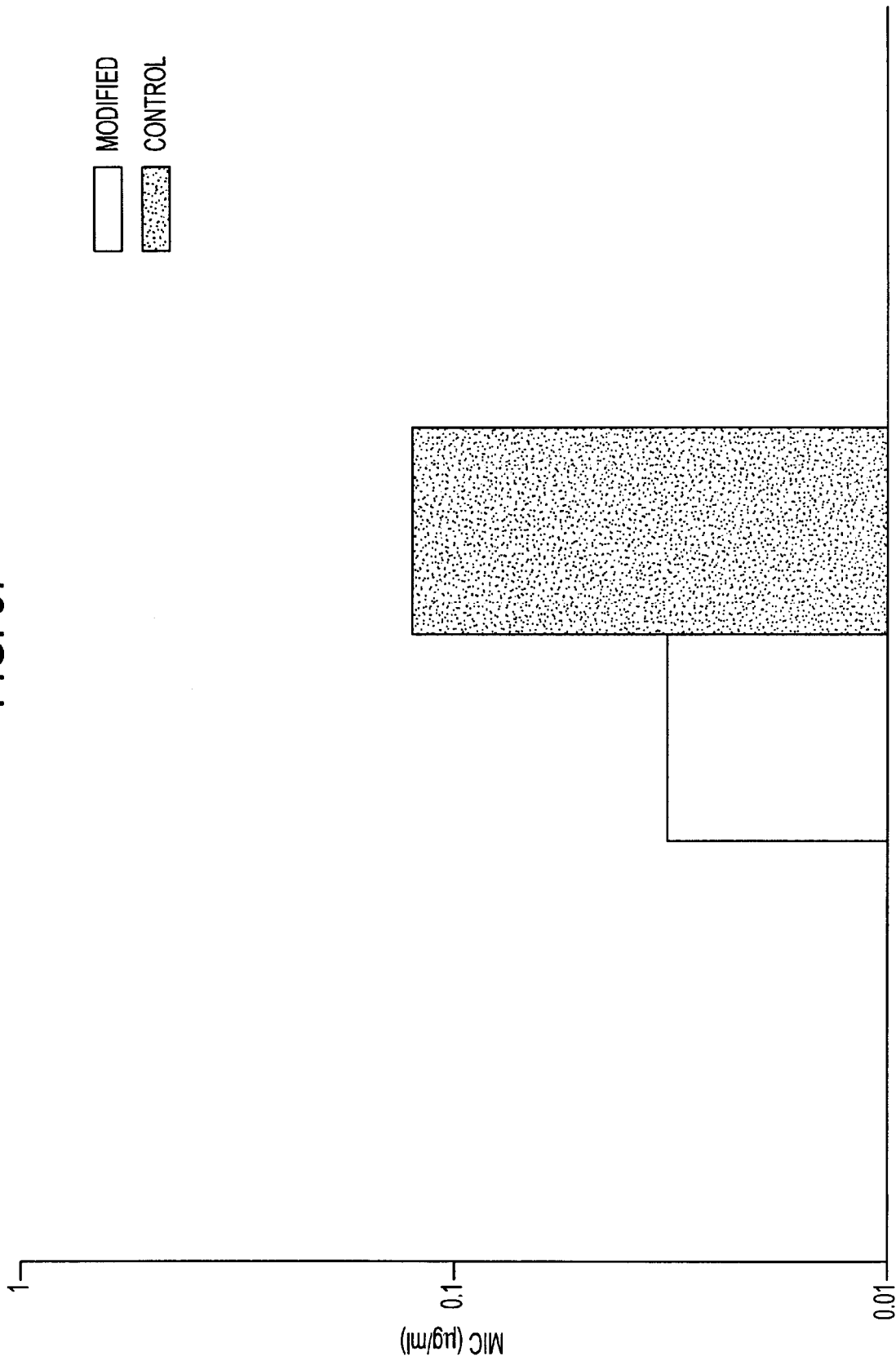

ENHANCEMENT OF THE EFFICACY OF NIFEDIPINE BY DEUTERATION

REFERENCE TO A RELATED APPLICATION

This is a continuation-in-part of our U.S. patent application Ser. No. 08/410,530 filed Mar. 27, 1995, now abandoned, which in turn is a continuation-in-part of our U.S. patent application Ser. No. 08/217,897 filed Mar. 25, 1994, now abandoned, which are both relied on and incorporated herein by reference in its entirety.

BACKGROUND OF THE INVENTION

The present invention relates to a process for enhancing the efficacy of known pharmaceuticals or drugs, and to the enhanced drugs so produced, by changing the isotopic form of the molecular structure of the known drug. More particularly, the present invention relates to the modification of the molecular structure of known drugs containing one or more hydrogen atoms by deuterating one or more of the hydrogen atoms to deuterium atoms. The resulting drug is significantly altered and has greatly improved activity over the known drug. Most particularly this invention relates to a method of deuterating a selected pharmaceutical compound such as a member of the dihydropyridine family (e.g., nifedipine), ceftazidime, members of the penicillin family, and the like whereby the deuterated product has an increased effect and an increased duration of action on mammals at lower concentration than does the original substance. The present invention has particular application to enhancing the effectiveness of antibacterial drugs.

When pharmaceuticals are synthesized, a carbon backbone is assembled having various substituents including carbon, hydrogen, oxygen, nitrogen, etc. Pharmaceuticals have been designed and synthesized by a number of modes including, for example, serendipity and molecular modification. These and other methods have generated a vast number of drugs over the course of time. As such modifications have allowed individual companies to keep a competitive edge in the marketplace, a significant part of the industry's time and resources is spent searching for novel agents within certain pharmacologic classifications, e.g., antihypertensives, anti-bacterials. Such novel agents often have different activities from the prototype compounds, thus justifying the monies spent for their development.

SUMMARY OF THE INVENTION

It is known that virtually all drugs now marketed include a number of hydrogen atoms, each of which has a molecular mass of one. It has now been found that when one or more of the hydrogen atoms on a drug are modified so that their molecular mass becomes two, the activity of the drug is significantly altered and is even greatly improved. Thus, for example, isotopic modification of a dihydropyridine, e.g., such as nifedipine, has resulted in an unexpected change in the hypotensive (blood pressure lowering) effect in mammals compared to nifedipine per se, and such effects should also be achieved with humans.

Accordingly, in one aspect of the invention there is provided pharmaceutical preparations containing at least one pharmacologically active ingredient which is a compound wherein at least one of the hydrogen atoms thereof is replaced with a deuterium atom, or wherein at least one carbon, nitrogen or oxygen atom is replaced by a different isotope thereof.

In another aspect, the present invention provides a method for making the deuterated dihydropyridine comprising: dissolving a dihydropyridine in a mixture of deuterochloroform and deuterium oxide to form a solution, adding trifluoroacetic anhydride and deuteroacetone to said solution, freezing and sealing said solution within a vessel, heating said solution at a temperature and for a period of time sufficient to deuterate all of the hydrogen atoms at the 2 and 6 position on said dihydropyridine, and recovering said deuterized dihydropyridine.

Still another aspect of the present invention provides a method of detecting whether a pharmaceutical compound is identical and/or bioequivalent to a known pharmaceutical compound comprising the steps of
(a) determining the molecular and isotopic structure of said known pharmaceutical compound by gas chromatography-isotope ratio mass spectrometry,
(b) determining the molecular and isotopic structure of said pharmaceutical compound subject to said detection by gas chromatography-isotope ratio mass spectrometry,
(c) comparing the results of said tow determinations to detect any isotope variation in the molecular structure of said pharmaceutical compound over that of the known pharmaceutical compound.

Nifedipine is marketed worldwide as an important drug used in the treatment of angina and hypertension. Its structure is as follows:

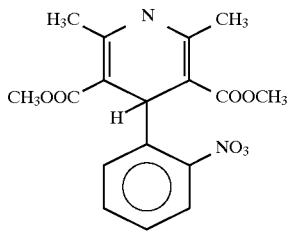

A feature of the present invention is the modification of nifedipine by replacing one or more hydrogens of the methyl groups with deuterium or by replacing one or more of the methyl groups with $CD_3$. In this way the therapeutic properties of nifedipine can be altered and can even be significantly improved. For example, by modifying the nifedipine by replacing the two methyl groups at the 2 and 6 positions on the ring with two deuterated groups ($CD_3$), i.e., replacing 6 hydrogen atoms with six deuterium atoms, the structure of the deuterated nifedipine is as follows:

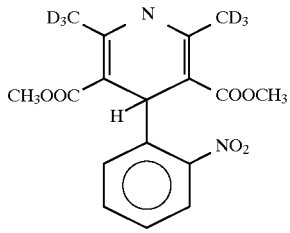

Both of the above molecules are nifedipine and the latter structure is an isotopic form of the former.

In the same way, the modification of the antibacterial, ceftazidine, by deuteration will produce modified ceftazidine having altered properties compared to the unmodified product.

Penicillin and other antibiotics of the beta lactam structure can be modified in accordance with the invention and the deuterated product exhibits enhanced activities with respect to selected bacterial strains.

BRIEF DESCRIPTION OF THE DRAWINGS

The present invention will be further understood with reference to the drawings, wherein:

FIG. 1 shows the hypotensive effect of the various concentrations of the deuterated nifedipines on the treated rats as compared with nifedipine per se;

FIGS. 2 and 3 show use dependent inhibition of control nifedipine (Nifedipine B) and deuterated nifedipine (Nifedipine D) on T type calcium channels;

FIG. 4 shows the effect of control nifedipine and deuterated nifedipine on calcium current inhibition as a function of pulse frequency;

FIGS. 9a and 9b show the dose-response effect for the control and deuterated (test) nicardipines;

FIG. 37 shows the results of a ceftazidime tube dilution experiment.

DETAILED DESCRIPTION OF THE INVENTION

Figure 5:
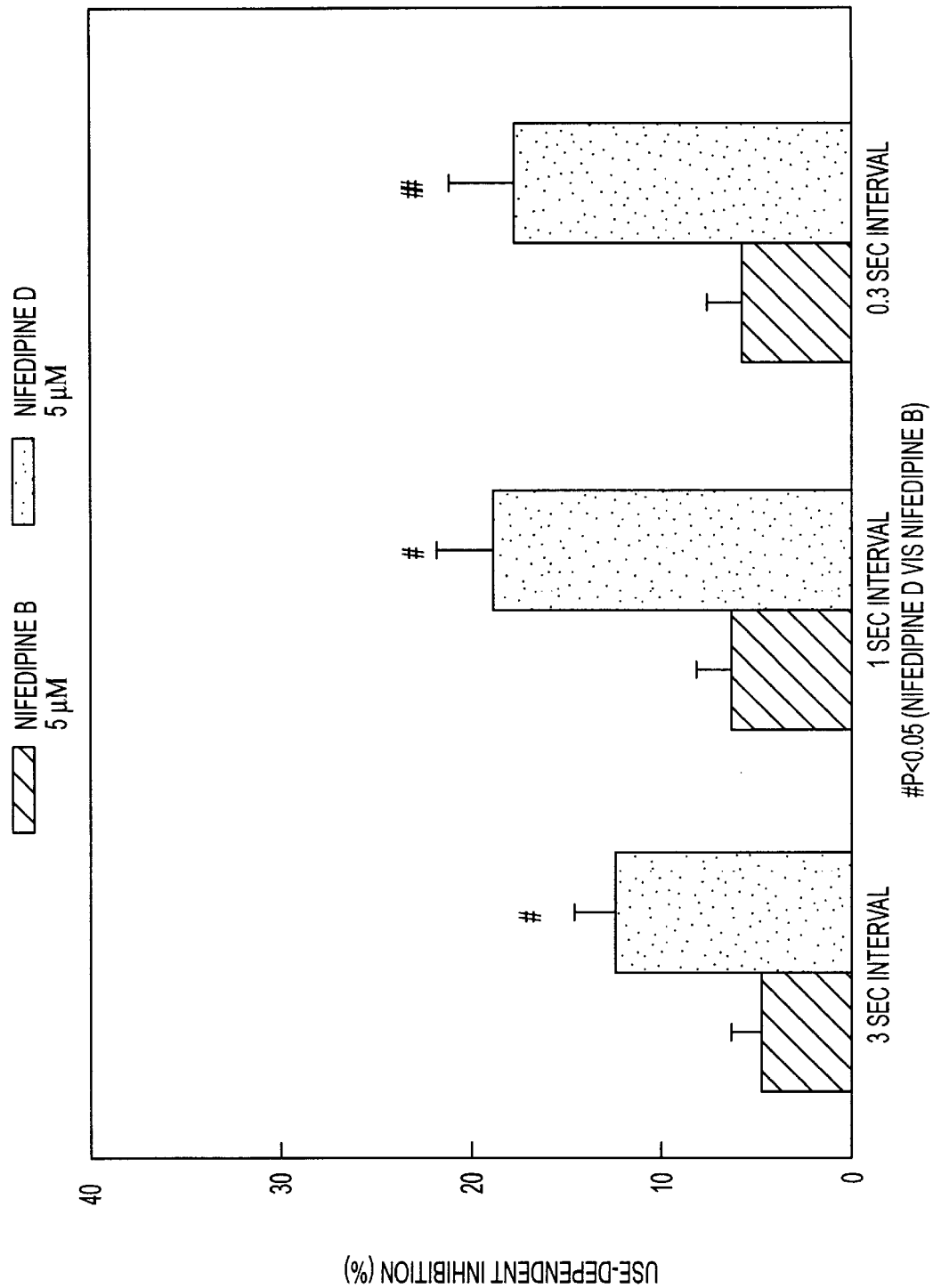
FIG. 5 shows the effect of control nifedipine and deuterated nifedipine on use dependency.

In carrying out one of the aspects of the present invention, modification of nifedipine (and other dihydropyridines such as, for example, nicardipine, nimodipine, nivuldipine, nisoldipine, nitrendipine, felodipine, isradipine and amlodipine) can be achieved by dissolving the nifedipine in a deuteration tube in a mixture of deuterochloroform and deuterium oxide, and then adding a minor amount of trifluoroacetic anhydride and deuteroacetone thereto and mixing therewith. The solution is then frozen within the tube, preferably by immersing the tube in liquid nitrogen and then sealing the tube. The sealed tube is then heated at a temperature with the range of from about 50° C. to about 65° C., and preferably within the range of about 55° to about 60° C. and maintained at that temperature for a period of time sufficient to deuterate the methyl group at the 2 and 6 positions on the nifedipine to $CD_3$. A time of from about 150 to about 180 hours is effective to complete the reaction, with a time of about 160 to 170 hours being preferred.

To illustrate, deuterated nifedipine was synthesized in the following manner:

EXAMPLE I 80 mg of nifedipine in powder form was placed into a special deuteration tube and dissolved therein in a mixture of 2 ml of deuterochloroform and 0.5 ml of deuterium oxide after which 0.2 ml of trifluoroacetic anhydride and 2 ml of deuteroacetone were added and mixed therewith. The solution was frozen in liquid nitrogen and the tube flame sealed under nitrogen. The tube was then heated at 57° C. for 168 hours after which it was cooled and opened. The contents of the tube were transferred to a round-bottom flask and the solvent was removed in vacuo on a rotovap. All operations were conducted under reduced intensity of light. Using conventional $^1H$ nuclear magnetic resonance (NMR) the deuterium substitution was calculated to be 95% of the C-2 and C-6 methyl groups shown above.

The effect of the deuterated nifedipine on the blood pressure in rats was then determined as follows:

EXAMPLE II

Spontaneously hypertensive rats (SHR) were anesthetized with pentobarbital (65 mg/kg, intraperitoneally) and a carotid artery and jugular vein cannulated. Blood pressure was continuously monitored via the carotid artery cannula. Nifedipine samples, both deuterated and non-deuterated, dissolved in dimethylsulfoxide (DMSO) were diluted in saline so that the final injected concentration of DMSO was less than 0.025% by volume. Aliquots of appropriate dilutions were then injected intravenously in the SHR and blood pressure effects monitored for at least two hours following injection. Doses used were 0.00001, 0.00002, 0.000025, and 0.00005 moles per rat in the control group and in the test group. All rats were within 25 grams of body weight of each other.

The results are shown in FIG. 1. At the three lower concentrations the hypotensive effect of deuterated nifedipine was greater than that of regular nifedipine (p=0.08 by Wilcoxon rank-sum test). Effective doses of 50% of the rats ($ED_{50}$'s) were calculated on the basis of the results from the above doses and results were: (1) Log $ED_{50}$ deuterated nifedipine: −4.48 (−4.53 to −4.43, 95% confidence interval); and (2) Log $ED_{50}$ regular nifedipine: −4.36 (−4.40 to −4.31, 95% confidence interval). As the confidence intervals do not overlap, there is a statistical difference in the potency of the two nifedipine products, with the deuterated nifedipine unexpectedly having the greatest potency.

The effect of deuterated nifedipine on calcium channel blocking activity was studied and the studies were carried out using the whole cell version of the patch clamp method, as follows:

EXAMPLE III

NIE-115 cells (neuroblastoma cell line) were used and these cells were cultured using conventional tissue culture techniques. For study, cells were used six to eight hours after trypsinization and replating. In this state the predominant calcium channel expressed was the T-type channel, which was used for the current studies.

Patch clamping was carried out using the following external and internal solutions: External solution (in mM): $BaCl_2$ 20, Tris 105, KCl 5, CsCl 5, HEPES 20, glucose 20 and tetrodotoxin 0.0005. Internal solutions (in mM): CsCl 130, ATP $Na_2$ 2, HEPES 20, glucose 5, $MgCl_2$ 5, cAMP 0.25, and EGTA 10. Osmolarity of all solutions was adjusted to 310–320 mOsm and the pH adjusted to 7.4 using HCl, NaOH, CsOH or $Ba(OH)_2$ as required. The Petri dish containing the cells was mounted on the stage of an inverted phase contrast microscope. Pipettes fabricated from thin-walled borosilicate glass, and containing the internal solution, were advanced to the selected cell surface using a micromanipulator. Suction facilitated the formation of a membrane patch with resistance in the range of 20–30 gigaohms. Test pulses in increments of 10 mV were applied for 200 msec with at least 5 sec allowed for channel recovery between pulses. Basal channel activity was measured based on the peak inward currents. After addition of the nifedipine solutions to the appropriate concentration, 3 minutes were allowed for the drug to reach equilibrium concentrations. After this time current voltage relationships were re-tested and the results expressed as the percentage of control current obtained (i.e., 100% indicates no channel blocking activity).

Preliminary results at concentrations of $1 \times 10^{-6}$ and $1 \times 10^{-5}$ showed no statistical difference between channel conductance for deuterated and non-deuterated nifedipine (70% vs. 77%, and 35% and 43%, respectively, p-not significant). During these studies, however, it was noted that a difference did exist between the channel activation dependency of the two nifedipine compounds. As usual, normal nifedipine showed blocking activity which is dependent on the state of activation of the channels (normally blocking is facilitated when channels are more "active"). This effect was not seen for deuterated nifedipine; rather, it seemed to show continual maximal effect regardless of channel status. This suggests that the binding of deuterated nifedipine to the calcium channel is enhanced even though there may be no difference in potency. Clinically, this means that deuterated nifedipine may have a longer half-life of the receptor and/or that it may have a constant effect across blood pressure ranges (normally the higher the blood pressure, the greater the hypotensive effect of calcium channel blockers). It is expected that the deuterated nifedipine would act in a similar manner in humans having high blood pressure.

While it has been noted that deuterizing one or more hydrogen atoms in known pharmaceutical compounds will enhance or alter the activity of such compounds, it is believed that the activity of such compounds may also be altered by substituting a different isotope for one or more of the other atoms in the compound. It is known that several varieties of other atoms, such as carbon, nitrogen, oxygen, tin, etc., exist which differ in their atomic mass. These differing species of atoms are referred to as isotopes and differ only in the number of neutrons in the nucleus.

EXAMPLE IV

Use dependency of calcium channel inhibition-repetitive activation of calcium channels progressively reduces the peak inward current. Such a decrease in current occurs more markedly the greater the frequency of stimulation of the channels. In the presence of a "use dependent" antagonist, the decrease in current with repetitive stimulation is enhanced. Use dependency implies that the antagonist binds cumulatively in small increments during subsequent channel activations. After 2 or 3 channel activations in the case of calcium channels, a steady state of inhibition is reached. The underlying implication of use dependence is that a given antagonist (drug) binds more strongly to the active channel. A drug which shows greater use dependent channel inhibition is presumed to have a greater affinity for the active calcium channel.

In the following set of examples, calcium channels were depolarized with repetitive pulses of current at the intervals indicated. Such studies were carried out using the whole cell version of the patch-clamp. The reduction of inward current as a function of the interval between pulses in the absence of any drug was taken as the control. Control (i.e., non-deuterated) and deuterated nifedipine were then applied to the cells at a concentration of 5 micromolar. The decrease in inward current as a function of frequency of stimulation (i.e., use dependence) was then compared between the two nifedipine preparations.

FIG. 2 shows use dependent inhibition of control nifedipine (Nifedipine B) and deuterated nifedipine (Nifedipine D) on T type calcium channels in N1E 115 cells. This figure represents inward current flow and its inhibition by the nifedipines. As frequency of stimulation increases, inward current upon repetitive stimulation decreases (use dependence). Nifedipine is seen to decrease inward current, but at increased stimulation frequency deuterated nifedipine is more effective than control nifedipine (panel C). These differences are further shown in FIGS. 3–5.

FIG. 3 represents the inhibitory effect of the two nifedipines on inward calcium current for repetitive 1 second pulses (depolarizations). At this pulse frequency deuterated nifedipine is more effective at blocking calcium current than control current (p<0.05 by repeated measures ANOVA). Concentrations of nifedipine were 5 micromolar in both cases.

FIG. 4 shows the effect of the two nifedipines on calcium current inhibition as a function of pulse frequency. At 1 and 0.3 second intervals deuterated nifedipine was more effective than control nifedipine in blocking the calcium channels.

FIG. 5 shows the effect of the two nifedipines on use dependency. At all frequencies deuterated nifedipine showed greater use dependent calcium channel inhibition. Such inhibition was even more marked as frequency of stimulation increased.

Based on the above data, deuterated nifedipine is seen to have greater use dependent inhibition of calcium channels. This means that deuterated nifedipine is more effective than regular nifedipine at blocking the calcium channels as the frequency of stimulation increases. Because channel activation is greater in pathological conditions such as hypertension or angina, deuterated nifedipine would be expected to be more efficacious/potent in these disorders than regular nifedipine. In non-pathological conditions where channel activation is not as great, however, the activity of deuterated nifedipine would approach that of regular nifedipine. Such a characteristic is extremely appealing as it means that the relative potency of the drug (e.g., deuterated nifedipine) would vary directly with the severity of the condition. Thus, for example, the drug would seemingly "know" how much to reduce the blood pressure in order to achieve a particular blood pressure goal. Currently, as the severity of a condition (e.g., hypertension, angina) increases, the dose of nifedipine necessary to treat such a condition also increases. Such may not be the case for deuterated nifedipine.

EXAMPLE V

Effect of deuterated and control nifedipines on blood pressure in normotensive Sprague-Dawley rats. Control and deuterated nifedipines were dissolved in minimal volumes of ethanol and diluted until the final concentration of ethanol was less than 0.04%. One milliliter doses of the two nifedipines at the indicated concentrations were then injected into pentobarbital-anesthetized Sprague-Dawley rats weighing between 300 and 350 grams. The maximum change in mean arterial pressure, as well as the duration of hypotensive response, were measured directly by means of an intra-arterial catheter. Only one drug dose was given to each rat and a minimum of 60 minutes was allowed for blood pressure to return to baseline. Results are shown in the figures discussed below. At each time period the duration of effect was greater for deuterated nifedipine compared to control nifedipine. However, because the duration of response might be dependent on the magnitude of decrease in blood pressure, equipotent doses of the two formulations were compared. In this comparison, control nifedipine at a concentration of $2 \times 10^{-3}$ molar and deuterated nifedipine at a concentration of $1 \times 10^{-3}$ molar were compared (relative potencies −45.8 vs. −40.3 mmHg control vs. deuterated, p=NS). At these doses, despite an equivalent blood pressure effect, the duration of action of control nifedipine was 46.5 min and the duration of action of deuterated nifedipine was 62.2 min (p=0.02). Thus, the duration of action of deuterated nifedipine is greater than that of control nifedipine independent of blood pressure lowering effectiveness (i.e., both potency and duration of action differ).

Figure 6A:
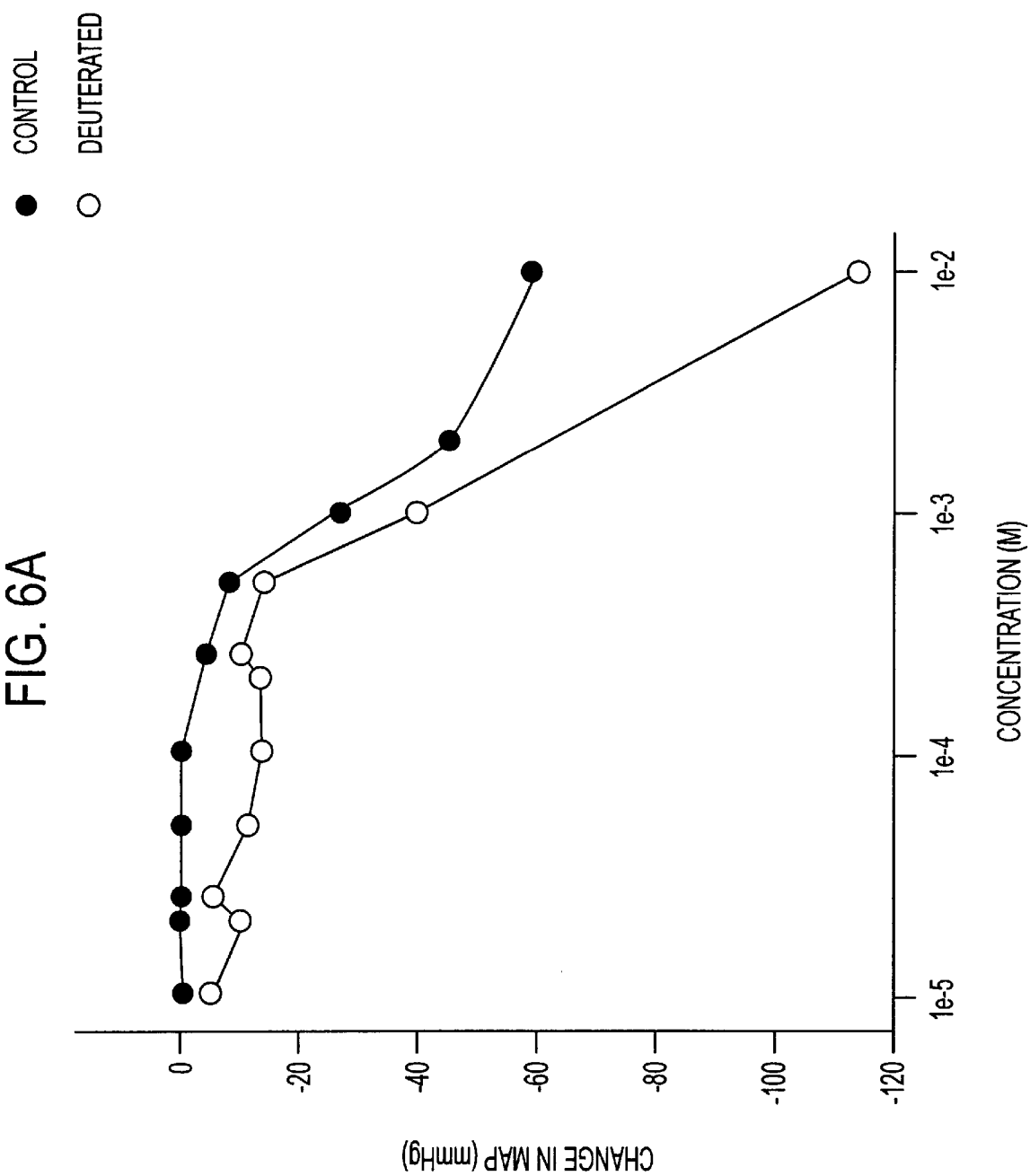
FIGS. 6(a) and (b) show the effect of control and deuterated nifedipine on mean arterial pressure.
Figure 6B:
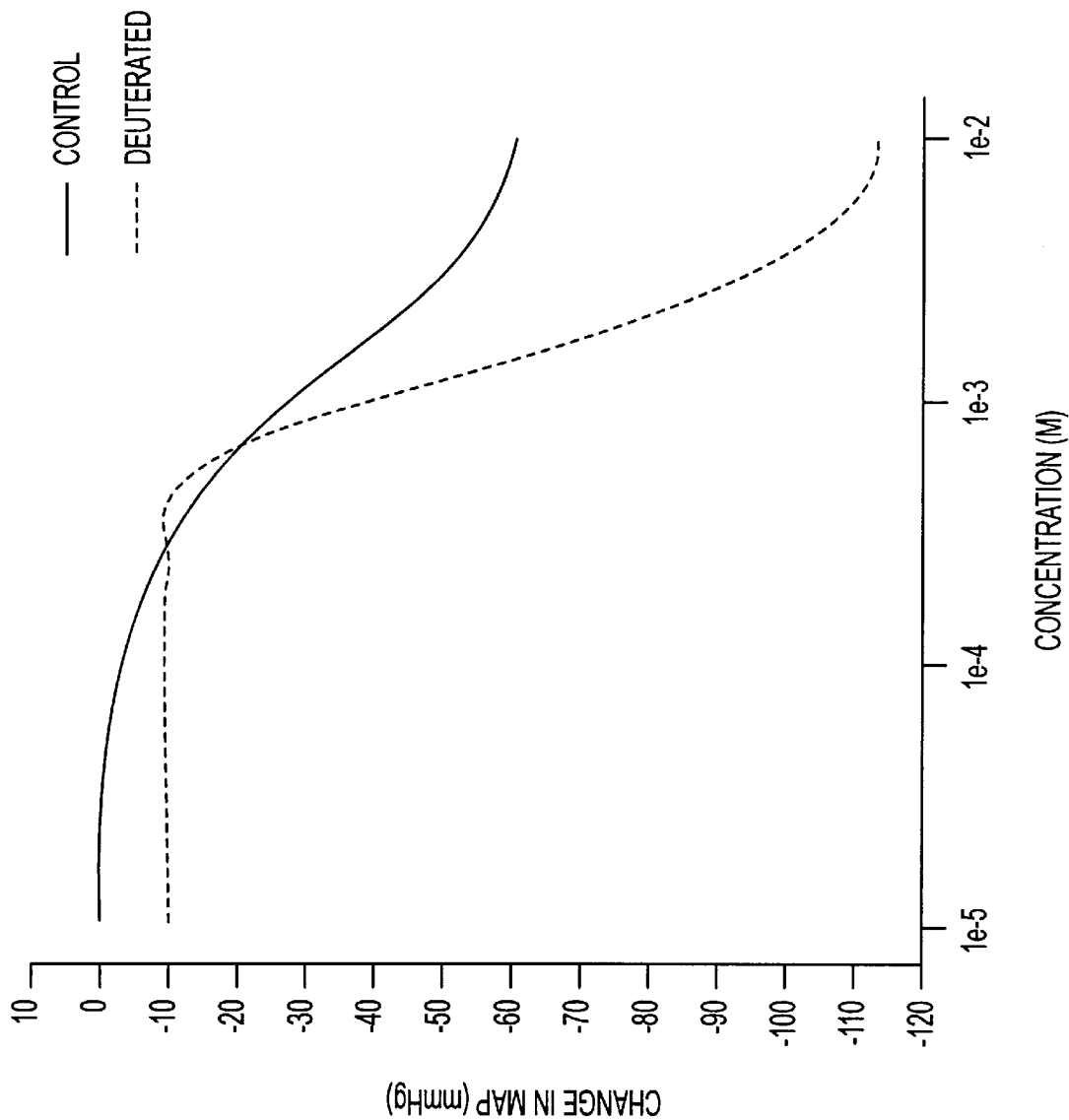

FIG. 6 shows the effect of control and deuterated nifedipine on mean arterial pressure: FIG. 6(a) shows actual values plotted, FIG. 6(b) shows curves fitted to data by logistic dose-response regression. A total of six rats were tested at each dose. As can be seen, at all doses deuterated nifedipine was more potent than control nifedipine (p<0.05 by repeated measures ANOVA). MAP=mean arterial pressure.

Figure 7A:
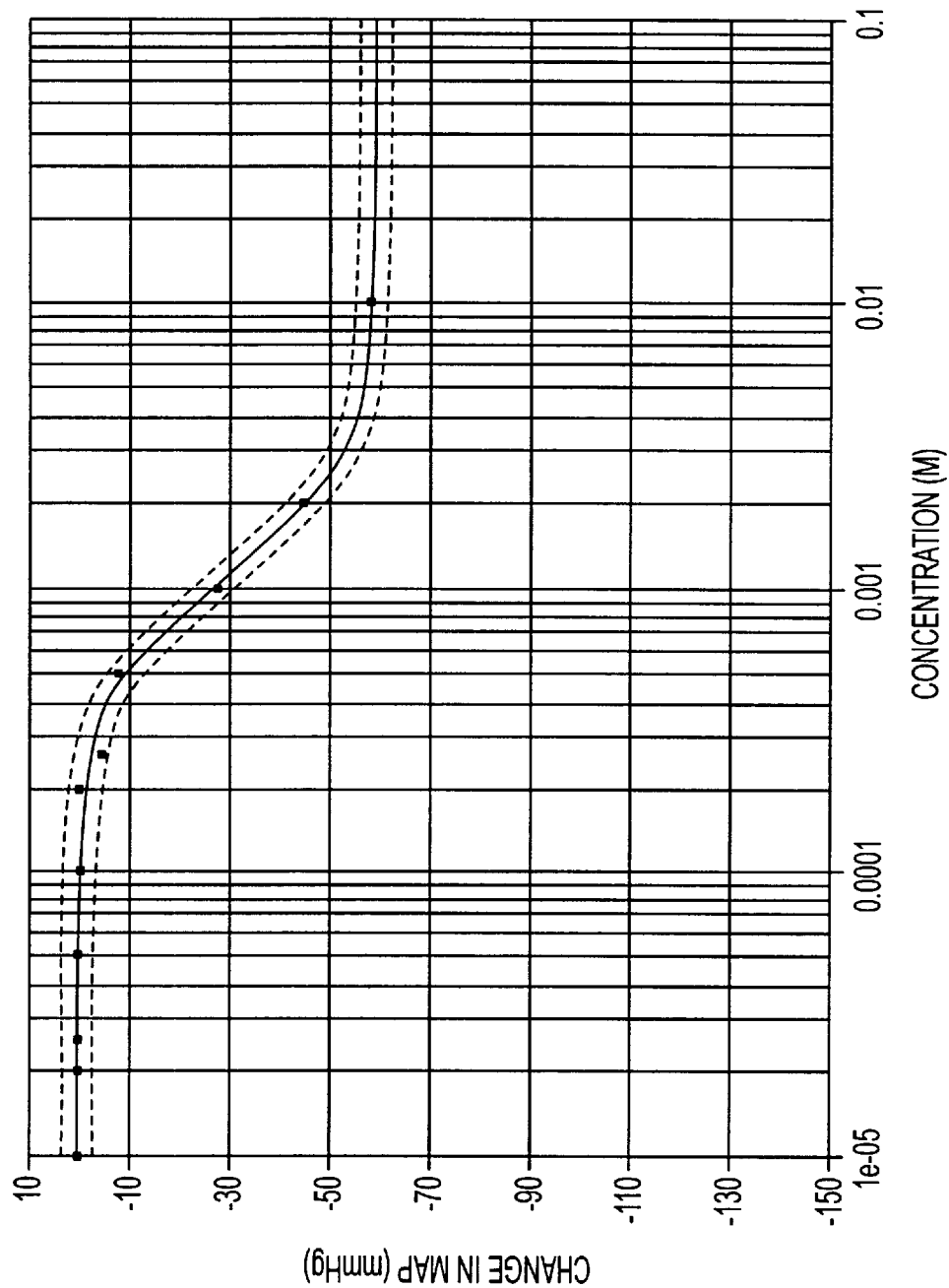
FIGS. 7(a) and (b) show concentration-effect relationships for control (FIG. 7(a)) and deuterated (FIG. 7(b)) nifedipine fitted using an asymmetric sigmoidal model.
Figure 7B:
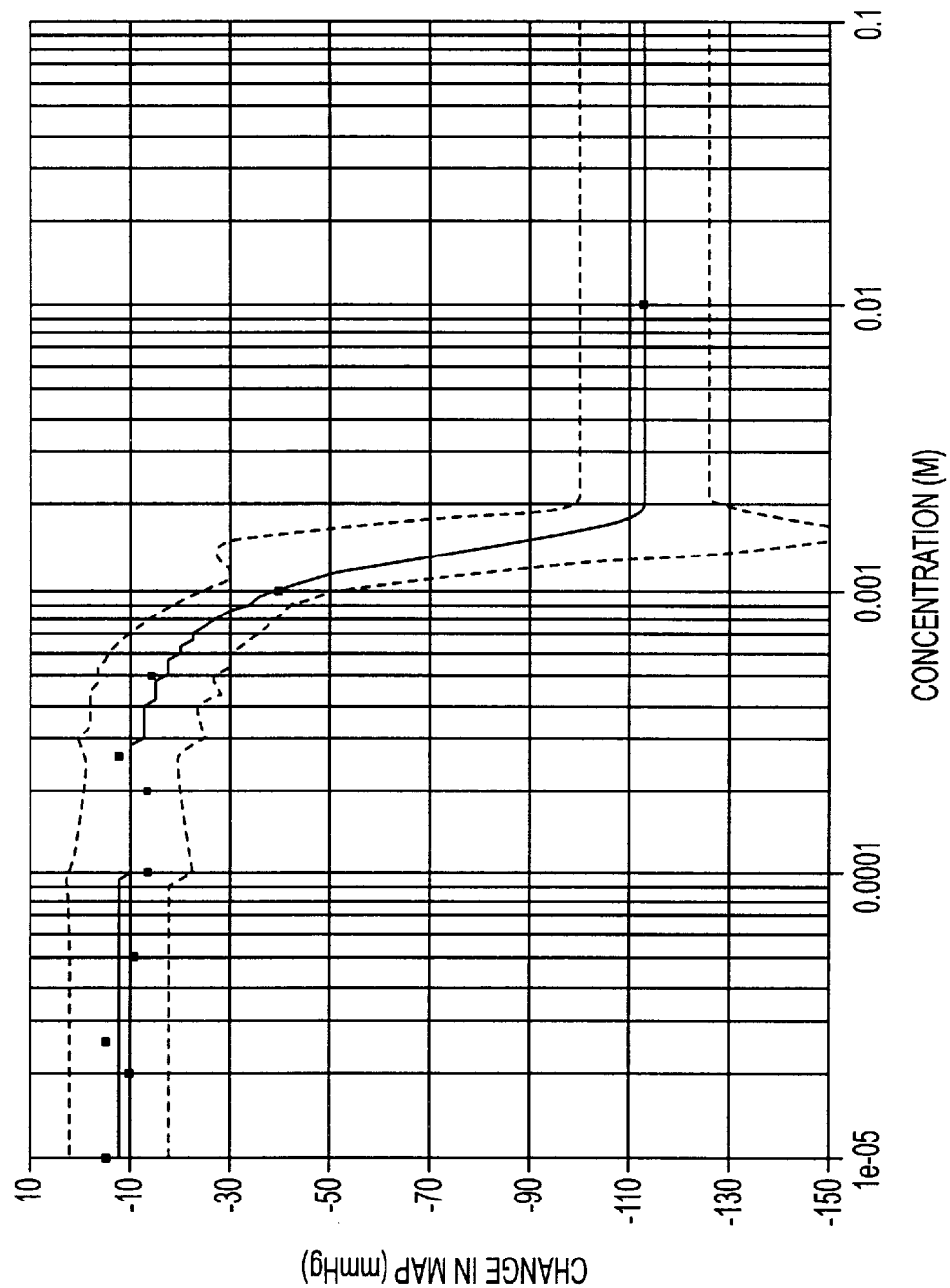

FIG. 7 shows concentration-effect relationships for control (FIG. 7(a)) and deuterated (FIG. 7(b)) nifedipine fitted using an asymmetric sigmoidal model. Fitted values plus 95% confidence intervals are shown. From these two graphs, based on a lack of overlap between the confidence intervals, it is evident that the concentration-effect relationships for the two nifedipines differ. To be more precise, curve fitting was carried out using the equation: $y=a+b(1-(1+\exp((x+d\ln(2^{1/e}-1)-c)/d))^{-e})$. On this basis the parameters a, b and e all differed statistically at p<0.05.

Figure 8A:
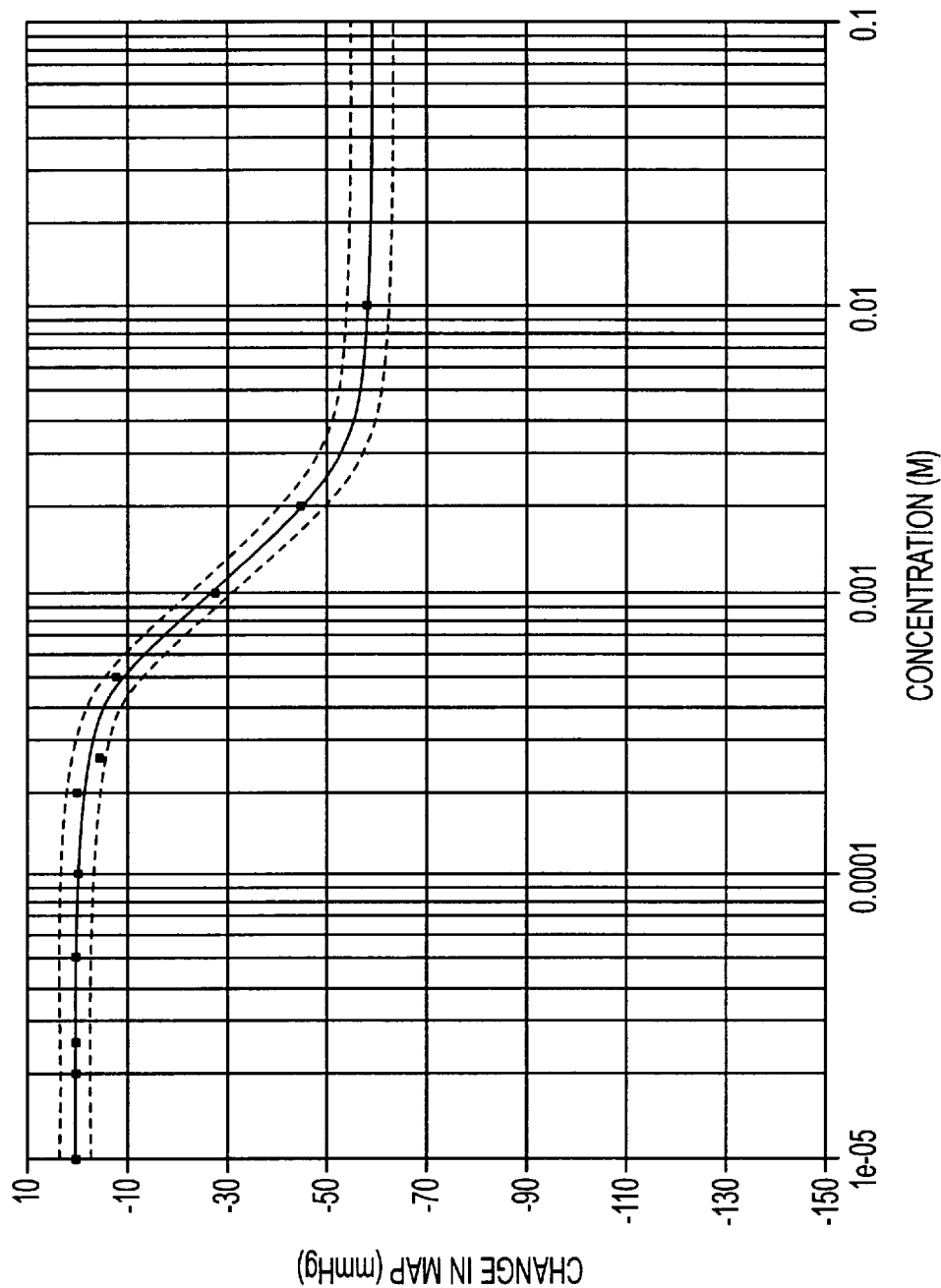
FIGS. 8(a) and (b) show concentration-effect relationships for control (FIG. 8(a)) and deuterated (FIG. 8(b)) nifedipine fitted using logistic dose response model.

FIG. 8 shows concentration-effect relationships for control (FIG. 8(a)) and deuterated (FIG. 8(b)) nifedipine fitted using logistic dose response model. Fitted values plus 95% confidence intervals are shown. From these two graphs, based on a lack of overlap between the confidence intervals, it is evident that the concentration-effect relationships for the two nifedipines differ. To be more precise, curve fitting was carried out using the equation: $y=a+b/(1+(x/c)^d)$ On this basis the parameters a and b all differed statistically at p<0.05.

EXAMPLE VI

Figure 9A:
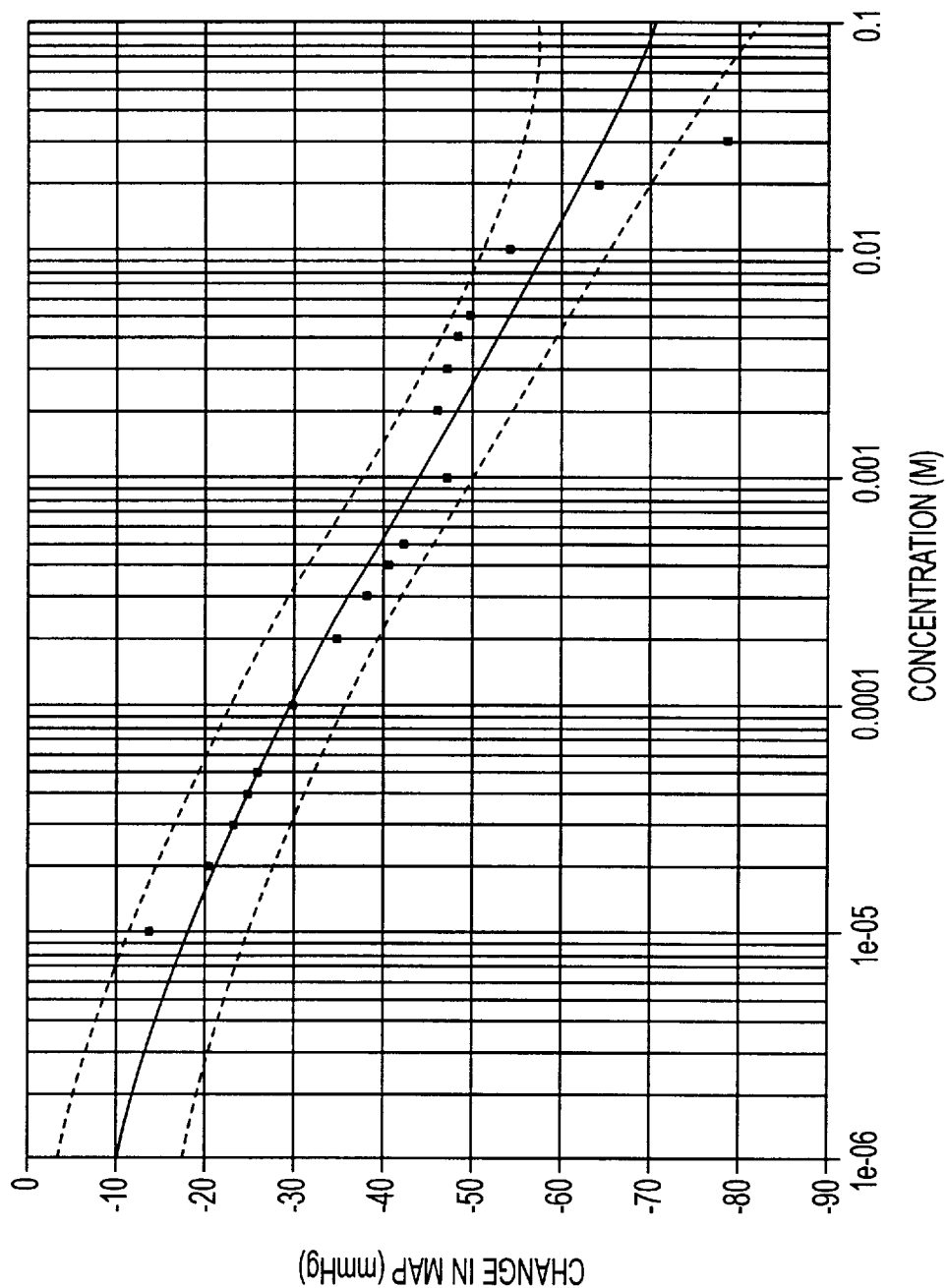

Effect of deuterated control nicardipines on blood pressure in normotensive Sprague-Dawley rats. Control and deuterated nicardipines (prepared, as described below, in a manner analogous to the preparation of deuterated nifedipine) were dissolved in minimal volumes of ethanol and diluted until the final concentration of ethanol was less than 0.04%. Doses of the two nicardipines as indicated were then injected into pentobarbital-anesthetized Sprague-Dawley rats weighing between 300 and 350 grams. The maximum change in mean arterial pressure, as well as the duration of hypotensive response, were measured directly by means of an intra-arterial catheter. Only one drug dose was given to each rat and a minimum of 60 minutes was allowed for blood pressure to return to baseline Potency-FIGS. 9a and 9b show the dose-response effect for the control and deuterated (test) nicardipines. Although the confidence intervals of the curves overlap in areas, statistical comparison of $ED_{16}$, $ED_{50}$, and $ED_{84}$ showed the following differences:

| | | | |
|---|---|---|---|
| $ED_{16}$ | control | $6.11 \times 10^{-6}$ mmoles | 95% CI: $2.2–16.8 \times 10^{-6}$ |
| | deutrated | $46.2 \times 10^{-6}$ mmoles | $37.3–57.2 \times 10^{-6}$ |
| $ED_{50}$ | control | $2.54 \times 10^{-3}$ mmoles | 95% CI: $1.53–4.20 \times 10^{-3}$ |
| | deutrated | $2.11 \times 10^{-3}$ mmoles | $1.48–3.00 \times 10^{-3}$ |
| $ED_{84}$ | control | 1.06 mmoles | 95% CI: 0.38–2.91 |
| | deutrated | 0.09 mmoles | 0.077–0.119 |

95% CI = 95% confidence interval

From the above table, it can be seen that the confidence intervals are exclusive for both $ED_{16}$ and $ED_{84}$. This indicates that the nature of the dose response relationships differs. This is confirmed by differing slope functions of 416 for control nicardipine and 46 for deuterated nicardipine (as calculated by Litchfield-Wilcoxon method). Thus, the potencies of the two formulations differ.

Two-way analysis of variance using dose and formulation as independent variables and reduction in mean arterial pressure as the dependent variable revealed the following ANOVA table:

| factor value | d.f | sum of square | mean square | F | p- |
|---|---|---|---|---|---|
| drug | 1 | 323 | 323 | 3.11 | .082 |
| dose | 17 | 5531 | 3255 | 30.8 | .0001 |
| drug × dose | 17 | 6464 | 380 | 3.6 | .0001 |

Although there is no difference at a p<0.05 level for drug differences (there is a difference at the 0.1 level, however), the lack of difference is likely due to the many doses clustered around the $ED_{50}$ where the curves do not differ. There is a marked drug x dose interaction, however, which does imply a difference in the nature of the dose-response curves.

Figure 10:
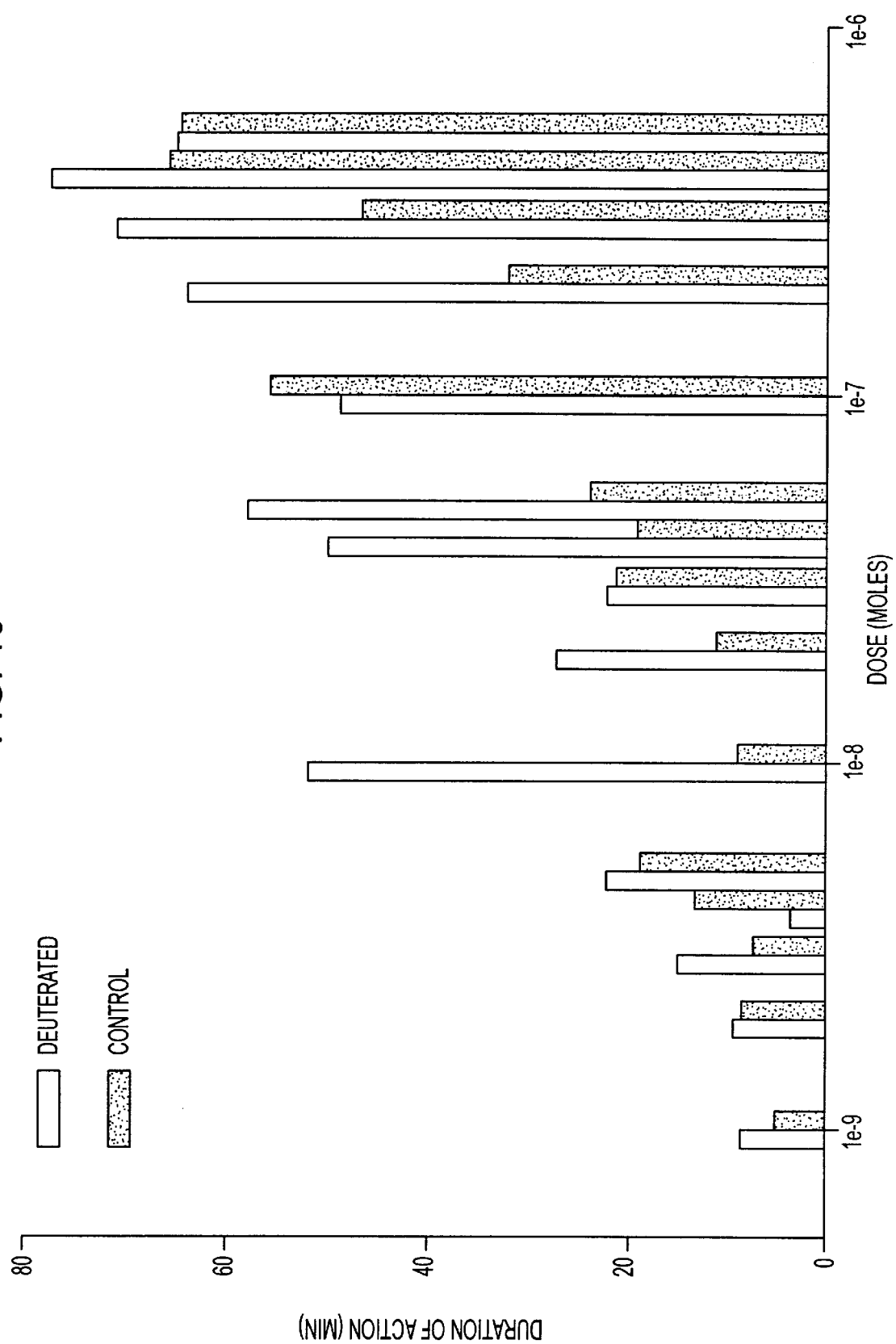
FIG. 10 shows the duration of effect was greater for deuterated nicardipine compared to control nicardipine.

Duration of action-At most time periods the duration of effect was greater for deuterated nicardipine compared to control nicardipine (FIG. 10). Because the duration of response might be dependent on the magnitude of decrease in blood pressure, however, equipotent doses of the two formulations were compared. In this comparison, control nicardipine at a dose of $1 \times 10^{-9}$ moles and deuterated nicardipine at a concentration of $3 \times 10^{-9}$ moles were compared (relative potencies −13.8 vs −13.8 mmHg control vs deuterated, p=NS). At these doses, despite an equivalent blood pressure effect, the duration of action of control nicardipine was 5.4+3.8 (SD) min and the duration of action of deuterated nicardipine was 15.0+6.4 (SD) min (p=0.049 by Mann-Whitney U-test). Thus, the duration of action of deuterated nicardipine is greater than that of control nicardipine independent of blood pressure lowering effectiveness.

Comparison of duration of action by two-way ANOVA using dose and formulation as independent variables and duration of action as the dependent variable revealed the following ANOVA table:

| factor value | d.f | sum of square | mean square | F | p- |
|---|---|---|---|---|---|
| drug | 1 | 5697 | 5697 | 24.0 | .0001 |
| dose | 14 | 68292 | 4878 | 20.6 | .0001 |
| drug × dose | 14 | 10678 | 237 | 3.2 | .0002 |

These results show significant differences in the duration of action of the two drugs as well as implying a difference in the nature of the dose-duration of action relationship.

Based on the above data, deuterated nicardipine differs from control nicardipine both in the nature of the blood pressure-lowering dose-response effect as well as in duration of action.

EXAMPLE VII

Preparation of deuterated nicardipine. Such modification of nicardipine (and other dihydropyridines) can be achieved by dissolving the nicardipine in a deuteration tube in a mixture of deuterochloroform and deuterium oxide, and then adding a minor amount of trifluoroacetic anhydride and deuteroacetone thereto and mixing therewith. The solution is then frozen within the tube, preferably by immersing the tube in liquid nitrogen and then sealing the tube. The sealed tube is then heated at a temperature within the range of from about 50° to about 65° C., and preferably within the range of about 55° to about 60° C., and maintained at that temperature for a period of time sufficient to deuterate the methyl group at 2 and 6 positions on the nicardipine to $CD_3$. A time of from about 150 to about 180 hours is effective to complete the reaction, with a time of about 160 to 170 hours being preferred.

Deuterated nicardipine was synthesized in the following manner: 80 mg of nicardipine in powder form was placed into a special deuteration tube and dissolved therein in a mixture of 2 ml of deuterochloroform and 0.5 ml of deuterium oxide after which 0.2 ml of trifluoroacetic anhydride and 2 ml of deuteroacetone were added and mixed therewith. The solution was frozen in liquid nitrogen and the tube flamed sealed under nitrogen. The tube was then heated at 57° C. for 168 hours after which it was cooled and opened. The contents of the tube were transferred to a round-bottom flask and the solvent was removed in vacuo on a rotovap. All operations were conducted under reduced intensity of light. Using conventional $^1H$ nuclear magnetic resonance (NMR) the deuterium substitution was calculated to be 95% of the C-2 and C-6 methyl groups shown above.

Given the profound effects of substitution of deuterium for hydrogen in the methyl groups attached to positions 2 and 6 of the dihydropyridine ring, and given the fact that all dihydropyridine calcium channel blockers have at least one methyl group in these positions (in fact, all dihydropyridines have 2 methyls except amlodipine which only has a 6 methyl, substitution of the 2 methyl with $CH_2OCH_2CH_2NH_2$ interestingly drastically increases the duration of action of this dihydropyridine), deuteration of these groups in any other dihydropyridine would be expected to have the same effect as in nifedipine.

EXAMPLE VIII

Effect of Deuterated and Control Verapamils on Blood Pressure in Normotensive Sprague-Dawley Rats.

Deuteration of verapamil-verapamil hydrochloride was added to a solution of 25% deuterated sulfuric acid in deuterated water (v/v) and deuterated methanol. The solution was stirred for 140 hours at 90° C. The pH was adjusted to 12.0 and the mixture extracted with ethyl acetate. The combined ethyl acetate extracts were washed with water, dried over magnesium sulfate and evaporated to yield a viscous oil. This oil was dissolved in ether and ethereal hydrochloride was added to precipitate the hydrochloride salt. The salt was collected by filtration and crystallized from ethyl acetate to obtain deuterated verapamil as a white solid.

Control and deuterated verapamils (wherein the aromatic positions of verapamil (a phenylalkylamine) were deuterated) were dissolved in minimal volumes of ethanol and diluted until the final concentration of ethanol was less than 0.04%. Doses of the two verapamils as indicated were then injected into pentobarbital-anesthetized Sprague-Dawley rats weighing between 300 and 350 grams. The maximum change in mean arterial pressure, as well as the duration of hypotensive response, were measured directly by means of an intra-arterial catheter. Only one drug dose was given to each rat and a minimum of 60 minutes was allowed for blood pressure to return to baseline. Results are shown below.

Figure 11:
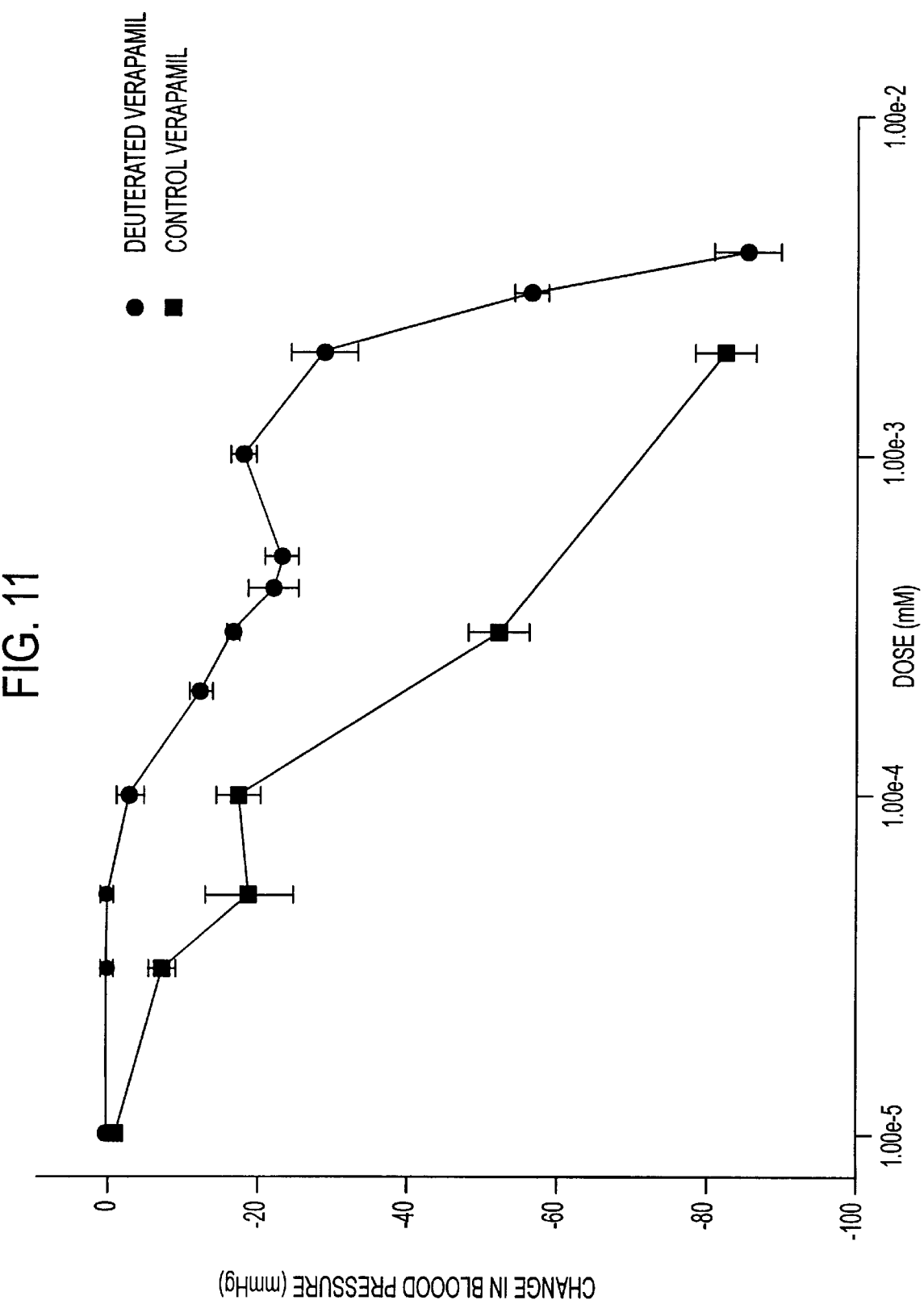
FIG. 11 shows the hypotensive effect of the various concentrations of the deuterated verapamil on the treated rats as compared with verapamil per se.

At each dose, the effect (potency) of deuterated verapamil was less than that of control verapamil (see FIG. 11). In terms of dose response, using approximately −90 mmHg as the maximum response, the $ED^{-50}$ for control verapamil was $2.89 \times 10^{-4}$ mm and $2.16 \times 10^{-3}$ mM for deuterated verapamil. This difference, along with differences in the entire dose response curves were different by Litchfield-Wilcoxon analysis. Indeed, potency ratio determined by this technique was 0.133 deuterated vs control (95% confidence intervals 0.07 to 0.25, p<0.001). Thus, the deuterated verapamil was less potent that control verapamil.

Figure 12:
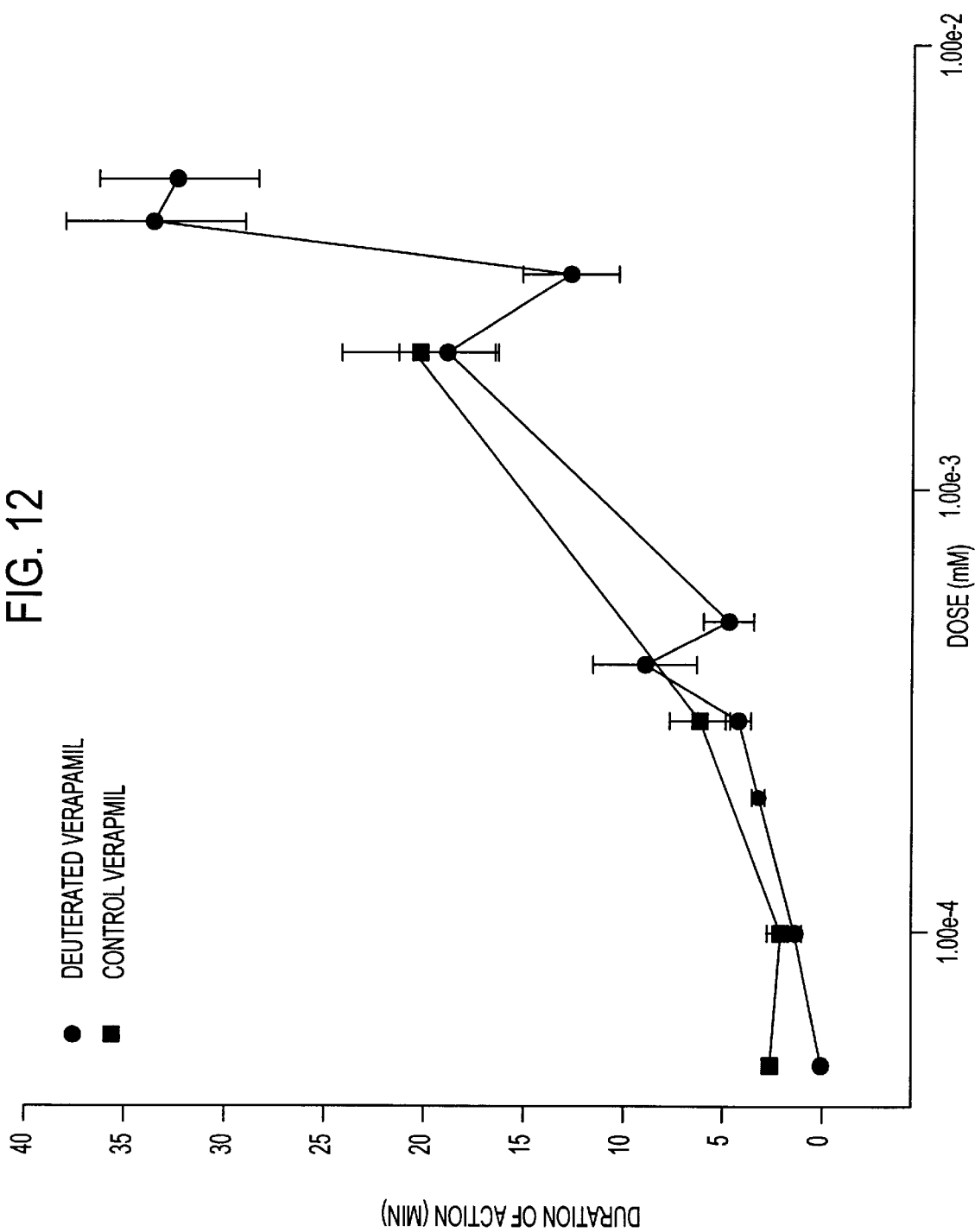
FIG. 12 shows the duration of effect was greater for deuterated verapamil compared to control verapamil.

In terms of duration of action, however, by Litchfield-Wilcoxon analysis, the deuterated verapamil had a longer duration of action (see FIG. 12). In addition, the dose-duration curves were also significantly different, giving a potency ratio of 4.95 for deuterated vs control (95% confidence interval 2.3 to 10.7, p<0.01). To compare another way, at equipotent doses ($0.3 \times 10^{-4}$ mM for control, $0.3 \times 10^{-3}$ mM for deuterated; BP reduction −52.8 and −57.0 mmHg respectively), the duration of action for deuterated vs control verapamil was 12.5 vs 6 minutes (p<0.01).

These results suggest that the potency and duration of action were altered by deuteration. As with the dihydropyridines, duration of action was prolonged by deuteration, but potency, unlike dihydropyridines, was decreased. Depending on the site of deuteration, however, potency could potentially be increased.

Thus, in view of the above, (1) duration of action is prolonged by deuteration (for all drugs tested); (2) potency is affected by deuteration: it is increased for dihydropyridines and decreased for verapamil (a phenylalkylamine); and (3) use-dependency is altered for dihydropyridines (it has not been tested for verapamil).

Prolonging the Duration of Action of Drugs Using Isotopes. Introduction:

Pharmaceutical manufacturers often spend several millions developing drugs that have long durations of activity. The quest for drugs with longer durations of action arises for several reasons including, for example: prolongation of the beneficial therapeutic effect; protection of the drug's market-share by new patents issued for the new drug dosage formulation; and increasing patient compliance (making it easier to take a once-a-day formulation instead of three-, or four-times-a-day formulation).

Each of the three drugs tested as discussed above (i.e., nifedipine, nicardipine, and verapamil) is currently being used in the treatment of hypertension (high blood pressure). As cardiovascular disease is a leading cause of death in North America, and hypertension is a significant risk factor, it is important that patients requiring these medications have drug concentrations in their circulation which protect them from these effects of high blood pressure 24 hours a day. Although some manufacturers offer two, three, or four times a day dosing, several are manufacturing drugs which have longer duration of action (longer half lives) by altering the dosage formulation. These dosage formulation alterations include, for example, inclusion of excipients that slow the drug's release, coating of formulations, newer formulations (e.g., osmotic pumps), and coated granules. Many of these modifications of the dosage formulation are extremely expensive to develop and manufacture.

Using the deuterated drugs disclosed herein, we have shown that we can modify drugs of different classes (e.g., 1–4 dihydropyridines and phenylalkylamines) and believe that our modification applies to all drugs, as the principle involved is the same, irrespective of the drug. Without being bound by theory, by deuterating drugs, we have likely produced two effects: increased the lipophilic nature of the molecule and rendered the C—H bond more thermodynamically stable by substituting the —H for —D (deuterium atom). The former point may allow the drug to distribute into more "deeper" tissue depots (such as adipose) and may linger in the body for a longer period of time. The latter point, however, is the point that should be regarded more carefully. By substituting the hydrogen by a deuterium atom, the resulting carbon (C) deuterium (D) bond becomes stronger. Hence, by increasing the mass of hydrogen (H) one atomic mass unit and creating a D, the C—D bonds are probably becoming stronger. This is done using D as a non-radioactive stable isotope of the H. Interestingly, as the C—D bond is thermodynamically more stable than the C—H bond, it is less easily cleaved by metabolic (or destructive) processes. Hence, the elimination half life of the drug is prolonged and the drug's therapeutic effects are increased. Although we have also observed that there may be changes in the drug's potency, the prolongation of the drug's effect is most striking.

In essence, therefore, by simply substituting an H by a D in the three molecules discussed above, we have created a new "modified release" drug by way of increasing the duration of the activity. Additionally, a distinct advantage of this method is that this method obviates the need for adding several potentially toxic excipient which are presently included in the modified release formulations.

EXAMPLE IX

"Fingerprinting" of compounds. Since the substituents of pharmaceutical compounds are usually elements of carbon, hydrogen, nitrogen, oxygen, etc., and these elements may exist in more than one isotopic form, the precise nature of these isotopic forms is determined by how and geographically where each chemical is made, particularly since each location where the drug is manufactured usually uses local chemical suppliers for its materials for synthesis. Here, a given pharmaceutical may be developed as a molecule with a very distinct pattern of isotopes present therein. Comparison of the known molecule manufactured by one manufacturer with the molecule of a similar pharmaceutical found in the marketplace can establish whether the second drug was made by the same manufacturer or by another. This is possible since each molecule has a very distinct pattern ("fingerprint") of isotopes. Gas chromatography-isotope ratio mass spectrometry (GC-IRMS) can be used to ascertain the materials that are present in a pharmaceutical preparation.

However, any suitable introduction system allowing compounds to enter into the isotope ratio mass spectrometer can be used, as for example gas chromatography and high performance liquid chromatography.

Although a generic drug product must pass certain specific tests prior to being approved for the marketplace, it has been determined that such generic drug product consumed by a patient may not have the same quality as that of a drug manufactured by the innovators of that drug. Differences in quality may be related to impurities or to differences in the chemical make-up of the drug molecule, which differences are not detected using standard testing procedures but are detected by the use of GC-IRMS (described below) for determining the molecular structure of the drug molecule.

From the foregoing, it is readily apparent that pharmaceutical preparations which contain identical amounts of a drug may not be bioequivalent. This inequivalency may be entirely due to the isotopic mixture of all of the elements which are included in a particular pharmaceutical. Such isotopic differences between a generic drug and one of a known manufacturer made under the rights of the innovator of that drug could result in inadvertent over- or under-dosing if one formulation is substituted for another. This may mean, for example, that previously well-controlled angina or hypertension may not be controlled upon exchanging one formulation for another, leaving a physician puzzled as to why the drug is no longer performing as expected. Conversely, patients who previously experienced no adverse drug effects may begin to develop side effects from the new formulation. In addition, the duration of clinical effect may differ between two different formulations. In accordance with an embodiment of this invention, a new drug appearing on the market and sold as an equivalent of a known drug which has been on the market and made by one manufacturer can be readily analyzed for bioequivalency with the known drug.

BASIS OF THE METHOD OF IRMS

Isotope ratio mass spectrometry (IRMS) is a highly precise method of analysis which is able to measure small samples (low nanogram amounts). For example, $^{13}C/^{12}C$ ratios are determined on a mono-carbon molecule; $CO_2$ gas. Therefore, organic carbon has to be converted to $CO_2$ gas by combustion over cuprous oxide (CuO, on-line combustion oven or elemental analyzer) and cryogenically or chromatographically purified. The $CO_2$ gas can then be immediately directed to the spectrometer by means of a continuous flow IRMS (also called CF-IRMS).

The statistical combination of the isotopes of carbon ($^{12}C$ and $^{13}C$) and oxygen ($^{16}O$, $^{17}O$, $^{18}O$) to generate the $CO_2$ molecules gives rise to the formation of various isotopomers whose molecular weights are 44, 45, and 46, respectively. Thus, for measuring carbon isotope ratios, three ion beams are generated and recorded in the IRMS, corresponding to the masses of the various isotopomers of $CO_2$.

In order to obtain a high precision and a high accuracy, reference gases of absolutely known isotopic composition are used and a dual inlet system allows an alternative admission of both sample and reference gas into the ionization source via a gas-switching valve. The measurement of the various ion beams allows for the calculation of the $^{13}C$ enrichment of the sample. The value of this calculation is given $\delta^{13}C(‰)$ notation. The $^{13}C$ abundance is expressed as $\delta^{13}C(‰)$ according to the following:

$$\delta^{13}C(‰)=([(^{13}C/^{12})sample/(^{13}C/^{12}C)PDB]-1)\times 1000$$

This $\delta^{13}C(‰)$ value measures the variations in parts per thousand of the carbon isotope ratio from the standard. For carbon, PDB was selected as the international reference. PDB is Pee Dee Belemnitella (a fossil from the Pee Dee geological formation in South Carolina). The $^{13}C/^{12}C$ ratio from the calcium carbonate of this fossil is 0.011237. Compared to PDB, most of the natural compounds display a negative delta value. In the above equation, $^{13}C/^{12}C$ refers to the isotopomers.

The measurement of the various ion beams for $^{15}N$ is given a $\delta^{15}N(‰)$ notation. The $^{15}N$ abundance is expressed as $\delta^{15}N(‰)$ according to the following equation:

$$\delta^{15}N(‰)=[(^{15}N/^{15}N\ sample)-(^{15}N/^{14}N\ standard)/(^{15}N/^{14N})\ standard]\times 1000.$$

The $\delta^{15}N(‰)$ value measures the variations in parts per thousand of the nitrogen isotope ratio from the standard. For nitrogen, air was selected as the international reference.

The measurement of the various ion beams for $^{18}O$ is given a $\delta^{18}O(‰)$ notation. The $^{18}O(‰)$ abundance is expressed as $\delta^{18}O(‰)$ according to the following equation:

$$\delta^{18}O(‰)=[(^{18}O/^{16}O\ sample)-(^{18}O/^{16}O\ standard)/(^{18}O/^{16}O)standard]\times 1000.$$

The ($\delta^{18}O(‰)$ value measures the variations in parts per thousand of the oxygen isotope ratio that is, oxygen derived from $CO_2$ from the standard. For oxygen, $CO_2$ was selected as the international reference.

IRMS INSTRUMENTAL SETTINGS

The isotope ratio mass spectrometer was a Finnigan MAT 252 (Bremen, Germany), equipped with a dual inlet mode and an elemental analyzer for introduction of non-gas samples. Samples were weighed such that each contained approximately 10–20 $\mu$m and transferred to tin capsules. The closed tin capsule was housed in the automatic introduction system (elemental analyzer model NA1500 NC, Fisons, UK). Samples were combusted at 1080° C. with oxygen and oxidation catalysts (CrO+CuO). The purified $CO_2$ was analyzed by the continuous flow IRMS. The $CO_2$ standard was $^{13}C$ Oztech $CO_2$ (dC(PDB)=−36.49 ‰; dO(PDB)=−25.56 ‰; dO(SMOW)=+15.06 ‰) obtained from Oztech Trading Corporation, Dallas, Tex., U.S.A. Other standards run were atropine (C, 70.56%, H, 8.01%; N, 4.84%; O, 16.59%) and phenanthrene (C, 93.556%; H, 5.615%; N, 0.180%; S, 0.456%). The purified nitrogen was analyzed by the continuous flow IRMS. The N standard was $^{15}N$ Oztech nitrogen (dN(AIR)=−1.89 ‰; obtained from Oztech Trading Corporation, Dallas, Tex., U.S.A.

Instrumental settings were: high voltage (HV), 10 kV; cathode, 5.74 A; emission, 1.473 mA; trap emission, 0.937 mA; electron energy, 75.0 −V; trap, 50.1 V.

APPLICATION OF ISOTOPE RATIO MASS SPECTROMETRY FOR FINGERPRINTING

A number of pharmaceuticals, including nifedipine, ciprofloxacin, ketoprofen, zopiclone and acebutolol have been investigated using an isotope ratio mass spectrometer (IRMS) for the determination of source of manufacture. This method for producing a "fingerprint" is based, for example, on ratios of $^{13}C/^{12}C$ which are determined from $CO_2$ gas; oxygen and nitrogen isotope ratios can also be used for "fingerprinting". The organic carbon in the pharmaceutical is converted to $CO_2$ by combustion over cuprous oxide and purified cryogenically or chromatographically. The resulting $CO_2$ is transferred directly to the spectrometer by continuous flow via a transfer line to the IRMS.

In order to maintain a high degree of precision for the measurement of the isotopes of $CO_2$, a reference gas of absolutely known isotopic composition is admitted to the IRMS through a dual inlet system which enables the alternate input of both a sample gas (from the pharmaceutical) and a reference gas. The analysis generates a $^{13}C/^{12}C$ ratio ($\delta‰$) which is expressed as follows:

$$\delta‰=(R_{sample}-R_{standard})/R_{standard})\times 1000$$

This $\delta‰$ (delta per mil) value measures the variations in parts per thousands of the carbon isotope ratio from the standard. It is this value which is used in the fingerprinting of pharmaceuticals.

Raw materials (active ingredients) as well as finished products (e.g., tablets) were analyzed. The results for the pharmaceuticals which have been processed are as follows:

I.R.M.S. RESULTS FOR RAW MATERIALS
AND FINISHED PRODUCTS FINGERPRINTING

| MOLECULE | NAME/BATCH | δ % (MEAN) | STD. DEVIATION | RAW MATERIAL OR FINISHED PRODUCT |
|---|---|---|---|---|
| Acebutolol | ABC-191-MP | −30.67 | 0.10 | RM |
| Acebutolol | 4435910222 | −28.84 | 0.08 | RM |
| Acebutolol | J57 | −30.65 | 0.06 | RM |
| Zopiclone | M-23078 9321500 RPR | −30.42 | 0.05 | RM |
| Zopiclone | M-23149 9332900 RPR | −33.93 | 0.04 | RM |
| Zopiclone | M-23077 9322900 | −31.43 | 0.08 | RM |
| Zopiclone | 62H4023 | −33.20 | 0.05 | RM |
| Nifedipine | OEHS SA Sanofi | −26.67 | 0.10 | RM |
| Nifedipine | 39163032 | −32.07 | 0.04 | RM |
| Nifedipine | 1838H8 Siegfried | −29.41 | 0.11 | RM |
| Nifedipine | 7113-Sumika | −39.69 | 0.03 | RM |
| Nifedipine | 038-1016B- Seloc AG | −30.35 | 0.14 | RM |
| Nifedipine | NF-19010 Quimicha Aimar | −35.92 | 0.07 | RM |
| Nifedipine | C.F.M. Milanese | −19.61 | 0.07 | RM |
| Nifedipine | 795019 | −36.67 | 0.24 | RM |
| Nifedipine | PT240563H Bayer AG | −30.03 | 0.15 | RM |
| Nifedipine | PT257982A Bayer AG | −30.50 | 0.10 | RM |
| Nifedipine | PT257981B Bayer AG | −30.59 | 0.09 | RM |
| Nifedipine | PT249877D Bayer AG | −31.17 | 0.15 | RM |
| Nifedipine | PT257980D Bayer AG | −30.66 | 0.09 | RM |
| Nifedipine | 898556A Bayer AG | −30.09 | 0.13 | RM |
| Nifedipine | 899612A Bayer AG | −30.51 | 0.09 | RM |
| Nifedipine | 898552S Bayer AG | −30.45 | 0.13 | RM |
| Nifedipine | 898553K Bayer AG | −30.32 | 0.10 | RM |
| Nifedipine | 898555C Bayer AG | −30.21 | 0.14 | RM |
| Nifedipine | 2704 Dexxon Israel | −29.67 | 0.08 | RM |
| Nifedipine | NI-S-891101 China | −34.33 | 0.06 | RM |
| Nifedipine | 50-OEHS SA Sanofi | −28.75 | 0.08 | RM |
| Nifedipine | 038.1016B Seloc AG Switzerland | −30.05 | 0.20 | RM |
| Nifedipine | 150 Cipla Bombay | −28.40 | 0.05 | RM |
| Nifedipine | 208143 Sumika Japan | −35.67 | 0.21 | RM |
| Nifedipine | K8192400 Klinge Pharma GMBh Germany | −28.14 | 0.14 | RM |
| Nifedipine | 5486 MI/01102 Zambon Group Italy | −33.46 | 0.15 | RM |
| Ciprofloxacin | 43/93 Union Quimico Farmaceutia, Spain | −34.62 | 0.09 | RM |
| Ciprofloxacin | 92/18 Fako, Istanbul | −35.84 | 0.07 | RM |
| Ciprofloxacin | 930501, Shanghai | −30.02 | 0.17 | RM |
| Ciprofloxacin | F30394 Cipla Bombay | −34.22 | 0.06 | RM |
| Ketoprofen | BP E1344-11507191 | −27.66 | 0.29 | RM |
| Nifedipine (Allotop L10) | 92001 | −32.3 −32.1 | ** | FP |
| Nifedipine (Atenerate L20) | 202 | −34.0 −33.9 | ** | FP |
| Nifedipine (Cardioluft L10) | 2FC | −33.9 −34.6 | ** | FP |
| Nifedipine (Casanmil S10) | BABP | −32.3 −32.1 | ** | FP |
| Nifedipine (Corinael L10) | CF109D | −32.5 −32.7 | ** | FP |
| Nifedipine (Adalat L10) | B533 | −28.6 −28.9 | ** | FP |

The above information confirms that IRMS can be used to "fingerprint" pharmaceuticals from various sources of manufacture. This information can be used to source pharmaceuticals, whether as raw materials (active ingredients) or as finished product.
**only two determinations were made. Mention of a standard deviation, therefore, was not appropriate.

The above information confirms that IRMS can be used to "fingerprint" pharmaceuticals from various sources of manufacture. Such information can be used to source pharmaceuticals, whether as raw materials (active ingredients) or as finished product.

Figure 13:
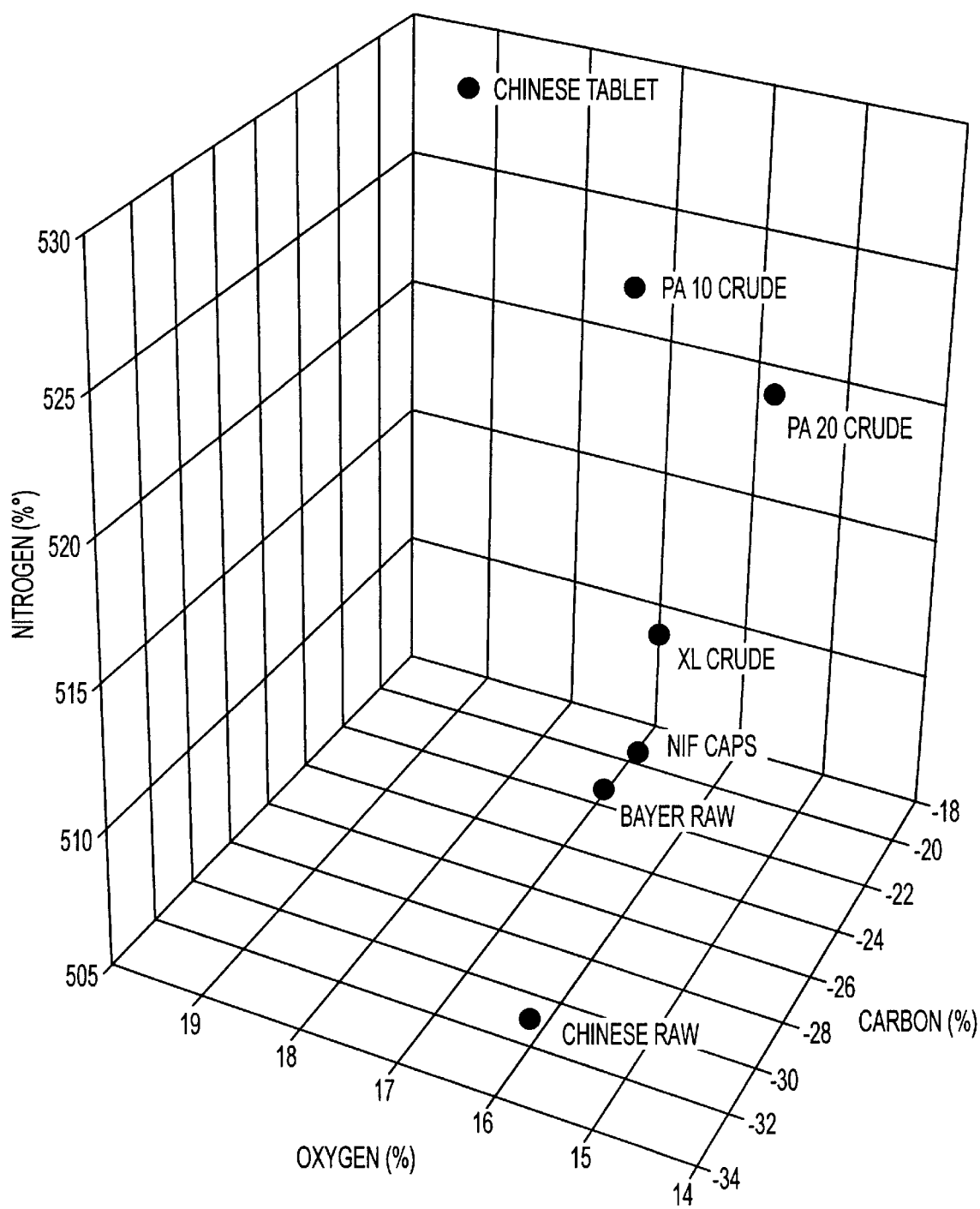
FIG. 13 shows a three dimensional "fingerprint" of seven nifedipine preparations.

FIG. 13 shows a three dimensional "fingerprint" of seven nifedipine preparations. All of these preparations are significantly different from each other. This type of three dimensional "fingerprint" is what would typically be done to provide the most sensitive "fingerprint" of a drug or any other substance.

Figure 14:
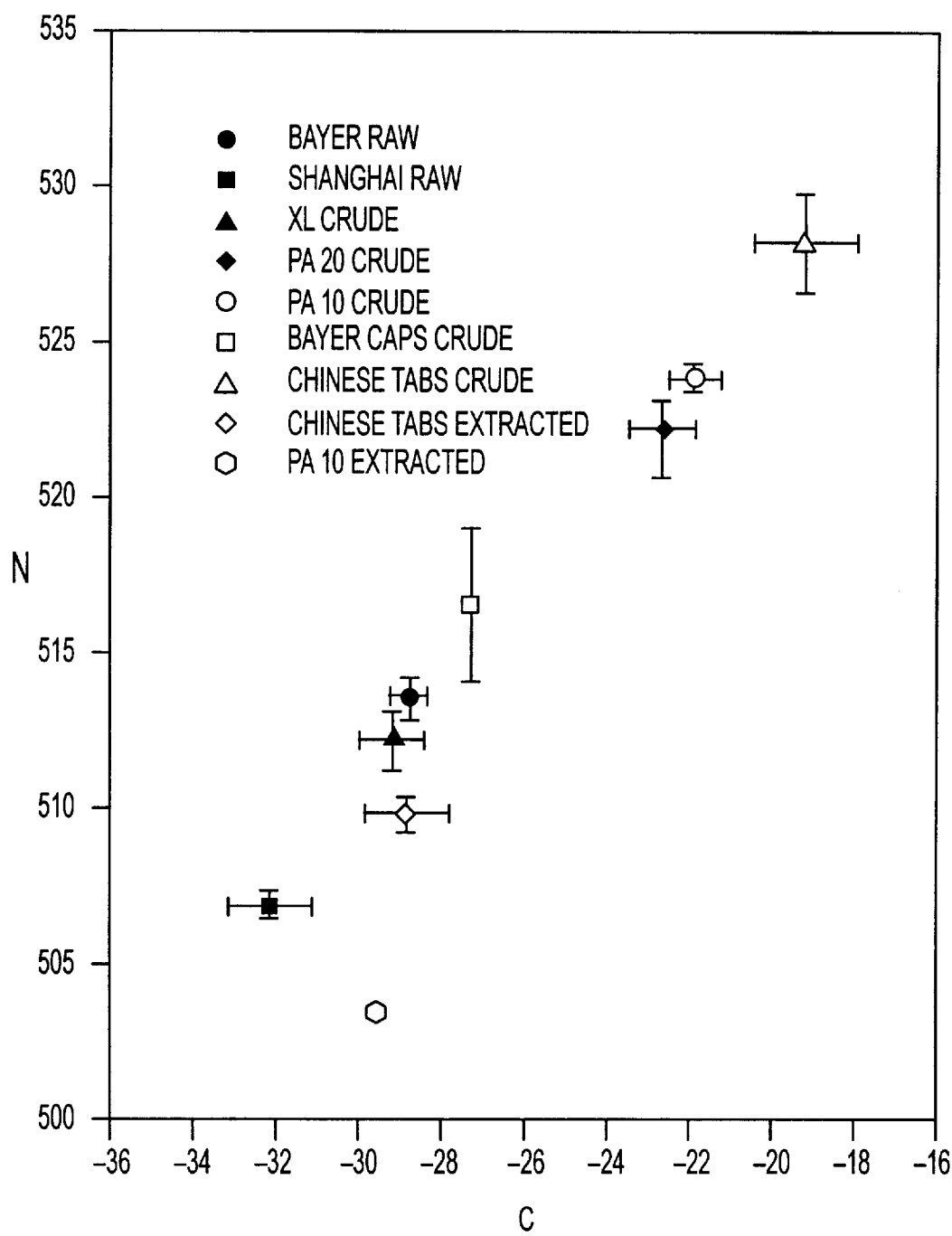
FIG. 14 shows a two dimensional "fingerprint" of nine nifedipine preparations.

FIG. 14 shows a two dimensional "fingerprint" of nine nifedipine preparations. The error lines are 95% confidence intervals; thus, all of the preparations are significantly different from each other. Although three dimensional "fingerprinting" gives a more precise "fingerprint", in practice two dimensional "fingerprinting" is usually sufficient to differentiate materials.

Figure 15:
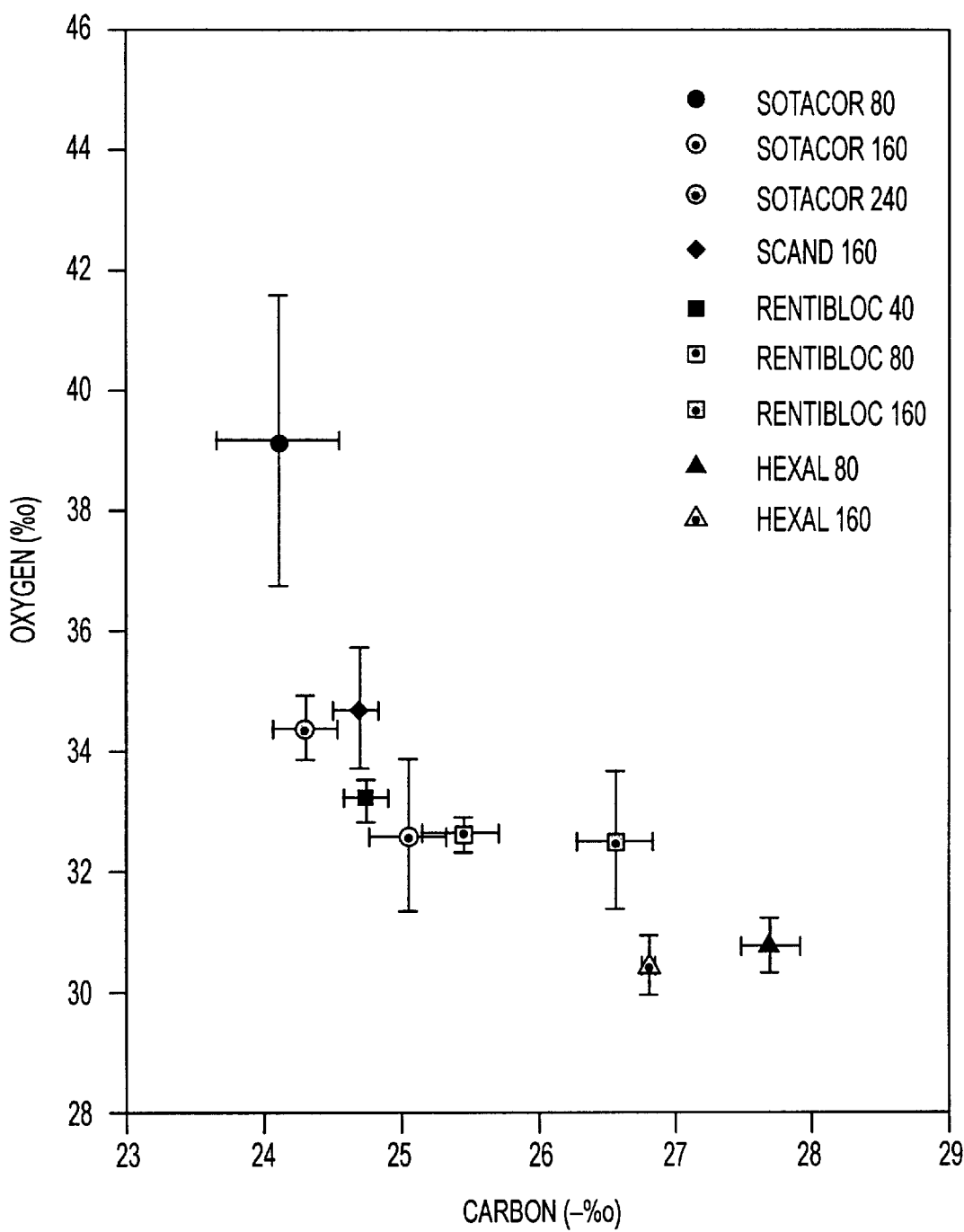
FIG. 15 shows a two dimensional (oxygen vs. carbon) "fingerprint" of solatol crude tablets.

FIG. 15 shows a two dimensional (oxygen vs. carbon) "fingerprint" of solatol crude tablets. Most of the tablets can be differentiated from each other by the two dimensional technique though carbon-oxygen two dimensional "fingerprinting" is less precise than carbon-nitrogen "fingerprinting".

Figure 16:
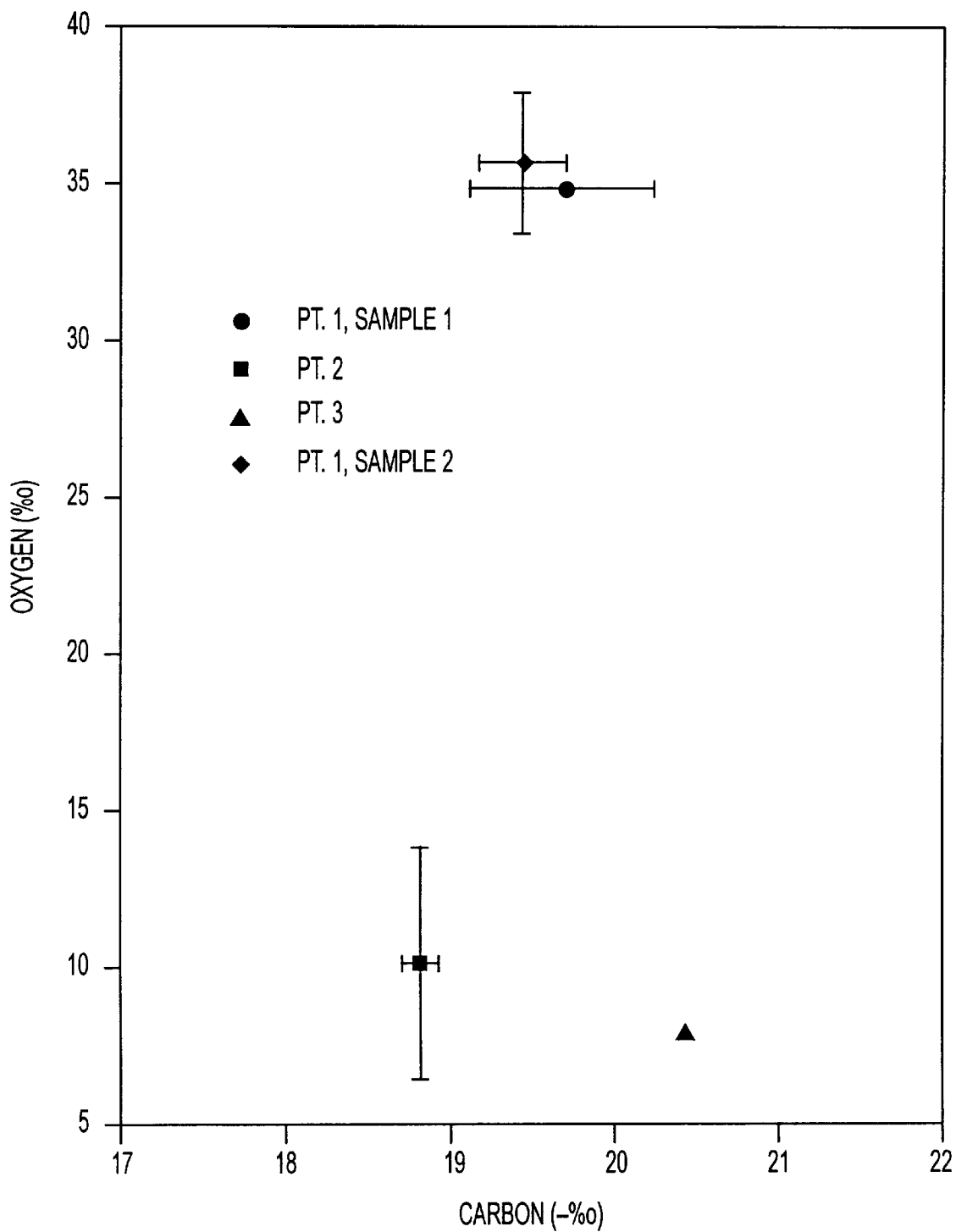
FIG. 16 shows "fingerprints" of three different hair samples from three different people.

FIG. 16 shows "fingerprints" of three different hair samples from three different people. In the case of the first patient (pt.1), a second sample was obtained one week later and compared with the first. This comparison gave a statistically identical value to the first sample, thus showing that this technique is reproducible and can be used to identify hair samples.

Figure 17:
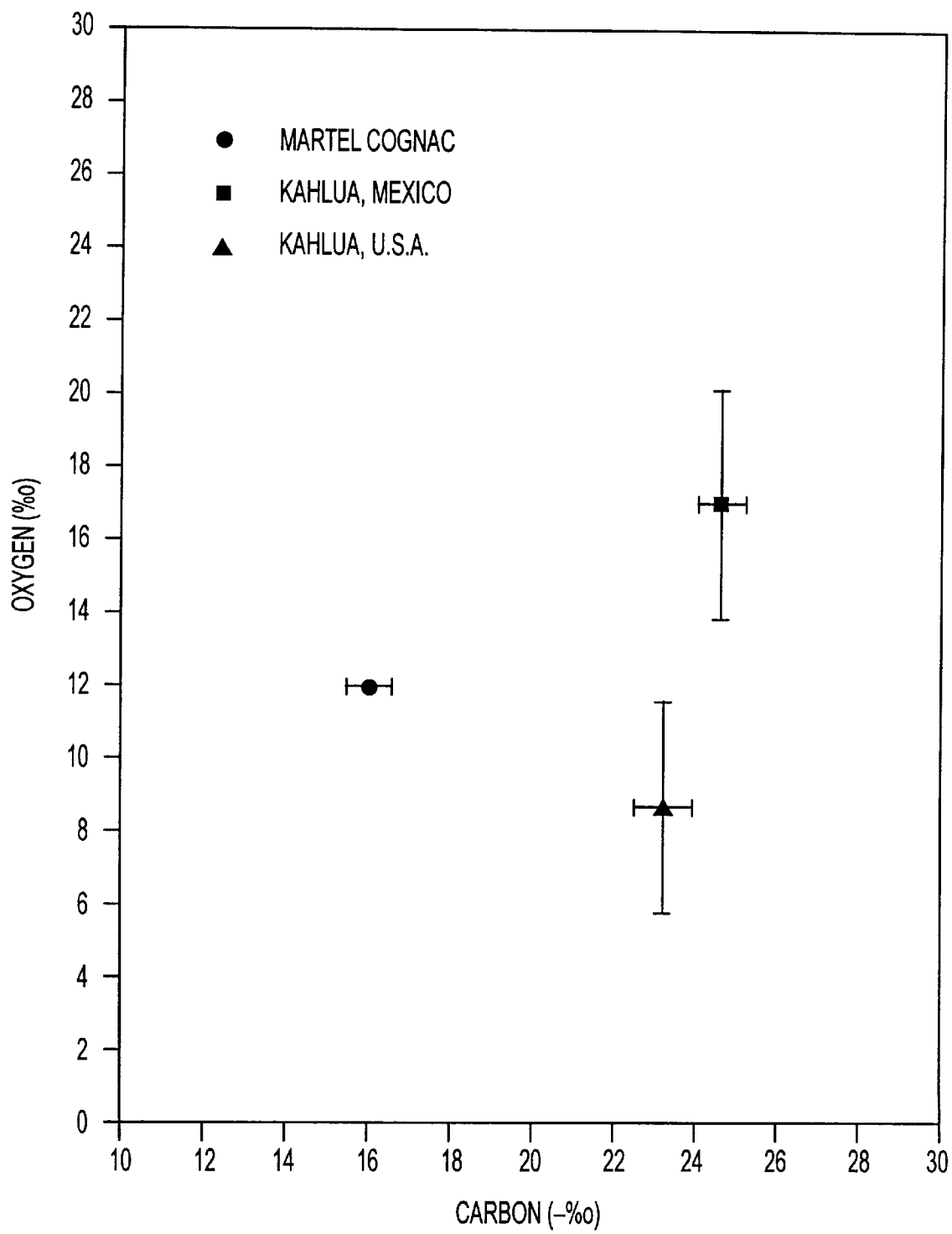
FIG. 17 shows a two dimensional carbon-oxygen "fingerprint" of three liquors.

FIG. 17 shows a two dimensional carbon-oxygen "fingerprint" of three liquors. Though two of the liquors are of the same brand, "fingerprinting" can differentiate them according to country of origin.

Thus, a feature of the present invention is a method of detecting whether a second pharmaceutical compound is identical and/or bioequivalent to a known pharmaceutical compound comprising the steps of (a) determining the molecular and isotopic structure of said known pharmaceutical compound by isotope ratio mass spectrometry using formulae selected from the group consisting of $\delta^{13}C(‰)=(((^{13}C/^{12}C) \text{ sample}/(^{13}C/^{12}C)\text{PDB})-1)\times 1000$, $\delta^{15}N(‰)=((^{15}N/^{14}N \text{ sample})-(^{15}N/^{14}N \text{ standard})/(^{15}N^{14}N)\text{standard})\times 1000$, and $\delta^{18}O(‰)=((^{18}O/^{16}O \text{ sample})-(^{18}O/^{16}O \text{ standard})/(^{18}O/^{16}O \text{ standard})\times 1000$, wherein at least two formulate are selected, (b) determining the molecular and isotopic structure of said second pharmaceutical compound by isotope ratio mass spectrometry using the same formulae selected in (a), (c) comparing the results of said two determinations to detect any isotope variation in the molecular structure of said second pharmacuetical compound over that of the known pharmaceutical compound.

In a preferred embodiment, three formulae are used. Thus, the use of two or three "dimensional" analysis is valuable for identifying or sourcing organic molecules. Specifically we demonstrate the use of the $^{13}C/^{12}C$ ratio in concert with the $^{15}N/^{14}N$ and/or the $^{18}O/^{16}O$ ratio (or any two of the preceding) to obtain an isotopic "fingerprint" of a molecule. The use of two or three "dimensions" (and optionally a fourth and fifth in the form of hydrogen and sulfur isotopes) tremendously enhances the specificity of the identification. By way of illustration, FIG. 14 shows two groups of nifedipines whose $^{13}C/^{12}C$ ratio overlaps (Bayer raw, XL crude, Chinese extracted; PA 10 crude, PA 20 crude). Using only two dimensions in our analysis, we are able to discriminate between the products. Using a third dimension (FIG. 13) provides even better specificity.

According to another aspect of the invention a variety of other pharmaceutical agents, particularly antibacterials, can be modified in accordance with the present invention. Included among the list of agents that can be modified are substances that are anti-hyperlipoproteinemics, anti-malarial, analgesics, cardiac medications (anti-arrhythmics), anti-ulcer agents, anti-fungals and immunosuppressive agents.

Specific examples of these are shown in the following charts in their deuterated form.

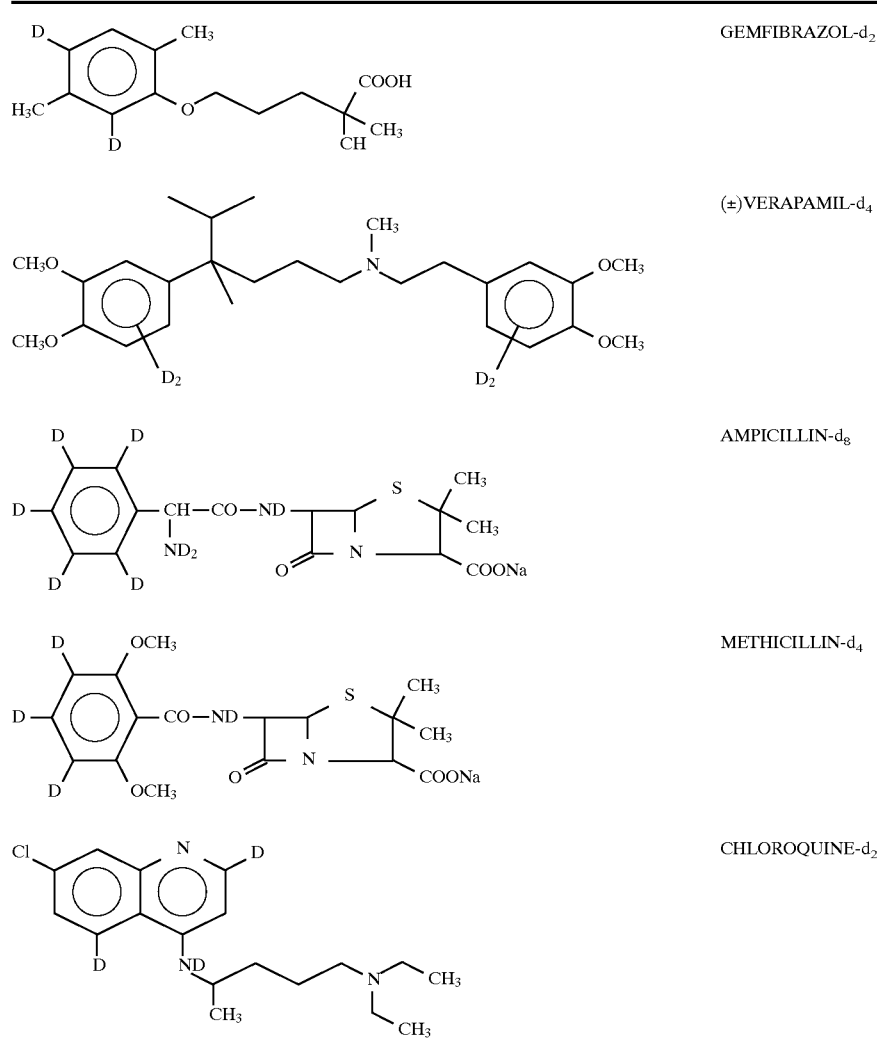

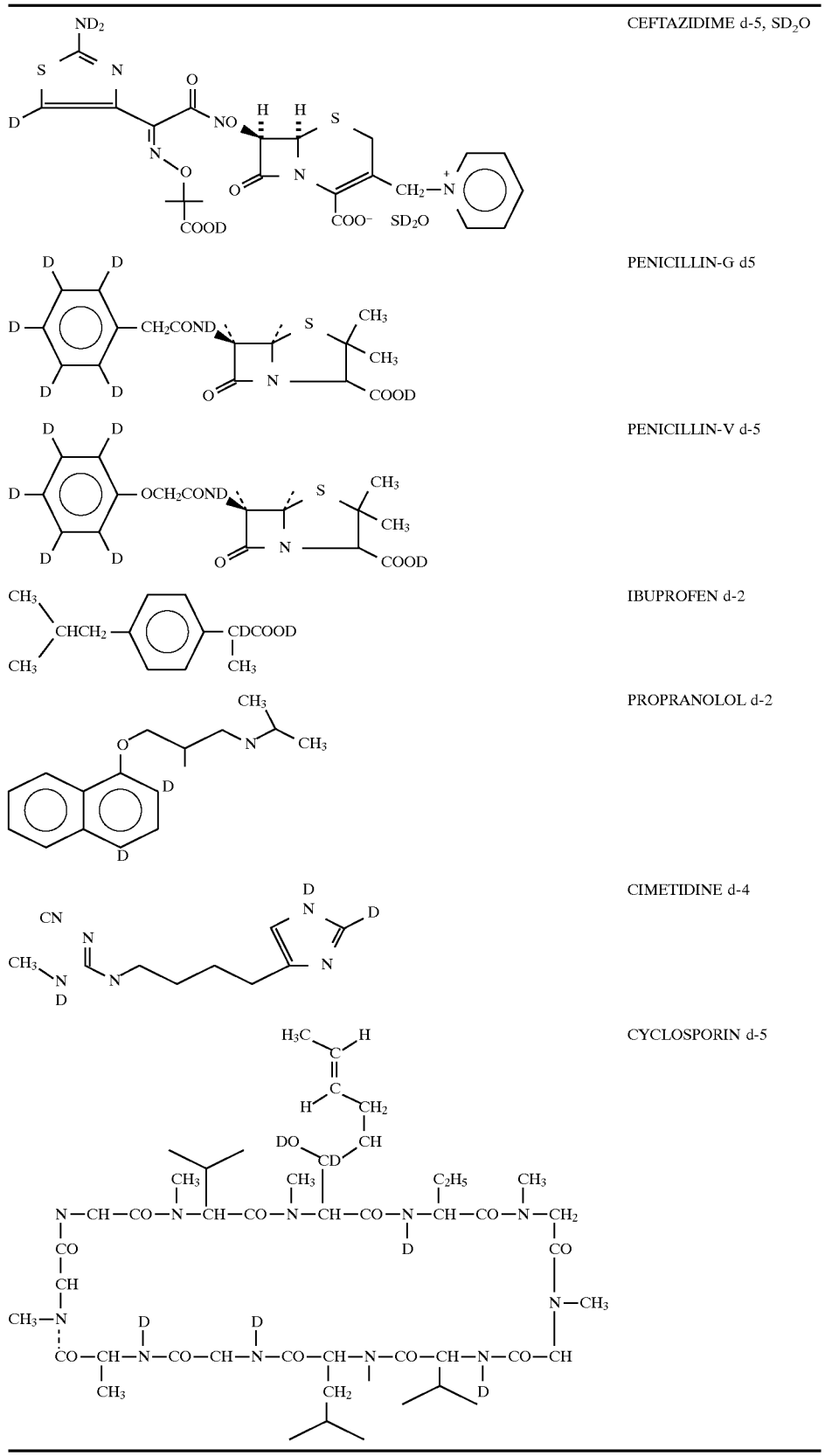

The following examples serve to illustrate the applicability of the present invention to a variety a pharmacueticals, here illustrated by anti-bacterials.

Synthesis of Penicillin V

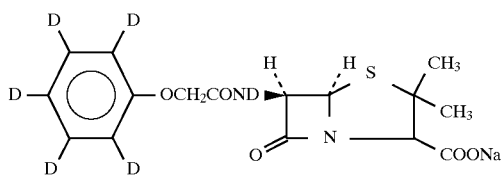

EXAMPLE X

Preparation of Phenoxy(d5)acetic acid

Phenol (d5) 4.6 g, ethyl chloroacetate (6.25 g), sodium iodide (7.5 g) and anhydrous potassium carbonate (7 g) were refluxed for 12 hours in dry acetone (50 ml). The mixture was then stirred into a large volume of water and the solution extracted with ether. Unreacted phenol was removed with cold 1N NaOH solution. The ether extract was dried over anhydrous sodium sulphate, filtered and concentrated under vacuum. The residual oil (8.0 g) without further purification, was hydrolyzed by 10% NaOH in $D_2O$ affording phenoxyacetic acid (4.5 g).

EXAMPLE XI

Phenoxy acetyl chloride

Phenoxyacetic acid (d5) was treated with 25 ml of thionyl chloride and stirred for 18 hours at room temperature. After the end of the reaction, the reaction mixture was concentrated under vacuum at 30° C. to provide phenoxyacetyl chloride (4.8 g).

EXAMPLE XII

To a solution of 2.16 g (10 mmole) of 6-aminopenicillanic acid in 70 ml of 4% potassium bicarbonate and 6 ml of acetone was added drop-wise, with stirring and ice-bath cooling, to a solution of 2.50 g (13.7 mmole) of phenyl acetylchloride in 30 ml of dry acetone over a period of 30 minutes. After stirring over a period of 45 minutes, at room temperature, the reaction mixture was concentrated and the residue was washed with 65 ml of benzene and 100 ml of ether. The organic layer was discarded and the aqueous solution was layered with 100 ml of ether. The contents were cooled in ice bath and acidified with 10% phosphoric acid to about pH 2.5. The aqueous layer was quickly extracted with two additional cold 50 ml portions of ether and the combined organic layer was washed with 50 ml of cold water, The aqueous layer was cooled in ice bath and neutralized with 1N potassium hydroxide to pH 7.00. The aqueous solution was concentrated under reduced pressure at room temperature to about 40 ml, To this solution was added acetone and allowed to crystallize at 0° C. The crystals were collected (1.75 g), dried and identified by $^1$H NMR.

EXAMPLE XIII

Preparation of Deuteriobenzyl-$D_5$-penicillin: (Penicillin-G)

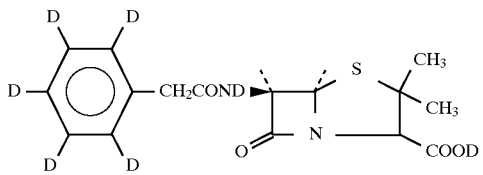

Phenylacetic-$d_5$-acid (2.72 g) was mixed with 25 ml of thionyl chloride in a 50 ml round bottom flask under a nitrogen atmosphere. The contents were stirred at room temperature for 24 hr. The excess thionyl chloride was removed under vacuum. No further purification was attempted.

Deutereophenylaceyl-$d_5$-chloride (1.76 g, 10 mmole) dissolved in 25 ml of dry acetone was added to an ice cold solution of 6-aminopenicillinic acid (4.3 g., 20 mmole) in 10 ml of 4% sodium bicarbonate and 8 ml of dry acetone. The addition was carried out over a period of 45 minutes. The reaction mixture was stirred for 30 minutes at 0°–4° C. After the completion of the reaction, the mixture was concentrated under aspiration. The aqueous solution was washed with benzene, and ether. The aqueous solution was layered with ether(50 ml) and acidified with 10% cold phosphoric acid to pH 2.5. The acidified reaction mixture was extracted with an additional two 50 ml portions of ether. The organic layer was separated and neutralized with 1N potassium hydroxide to pH 7.2. The aqueous layer was concentrated, mixed with acetone and the contents were allowed to stand at 0°–4° C. for crystallization. The crystals were collected, dried and characterized by $^1$H NMR.

EXAMPLE XIV

Preparation of Ampicillin-$d_5$

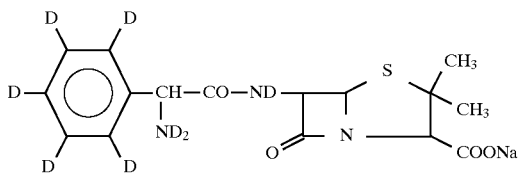

Preparation of D(-)t-BOC α-phenyl glycine

This derivative is prepared by a two part synthesis requiring first, the activation of the platinum oxide catalyst followed by the catalytic exchange of the amino acid. Activation of the catalyst was carried out by adding sodium borohydride 2.0 g) to a suspension of platinum oxide (0.5 g) in water (200 ml) which has been extensively degased. After the addition of the sodium borohydride was complete, the mixture was allowed to stir for an additional 30 min. Excess sodium borohydride was hydrolyzed by warming the reaction vessel to 70° C. After cooling, the water was carefully decanted and the activated catalyst (dark precipitate) was washed free of salts with small quantities of water and finally rinsed with 10 ml of $D_2O$. Reduced Adams catalyst (P°, 0.5 g) was placed in 30 ml of 99.9% $D_2O$ to which 5.0 g of the aminoacid was added. To the reaction vessel, Approximately 2.0 ml of 40% NaOD was added to the reaction vessel to permit complete dissolution of the amino acid. The mixture was then heated at 100° C. for four days. After cooling the reaction mixture was filtered. The aqueous solution was lyophilized. The reaction was repeated with fresh catalyst and $D_2O$. The solution was filtered and carefully neutralized with ice cooled dilute solution of HCl. The aqueous solution was extracted with chloroform, dried and concentrated. to give 4 g of the product. Without further purification, this material was used to couple with 1 6-aminopenicillinic acid.

Ethyl chloroformate (25 mmoles) was added to an ice cold solution of t-BOC α-phenyl glycine (20 mmoles), and triethylamine (25 mmoles) in dry acetone(250 ml). The mixture was stirred at 0° C. for 10 minutes. Then the suspension was cooled to −50° C. and stirred vigorously during addition as rapidly as possible of an ice-cold solution of 6-aminopenicillinic acid (20 mmole) in 3% sodium bicarbonate. The reaction mixture was stirred at 0°–4° C. for one hour. The reaction mixture was allowed to reach room temperature over a period of 30 minutes. Then the reaction mixture was concemrated under vacuum and then washed with ether (3×100 ml). The aqueous layer was acidified to pH 2 using ice cold dilute HCl and quickly extracted with ether. Then the ether layer was treated with 10 ml of trifluoroacetic acid and stirred at room temperature over night. The reaction mixture was concentrated under vacuum. The residue was dissolved in 50 ml water and neuteralized with 1N sodium hydroxide to pH 7.2, acetone was added and allowed to crystallize at 0° C. The solution filtered and dried to provide 1.1 g of the product.

EXAMPLE XV
Synthesis of Methicilline-d3

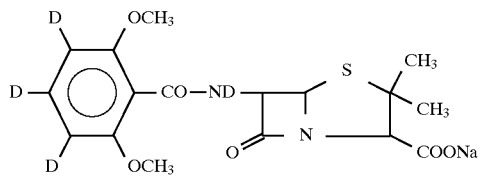

Deuterated 2,6-Dimethyl benzoic acid was prepared by treating 5 g of 2,6-dimethyl benzoic acid with 25 ml solution of trifluoroacetic anhydride and $D_2O$ (2:1). The mixture was heated at 100° C. for 24 hours Then after cooling the reaction mixture was concentrated under vacuum to remove trifluoroacetic acid. Then the residue was diluted with 50 ml water to provide a solid material which was filtered and characterised by $^1H$ NMR.

Deuterated 2,6-Dimethyl benzoic acid (2 g) was treated with 25 ml of thionyl chloride and stirred for 24 hour. The reaction mixture was concentrated under vacuum to provide an oil (2.2 g).

A solution of 2,6-dimethoxy benzoyl chloride (2.2 g) in dry alcohol free chloroform (30 ml) was added with stirring 20 min. to an ice-cold suspension of 6-aninopenicillinic acid (2 g) in chloroform (30 ml) and triethyl amine (2.57 ml). The mixture was stirred at room temperature for 1 hr and then treated with continued stirring with 1N hydrochloric acid to give an aqueous phase of pH 1. The organic layer was separated, washed with water, and neutralized with sodium bicarbonate to pH 7. The aqueous solution was separated, washed with ether and concentrated to 20 ml. Acetone was added and allowed to crystallize at 0° C. The solid was filtered and dried to provide 0.6 g of the product.

EXAMPLE XVI
General method of preparation of deuterated drugs of heterocyclic and aromatic nature The pharmaceutical compound (10 mmole) was treated with a solution of (25 ml) trifluoroacetic anhydride and $D_2O$ (2:1) and placed in a pressure vessel. The contents were heated at 80° C. for 48 hour.

Workup for neutral compounds

The reaction mixture was concentrated under vacuum to remove trifluoroacetic acid and extracted with chloroform, washed with water, dried and concentrated.

Workup for acid derivatives

The reaction mixture was concentrated and diluted with water. The solid was separated, filtered, and dried. If no solid separated, the mixture was extracted with chloroform, dried, concentrated and purified by chromatography over silica gel.

Workup for basic compounds

The reaction mixture was concentrated and neutralized to pH 7 and extracted with chloroform, dried, concentrated and purified by column chromatography.

Using this method the following compounds were prepared.
1. Verapamil
2. Isoniazid
3. Chloroquine
4. Tamoxifen
5. Ibuprofen
6. Propranolol
7. Glyburide
8. Cimietidine
9. Diazepam
10. Omeprazole Antibiotic Testing Antibiotic testing was carried out using disc diffusion and tube dilution methods following NCCLS (National Committee for Clinical Laboratory Standards) methodology with several strains of bacteria. The results are shown in FIGS. 18 to 22.

Figure 18:
FIG. 18 shows a graph of comparisons of unmodified and deuterated ceftazidine in tube dilution studies in term of effective concentration for inhibition of bacterial strain.

FIG. 18—Ceftazidime tube dilution

For *Streptococcus pyogenes* and *Staphylococcus aureus* the zones of inhibition were the same for control and modified drug. For Enterobacter aerogenes the concentration of modified drug necessary for growth inhibition was less than that of the control drug. For *Pseudomoaas aeruginosa*, however, concentration of modified drug necessary for growth inhibition was greater than that of the control drug. These results suggest that the modified ceftazidime has altered properties compared to the native drug. Namely, there is differential sensitivity of the indicated bacteria to the two drugs.

Figure 19:
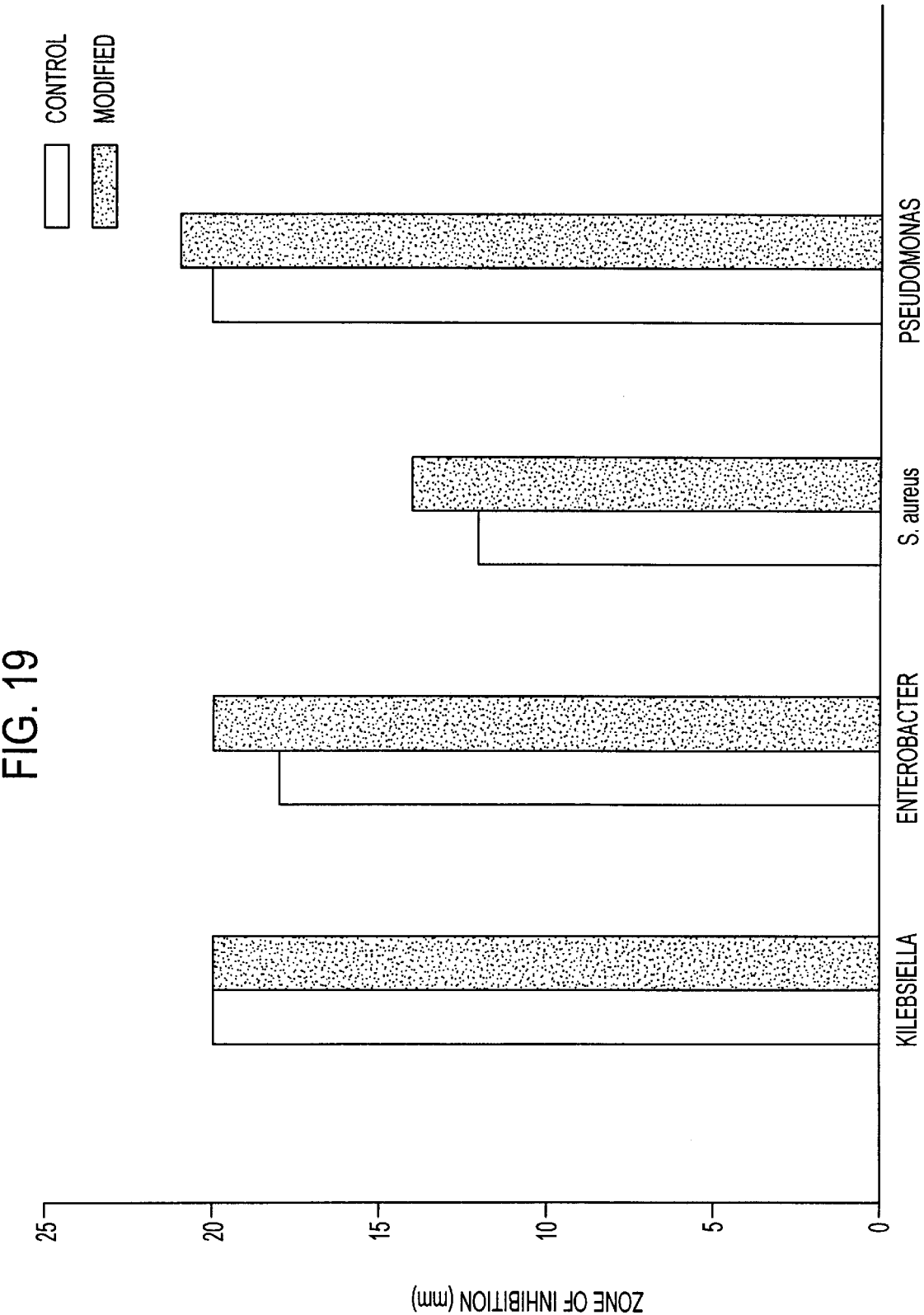
FIG. 19 shows a graph of comparison of unmodified and deuterated ceftazidine in zonal inhibition studies of bacterial strain.

FIG. 19—Ceftazidime disc diffusion

For *Klebsiella pneumoniae* the areas of inhibition were similar for control and modified drug. For Enterobater aerogenes and *Staphylococcus aureus* the zones of inhibition were greater for modified compared to control drug. For *Pseudomonas aeruginosa* the zone of inhibition for modified ceftazidime was marginally greater than for control ceftazidime. This was probably not significant, however. These results again show differential sensitivity of the indicated bacteria for control and modified ceftazidime. Thus, the modified drug appear to have different properties than the native drug. A non-specific toxicity effect or dilutional error is ruled out by the fact that in both disc diffusion and tube dilution some bacteria show equivalent sensitivity to both drugs.

Figure 20:
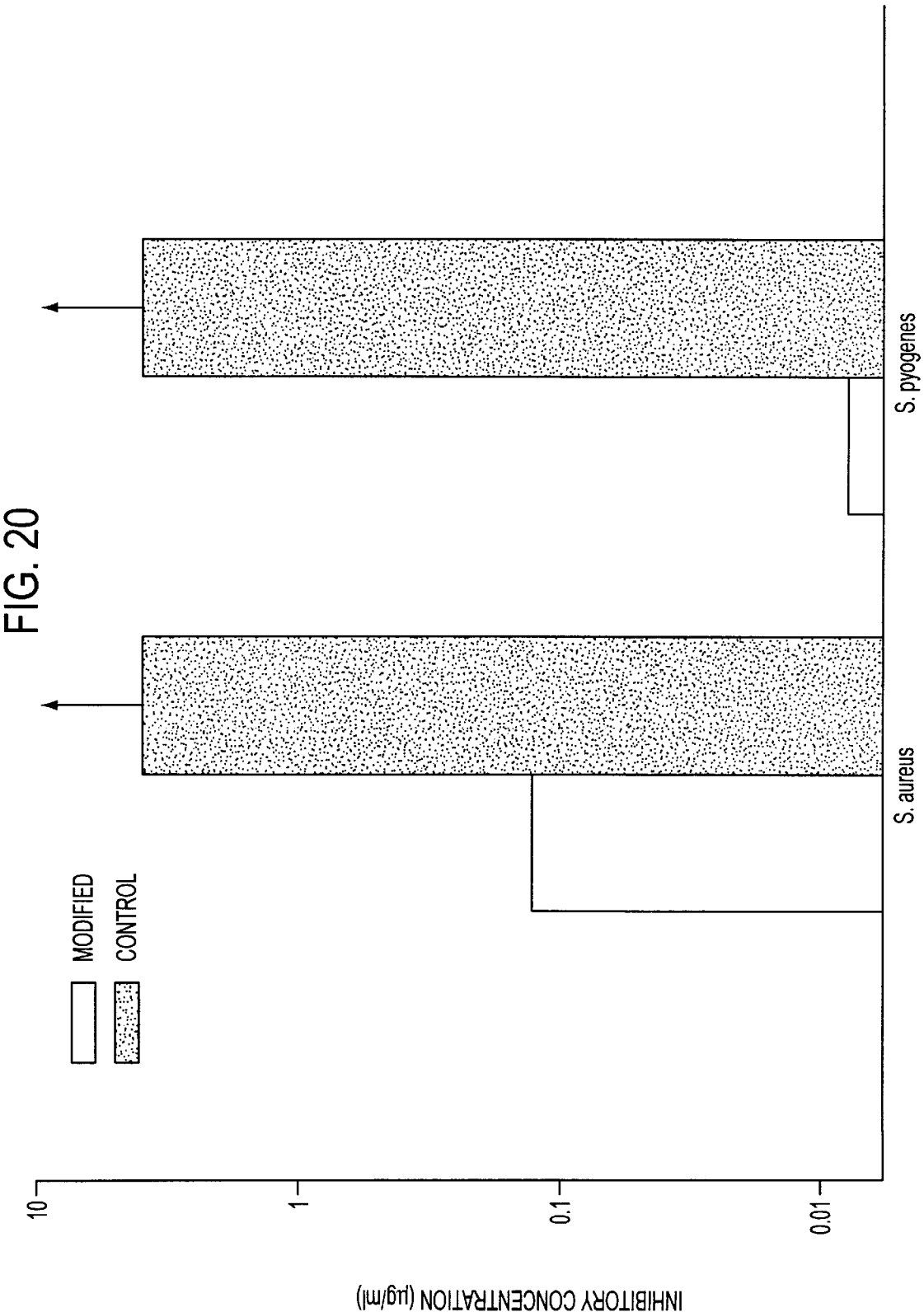
FIG. 20 shows a bar graph of comparisons of penicillins on bacterial growth (tube dilution)

FIG. 20—Penicillin V tube dilution

For *Staphylococcus aureus* and *Streptococcus pyogenes* the concentration of modified drug necessary to inhibit growth was substantially less compared to control drug. This indicates that the modification increase the potency of the native drug.

Figure 21:
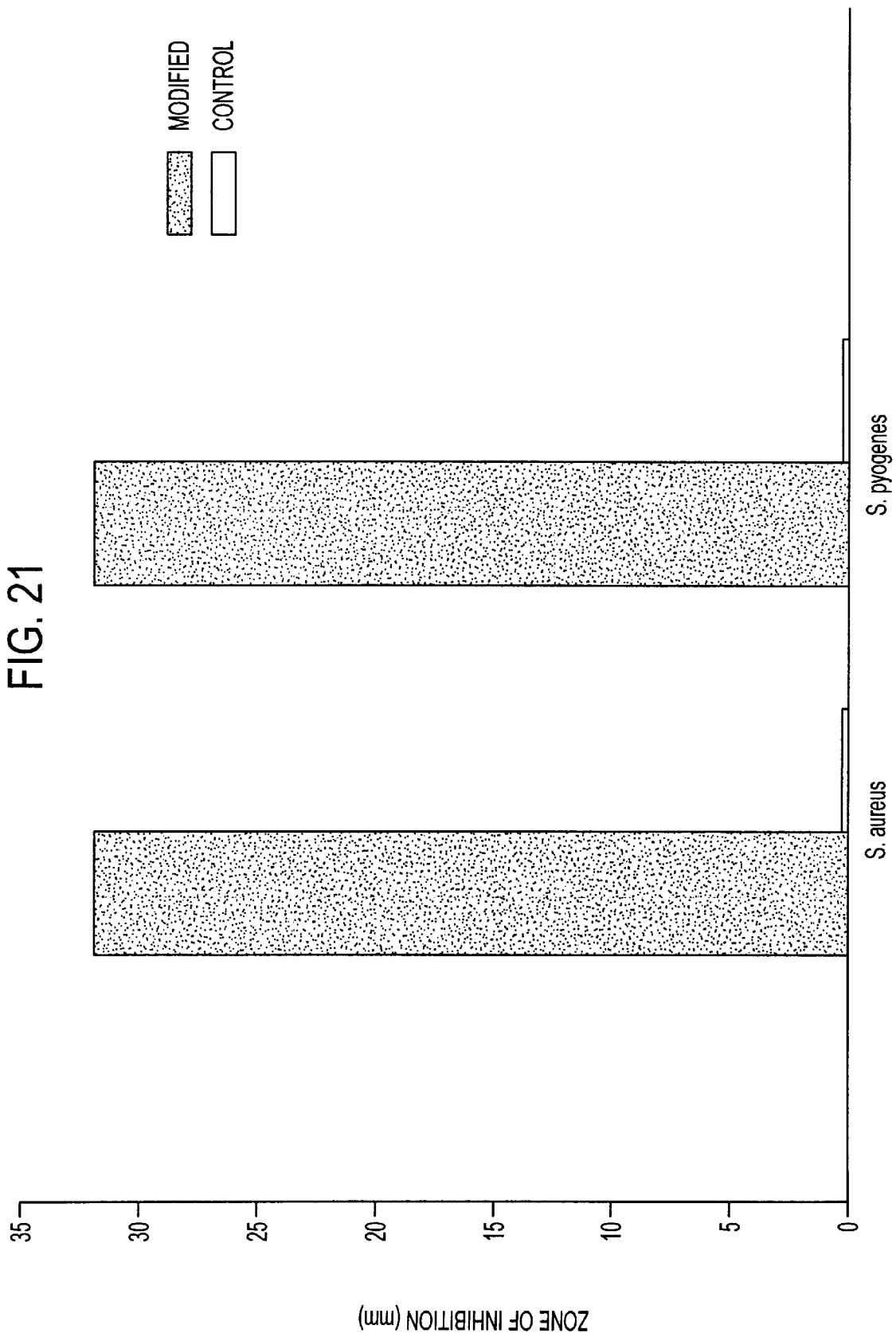
FIG. 21 shows a bar graph of the effect of penicillin on bacterial growth (disk diffusion)
Figure 22:
FIG. 22 shows a bar graph of the effect of penicillin on the growth of specific bacterial strains.

FIGS. 21 & 22—Penicillin V disc diffusion

For *Staphylococcus aureus* and *Streptococcus pyogenes* and *Streptococcus faecalis* the zones of inhibition were greater for modified (test) compared to control drug. This indicates that the modification increased the potency of the native drug and, in fact introduced a novel property (effectiveness against *S. aureus*) into it.

In the case of both ceftazidime and Penicillin V, the modified drugs may find clinical utility against currently resistant bacterial strains and by providing an expanded spectrum of activity.

The following is a list of strains and their ATCC number that were used in these studies:

| ATCC# | Bacteria |
| --- | --- |
| 14053 | *Candida Allbicans* |
| 13048 | *Enterobacter aerogenes* |
| 25922 | *Escherichia Coli* |
| 13883 | *Klebsiella Pneumoniae* |
| 13315 | *Proteus Vulgaris* |
| 27853 | *Pseudomonas Aeruginosa* |
| 25923 | *Staphylococcus Aureus* |
| 19433 | *Streptococcus faecalis* |
| 29212 | *Streptococcus faecalis* |
| 19615 | *Streptococcus Pyogenes* |

In a still further aspect of the invention, the following work was carried out to determine the effect of deuteration on activity of penicillin V.

Figure 24:
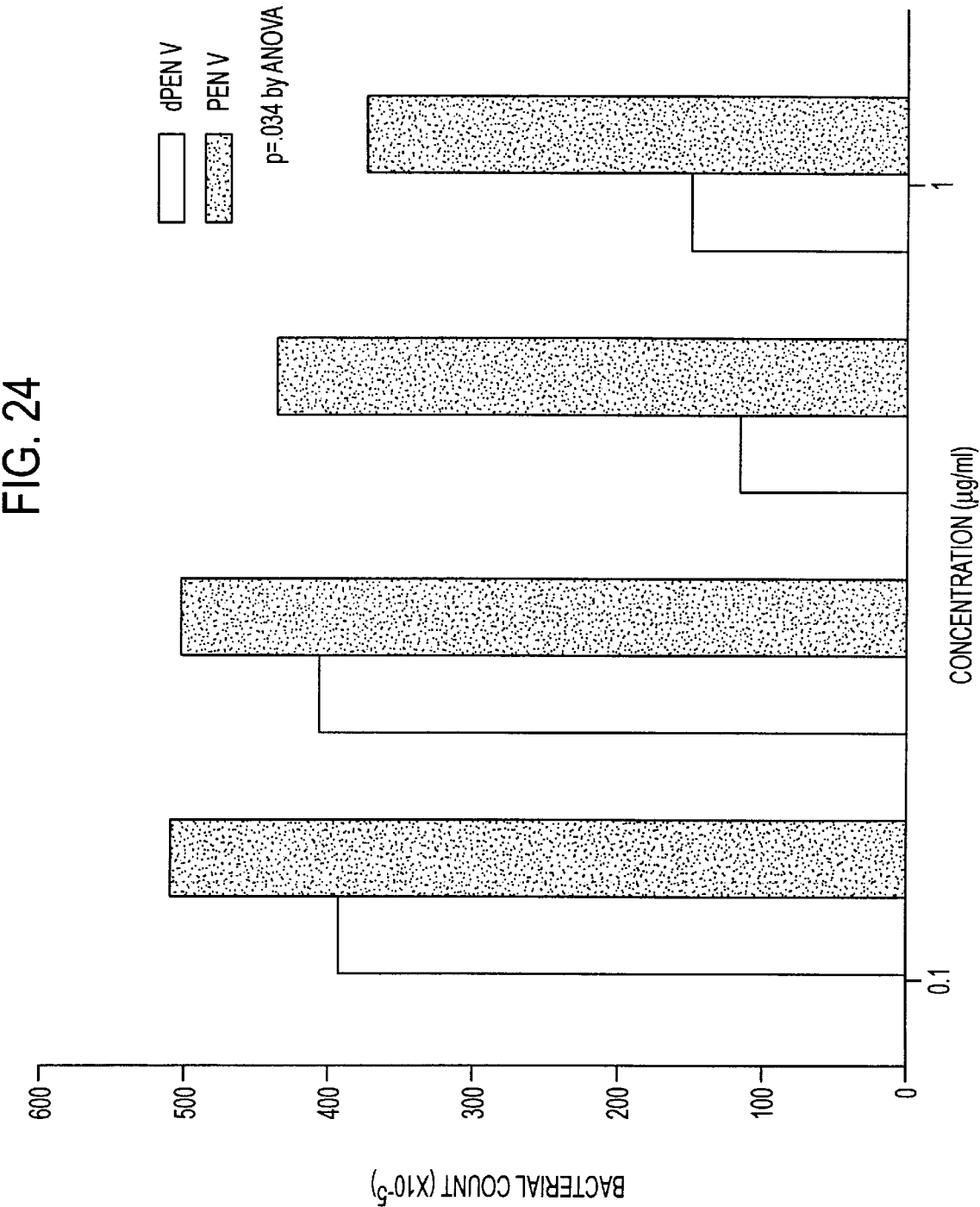
FIG. 24 shows a bar graph of the effect of modified and unmodified penicillin V on S. aureus at different concentrations.

Deuteration and native penicillin V were compared for bactericidal activity by modified tube dilution and zonal inhibition method A) Tube dilution Two-fold serial dilutions of both penicillin were made in ml aliquots of Mueller-Hinton broth. One ml of broth solution containing $1 \times 10^6$ bacteria per mil was then added to each tube. Tubes were then incubated for 24 hours at 37° C. and bacteria subsequently counted microscopically. Bacteria used were *Staphylococcus aureus* (ATCC 25923) and *Streptococcus faecalis* (ATCC 29212). Bacterial counts were compared between concentrations and drugs within bacterial cultures using two-way ANOVA. Results of the analysis are shown in FIG. 24. ANOVA resulted in a significant (p=0.034) drug effect but no dose effect (p=0.11) at the concentration used (range 1.024 to 0.128 µg/ml).

B) Zonal inhibition

Figure 23:
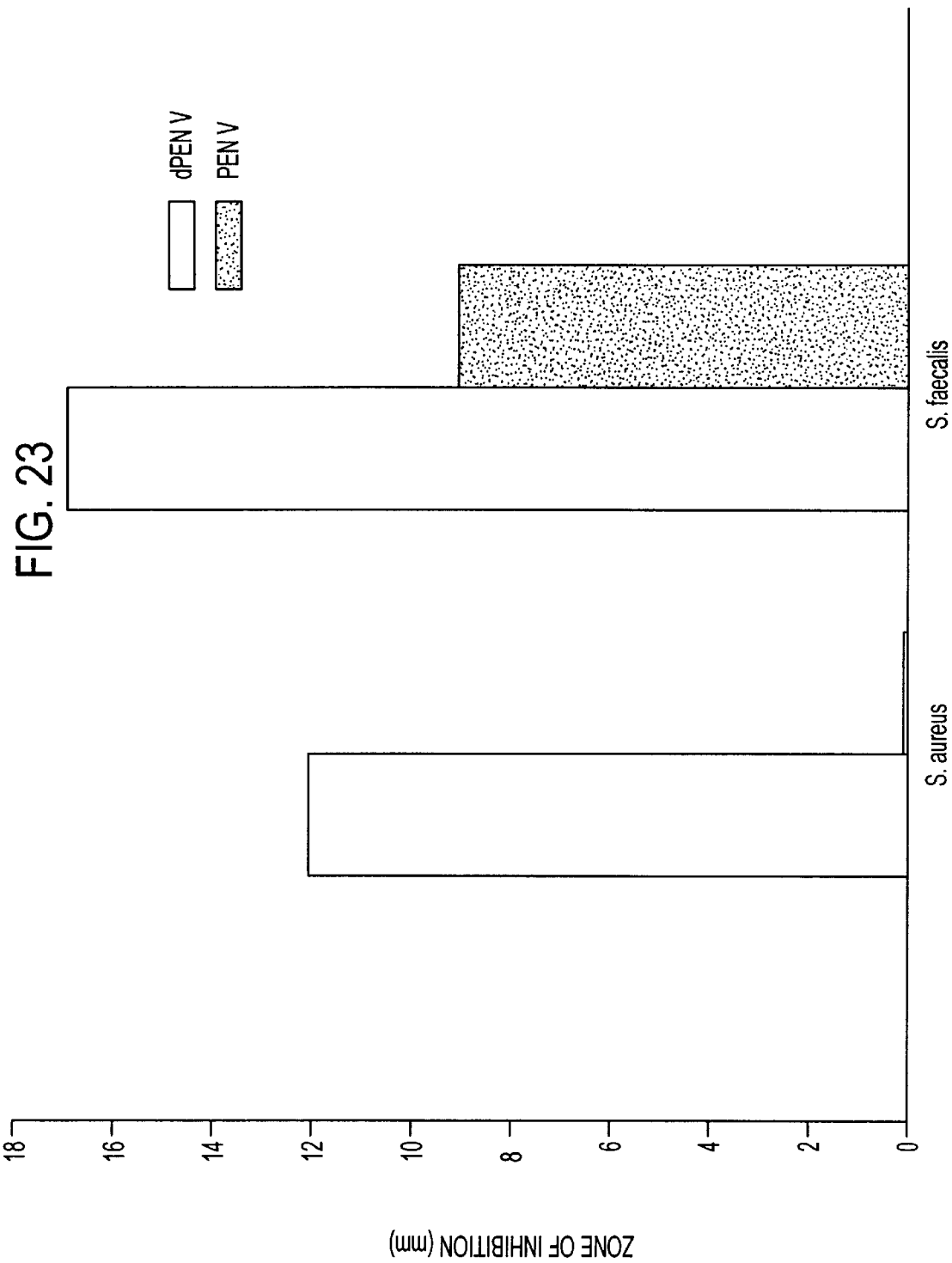
FIG. 23 shows a bar graph of the effect on modified and unmodified penicillin V on two types of bacteria as measured by zonal inhibition.

Penicillin V. or deuterated penicillin V disks were prepared by allowing 0.1 ml of a 1 mg/ml solution of the respective drugs to absorb into filter paper disks. After drying the disks were placed onto Mueller-Hinton agar plates seeded with either *Staphylococcus aureus* (ATCC 25923) or *Streptococcus faecalis* (ATCC 29212). The resulting plates were incubated for 24 hours at 37° C. and zones of inhibition around the disks were measured. Results are graphically depicted in FIG. 23.

Deuteration of penicillin V results in an unexpected increase in potency of the drug relative to the specific bacteria of reference (as seen in the zonal inhibition experiments). In addition, an expanded spectrum of activity is imparted to the drug as seen in both sets of experiments. Deuteration of Penicillin V, and probably other antibiotics, may enhance their potency and alter (expand) their spectrum of activity. This expanded spectrum of activity may be due to decreased susceptibility of the deuterated drug to bacterial breakdown or it may be due to altered physicochemical properties (e.g. altered hydrophobicity). In addition , in vivo, the deuterated penicillin V may also be less susceptible to usual metabolic and elimination pathways, thus increasing its duration of action (half-life).

Penicillin V(d5) was prepared using the following procedure:

Step 1

Preparation of Phenoxyacetic acid(d6)

Phenol ($d_6$) was treated with ethyl chloroacetate in the presence of anhydrous potassium carbonate to provide ethyl phenoxy acetate which was further converted to phenoxyacetic acid by treatment with a solution of sodium in Methanol –d4.

Step 2

Preparation of Penicillin V($d_5$)

6-Aminopenicillanic acid is converted into trimethyl silyl 6-aminopenicillanate by treatment with Hexamethyldisilazane. This derivative was treated with phenoxy acetic acid, prepared above in Step 1, in the presence of N-hydroxysuccinimide and dicyclohexylcarbodiimide (DCC). Further treatment with ethanol and water to remove the trimethylsilyl protecting group followed by crystallization from acetone and water ($D_2O$) provided the required Penicillin V($d_5$).

Figure 25:
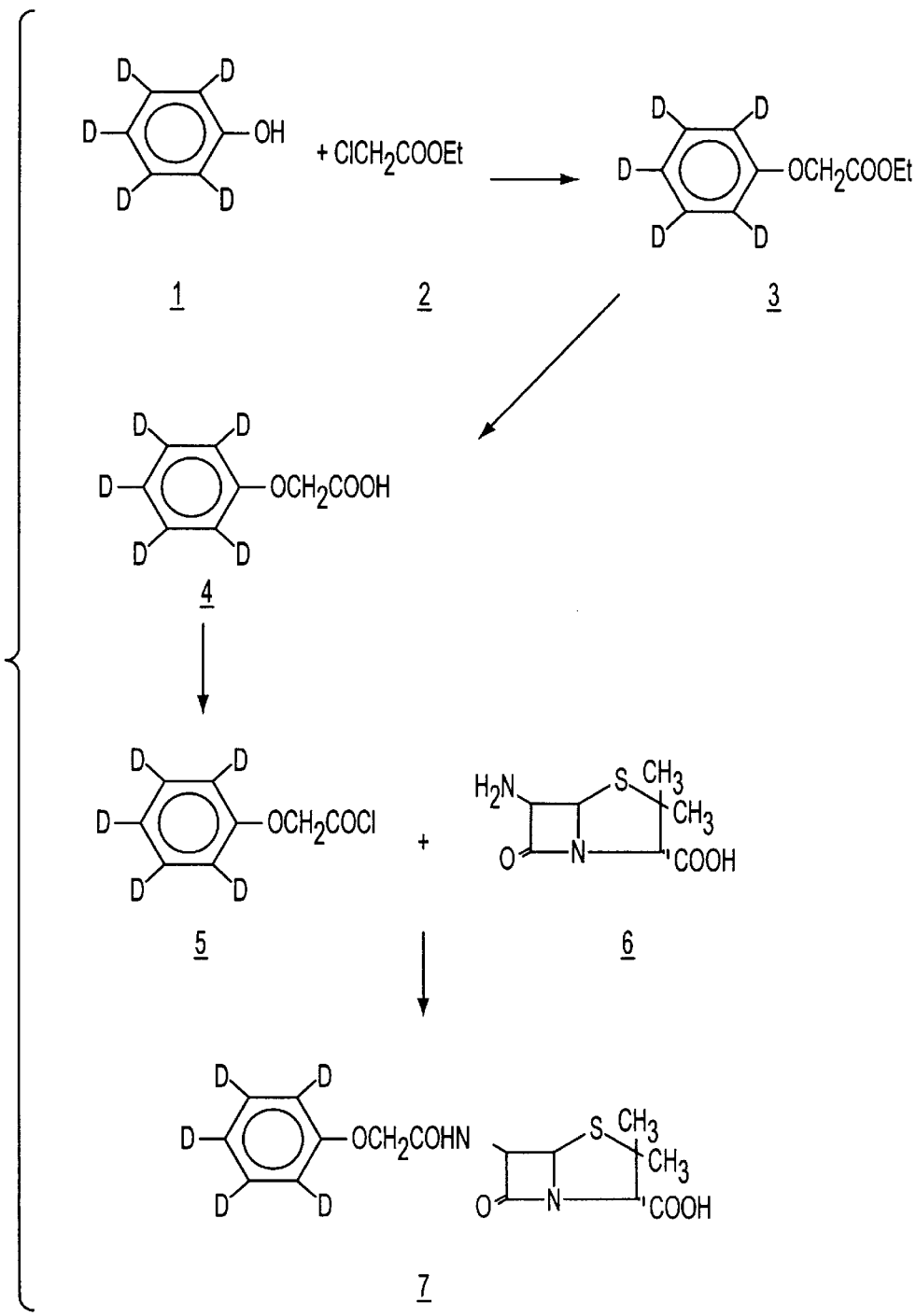
FIG. 25 shows a diagram showing the reaction sequence for preparation of a modified penicillin.

The synthesis of penicillin V is shown in FIG. 25. Phenol($d_5$) 1 was treated with ethyl chloroacetate 2 to provide 2-Phenoxy($d_5$)ethyl acetate 3 which was further treated with NaOD to get 2-Phenoxy($d_5$)acetic acid.4 This compound was converted into the acid chloride 5 by treatment with thionyl chloride. The acid chloride derivative 5 was then coupled with 6-aminopenicillanic acid 6 to obtain the desired product.7.

Preparation of Deuterated Verapamil

Method: Deuteration of Verapamil

Verapamil hydrochloride was added to a solution of 25% deuterated sulfuric acid in deuterated water (v/v) and deuterated methanol. The solution was stirred for 140 hours at 90° C. The pH was adjusted to 12.0 and the mixture extracted with ethyl acetate. The combined ethyl acetate extracts were washed with water, dried over magnesium sulfate and evaporated to yield a viscous oil. This oil was dissolved in ether and ethereal hydrochloride was added to precipitate the hydrochloride salt. The salt was collected by filtration and crystallized from ethyl acetate to obtain deuterated verapamil as a white solid.

Testing of Antibiotic Spectrum and Potency

Antibiotic testing was carried using disc diffusion and tube dilution methods following NCCLS (National Committee for Clinical Laboratory Standards) methodology.

Deuterated methicillin, ceftazidime, and penicillin V, prepared as previously described, were tested in tube dilution assays, disk diffusion assays, in dose-response studies, and vehicle-effect studies.

Figure 26:
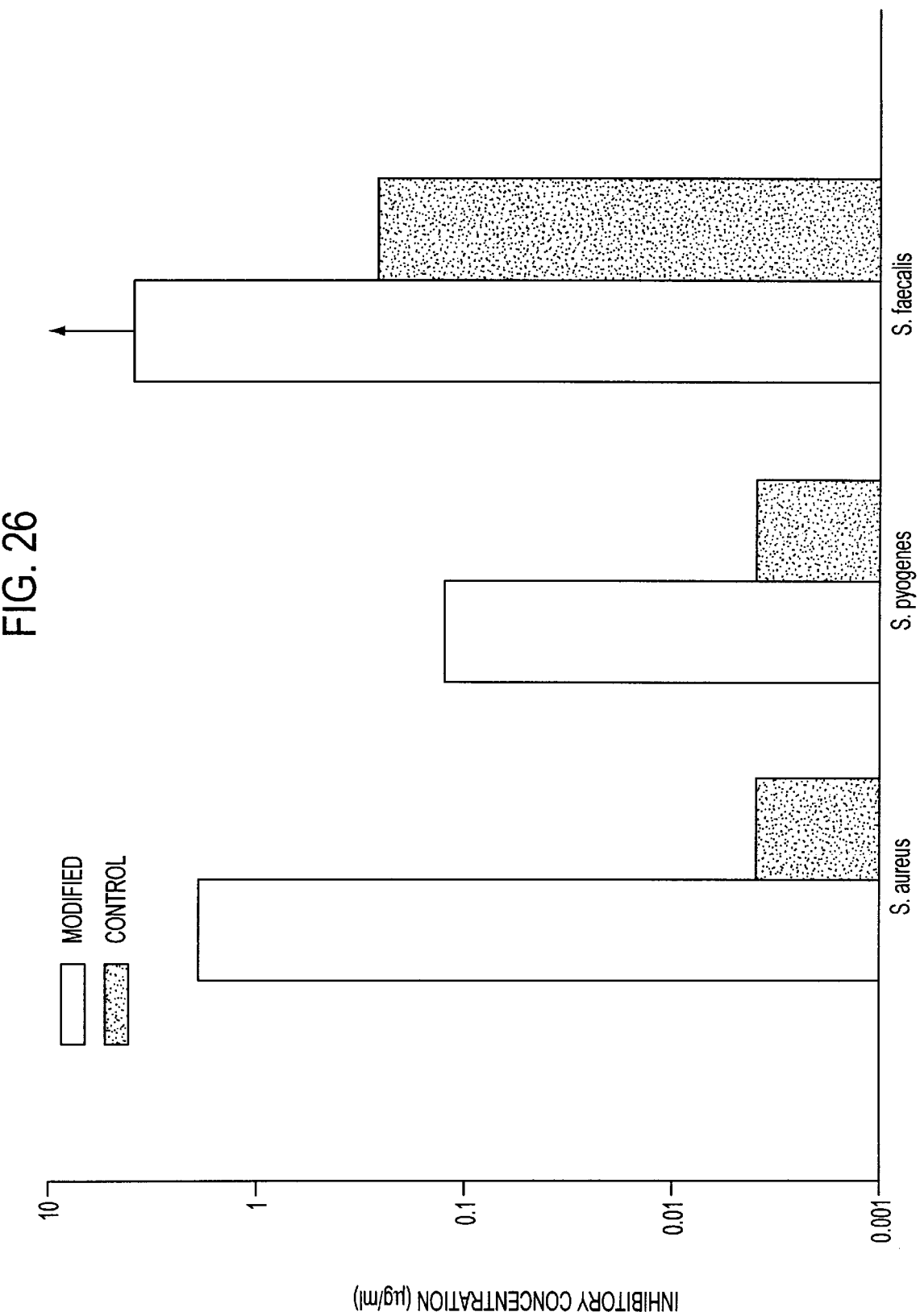
FIG. 26 shows the results of a control and test methicillin tube dilution experiment.

For *Staphylococcus aureus, Streptococcus pyogenes* and *Streptoccus faecalis* the concentration of methicillin necessary to inhibit growth was less for control compared to modified drug (FIG. 26). This indicates that the modification decreased potency in this instance. Nevertheless, this shows that the reaction is specific and not due to chemical contaminants.

Figure 27:
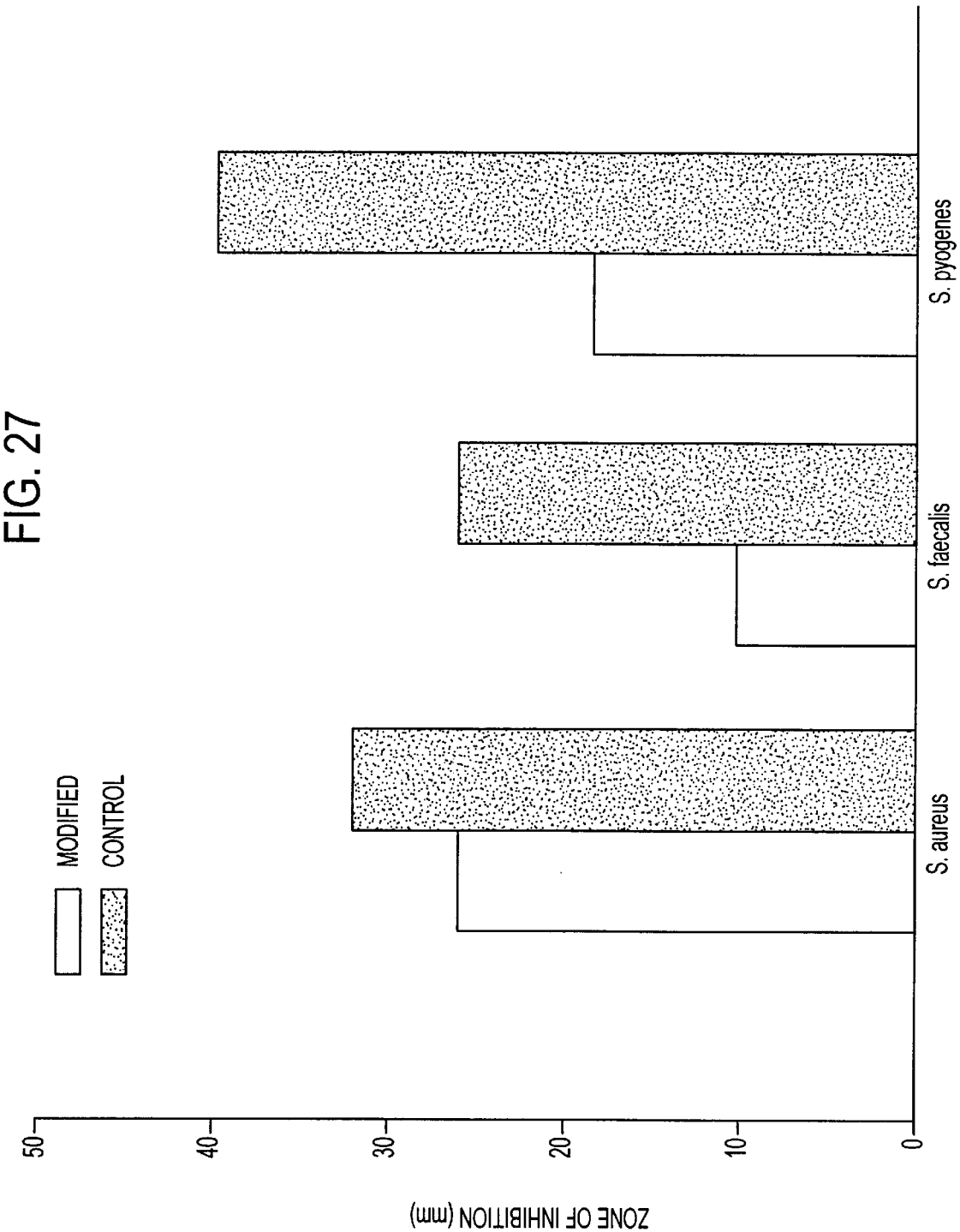
FIG. 27 shows the results of a control and test methicillin disc diffusion experiment.

For *Staphylococcus aureus, Streptococcus pyogenes* and *Streptococcus faecalis* the zone of inhibition were less for modified compared to control drug (FIG. 27). This indicates that the modification decreased the potency of the native drug.

Figure 28:
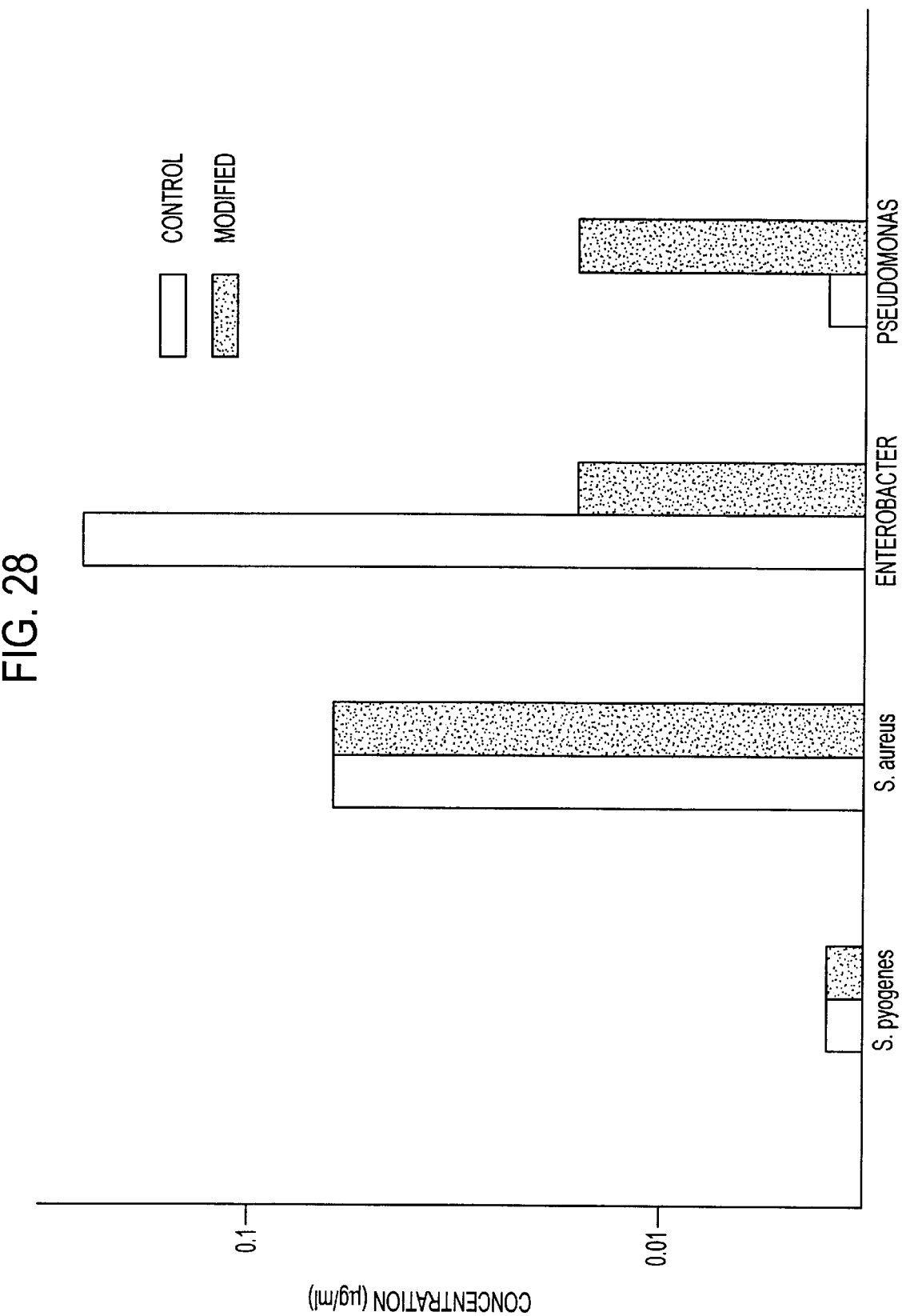
FIG. 28 shows the results of a control and test ceftazidime tube dilution experiment.

For *Streptococcus pyogenes* and *Staphylococcus aureus* the zones of inhibition were the same of control and modified drug. For *Enterobacter aerogenes* the concentration of modified drug necessary for growth inhibition was less than that of the control drug (FIG. 28). For *Pseudomonas aeruginosa*, however, concentration of modified drug necessary for growth inhibition was greater than that of the control drug. These results indicate that the modified ceftazidime has altered properties compared to the native drug. Namely, there is differential sensitivity of the indicated bacteria to the two drugs.

Figure 29:
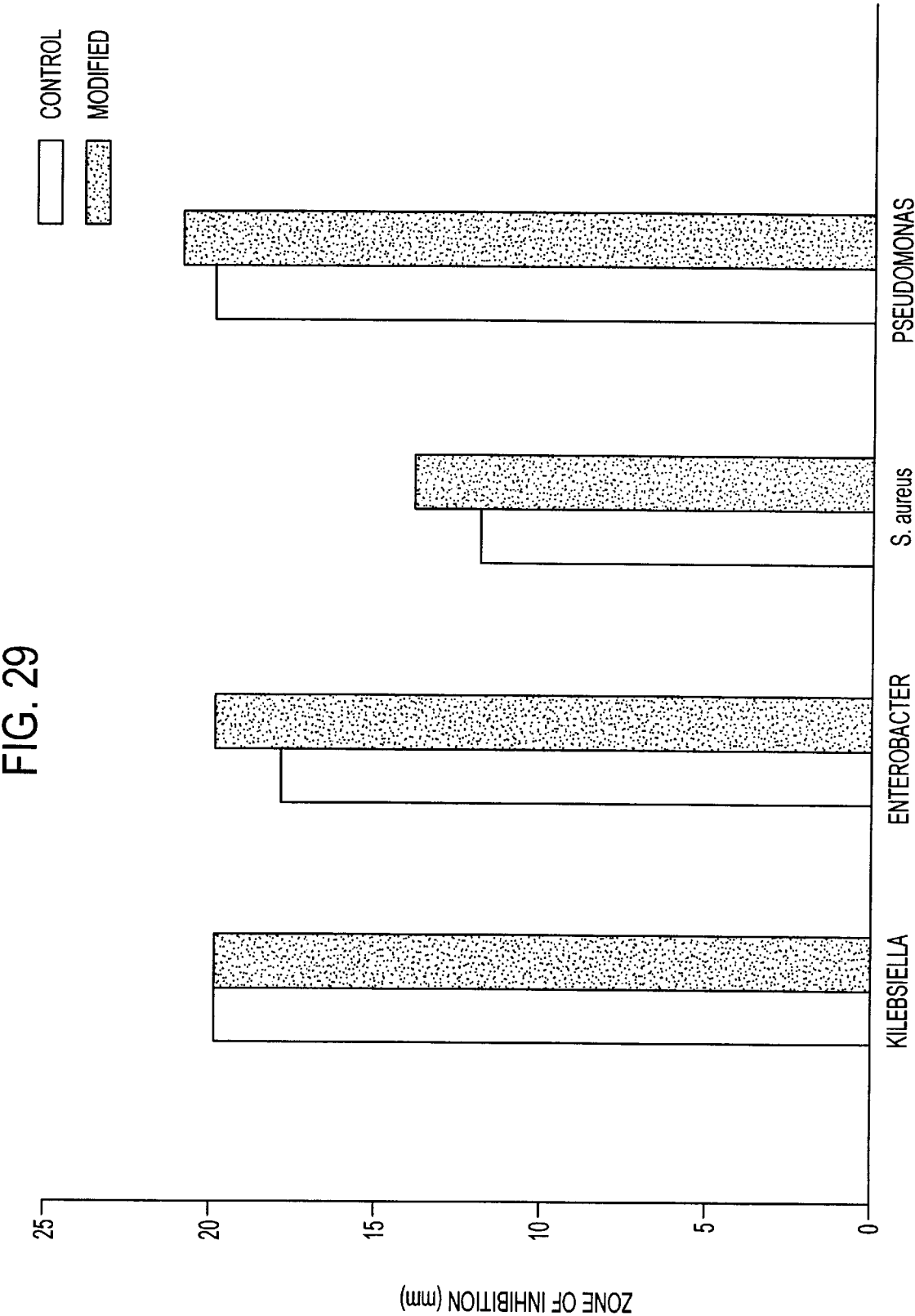
FIG. 29 shows the results of a control and test ceftazidime tube dilution experiment.

For *Klebsiella pneumonia* the areas of inhibition were similar for control and modified drug. For *Enterobacter aerogenes* and *Staphylococcus aureus* the zones of inhibition were slightly greater for modified compared to control drug. For *Pseudomonas aeruginosa* the zone of inhibition for modified ceftazidime was marginally greater than for control ceftazidime (FIG. 29).

Figure 30:
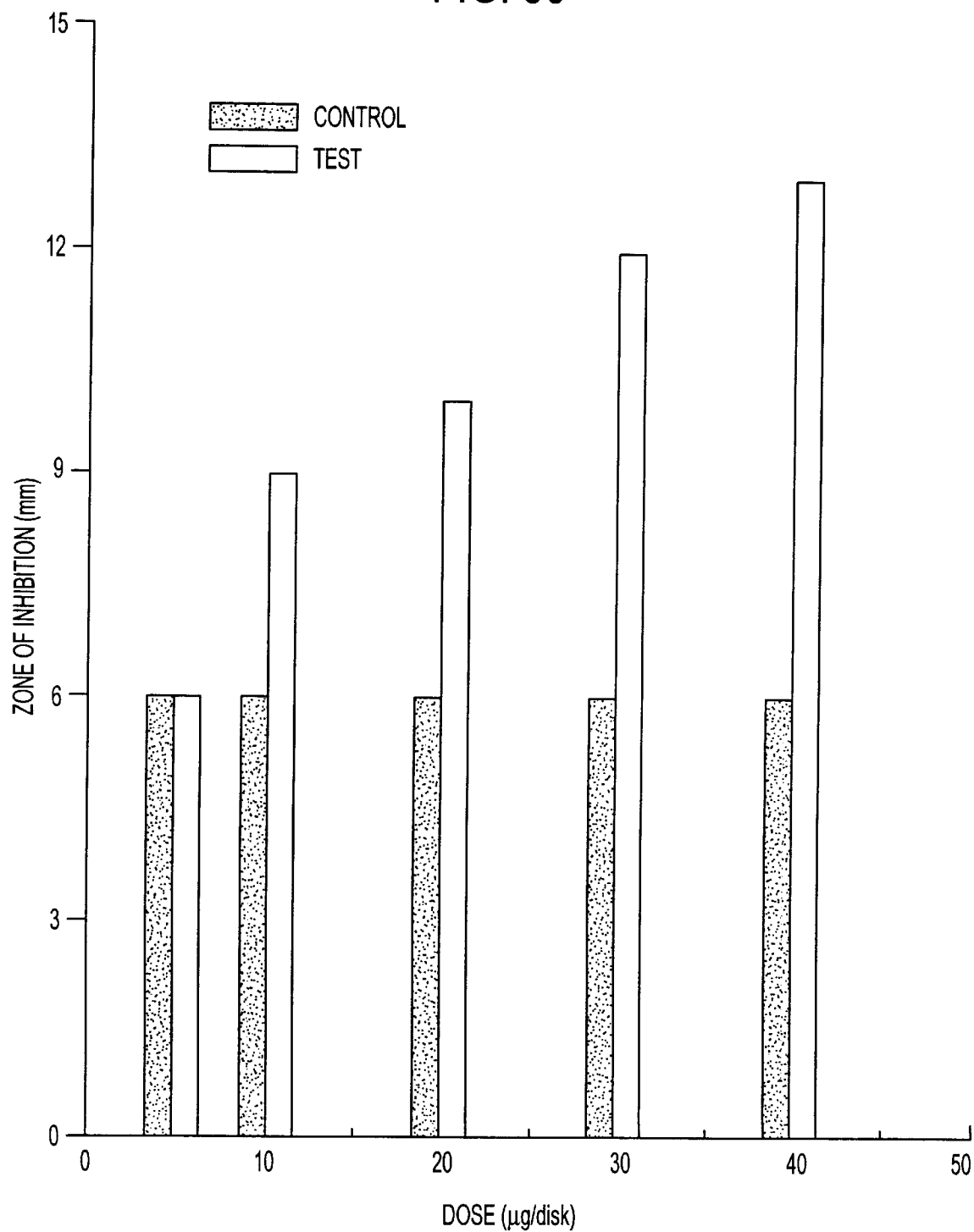
FIG. 30 shows the results of a control and test penicillin V dose-response experiment.

A dose-response study for penicillin V using *S. aureus* was conducted (FIG. 30). This result shows a dose dependency in bacteriocidal activity. At low doses neither version is effective, while at high dose, the modified (test) drug began to show effect. These conditions used a higher inoculum (100 fold) than previous studies.

Figure 31:
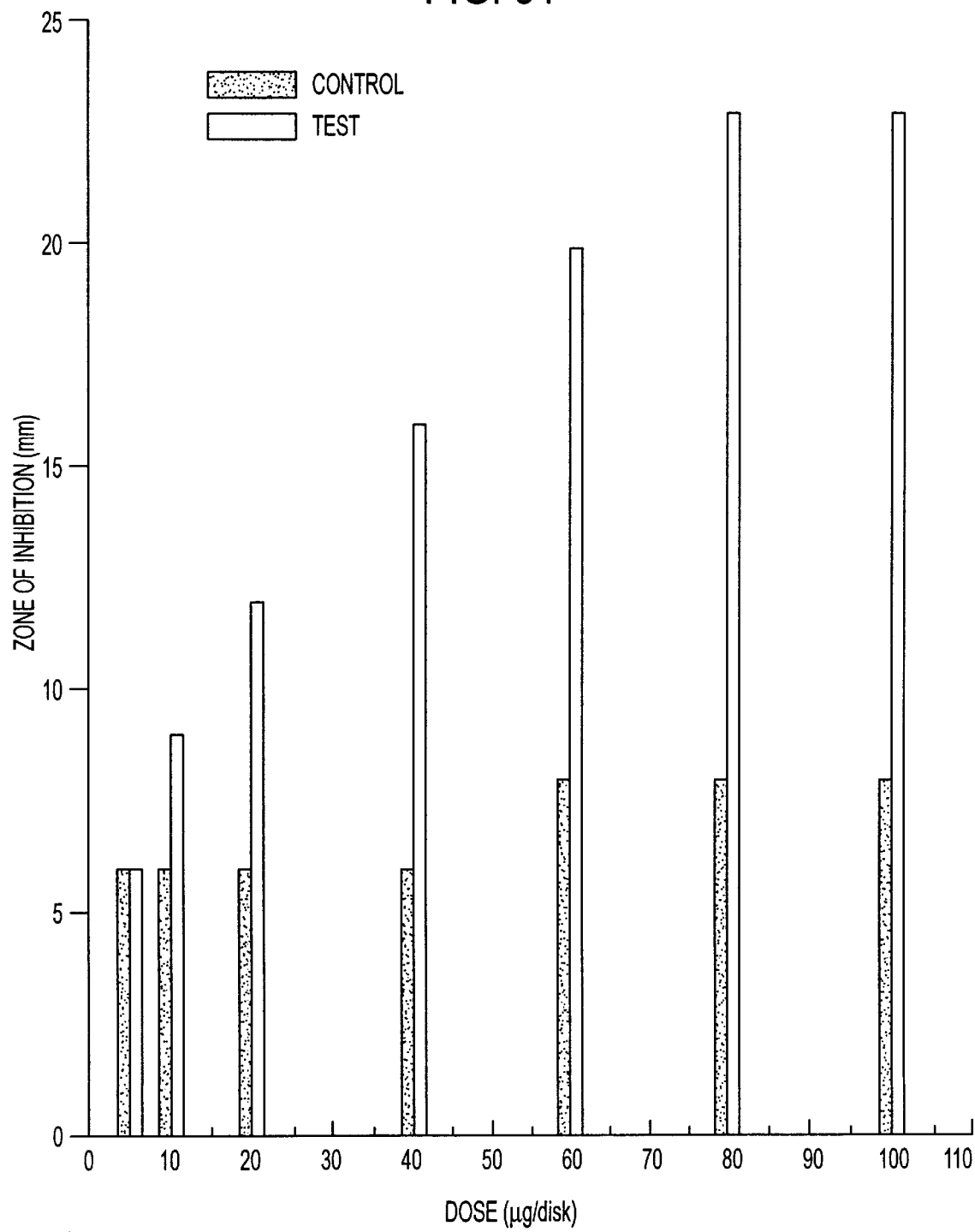
FIG. 31 shows the results of a control and test penicillin V dose-response experiment.

A experiment similar to that above was performed except that the dose range was larger. Again, the modified drug was effective at higher doses while the control penicillin V was ineffective (FIG. 31).

Figure 32:
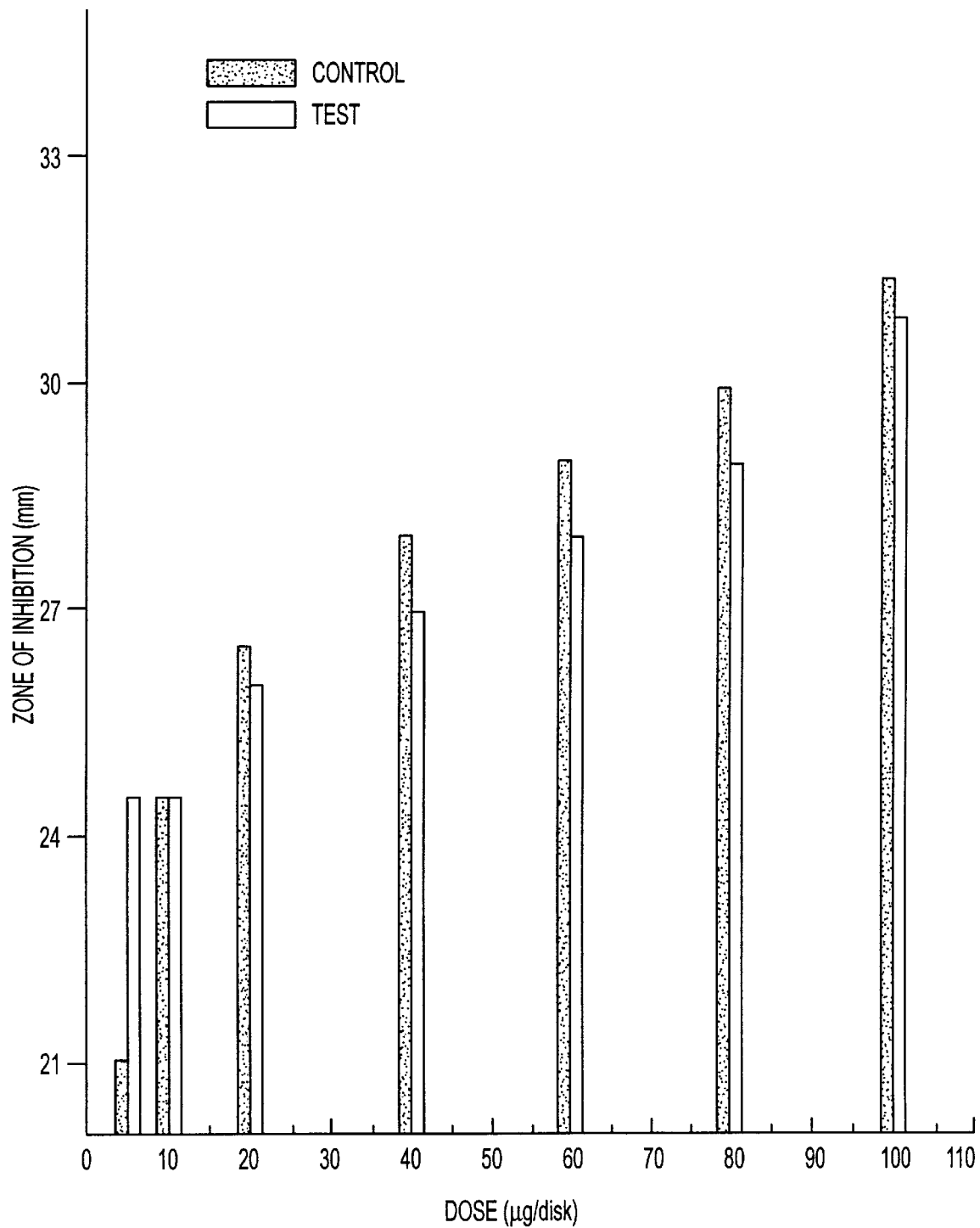
FIG. 32 show the results of a control and test ceftazidime dose-response experiment.

A similar dose-response relationship was tested for ceftazidime (FIG. 32). As can be seen, at the lowest concentration there was a difference between the modified and control drugs (modified more effective). At higher doses these difference were eliminated.

Figure 33:
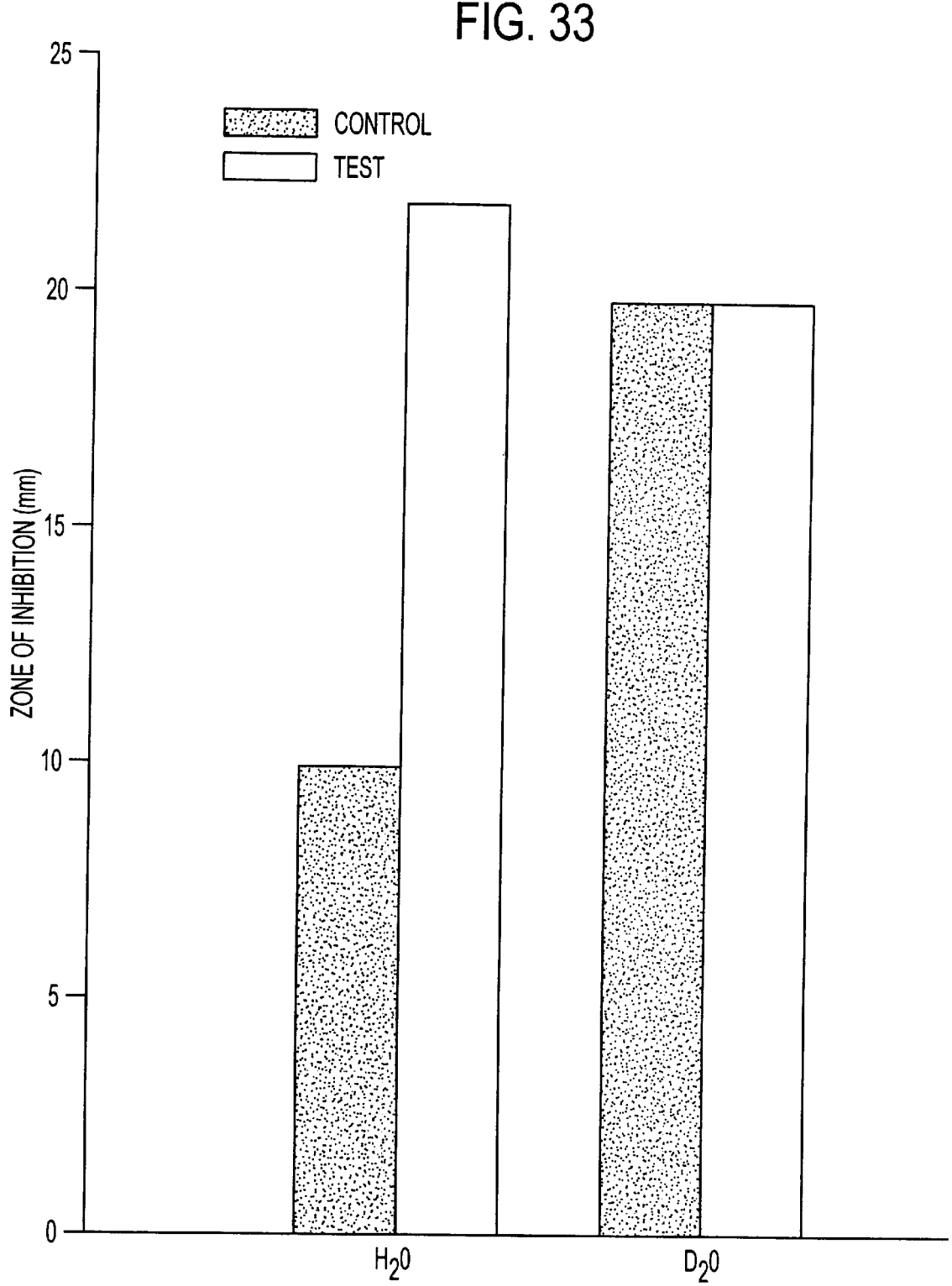
FIG. 33 shows the results of solvent on control and test ceftazidime activity.

The effect of solvent on ceftazidime activity was tested to confirm that dissolving ceftazidime in $D_2O$ could alter its efficacy. We therefore dissolved control and modified ceftazidime in water of $D_2O$ and tested it effect on *S. pyogenes* (FIG. 33). As can be seen, the modified drug was more effective than control drug when dissolved in water. When dissolved in $D_2O$ however, the control ceftazidime had enhance activity. Thus, our findings underscore the unique importance of isotopes.

Figure 34:
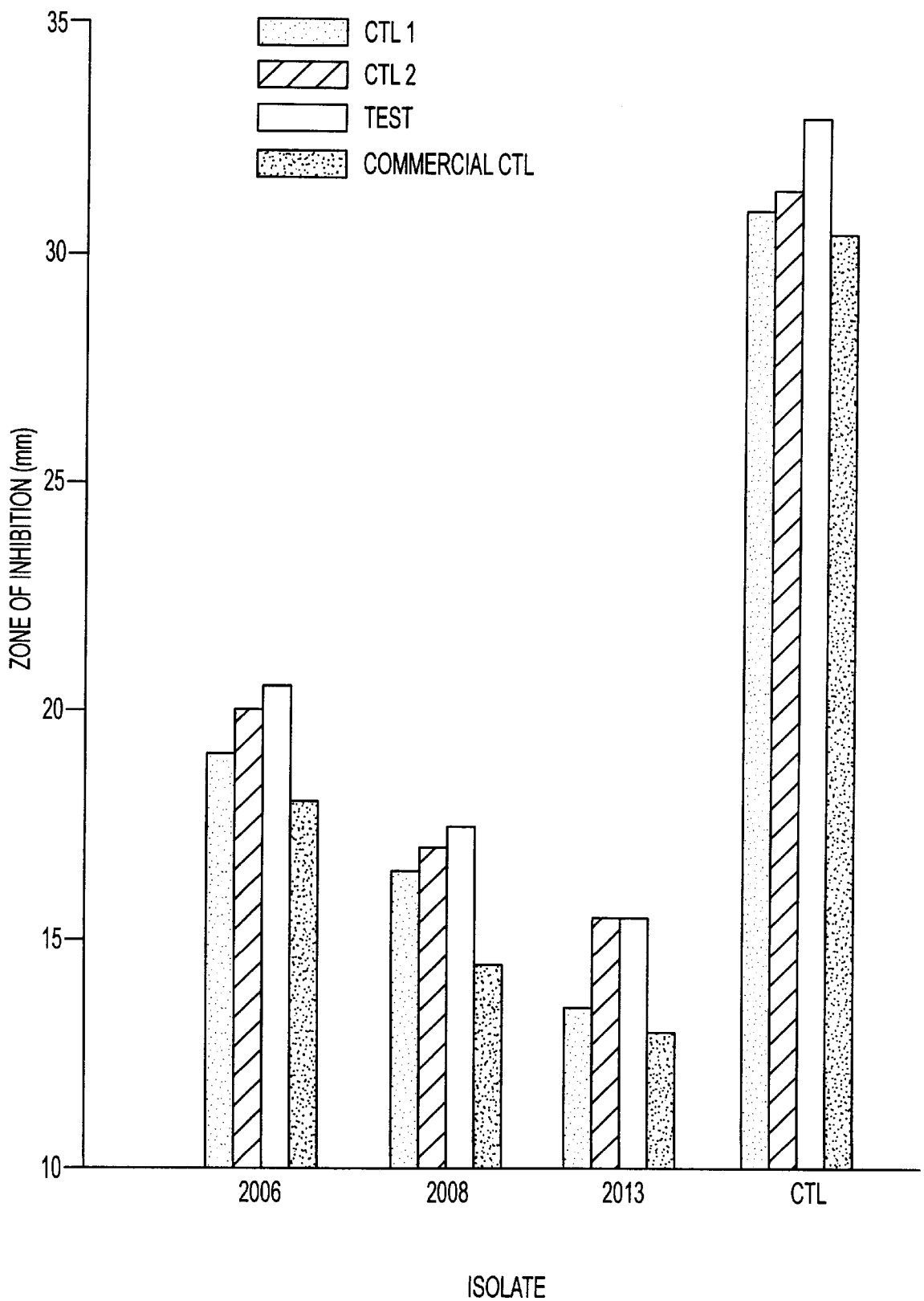
FIG. 34 shows the effect of control and test penicillin V on clinical isolates.
Figure 35:
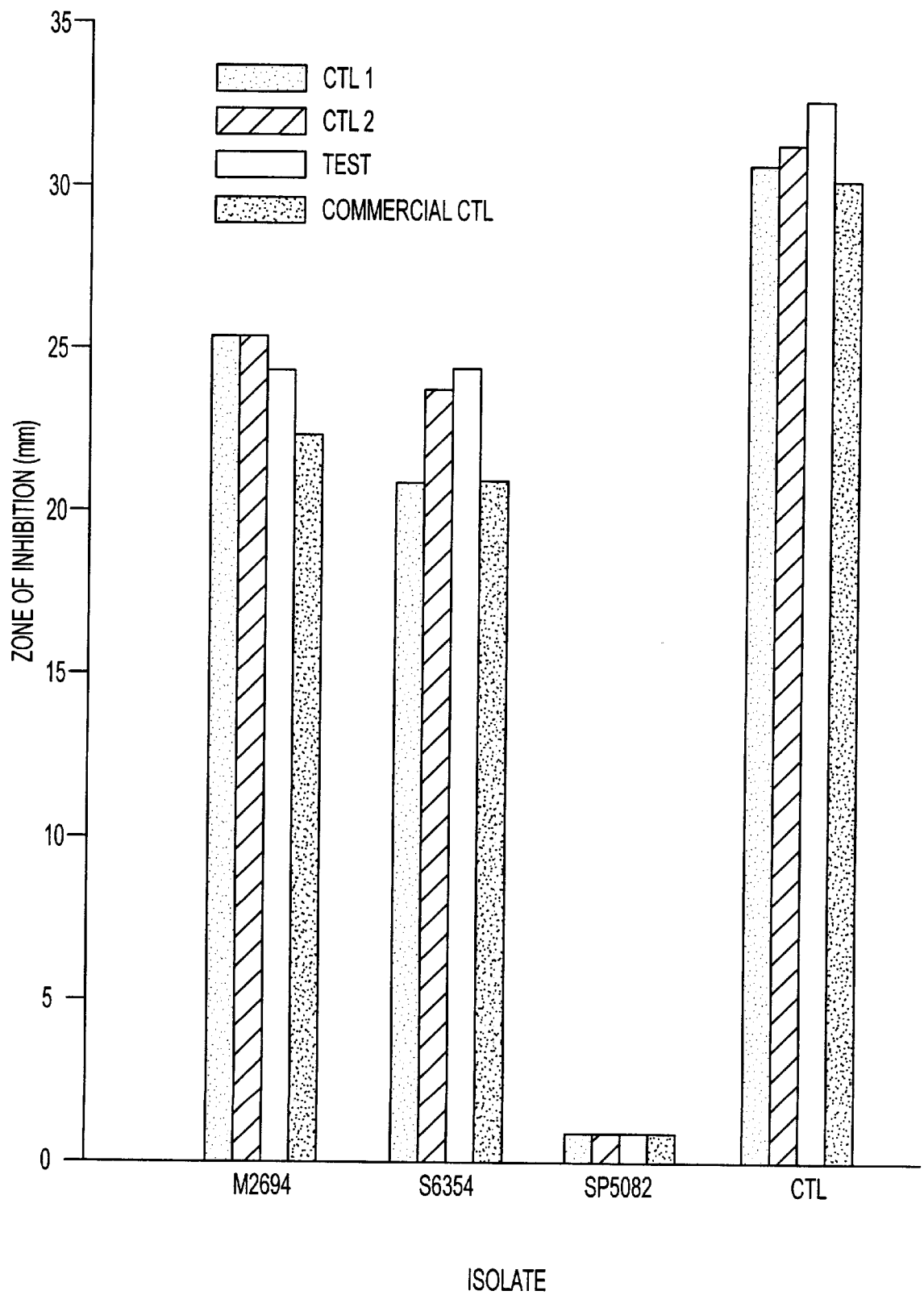
FIG. 35 shows the effect of control and test penicillin V on clinical isolates.

The effect of control and deuterated penicillin V on *S. aureus* clinical isolates was determined (FIGS. 34 and 35). In the case of methicillin sensitive isolates, the modified drug was always more potent than the controls. The modest differences may be related to the concentrations used and density of bacterial seeding on the plates.

Figure 36:
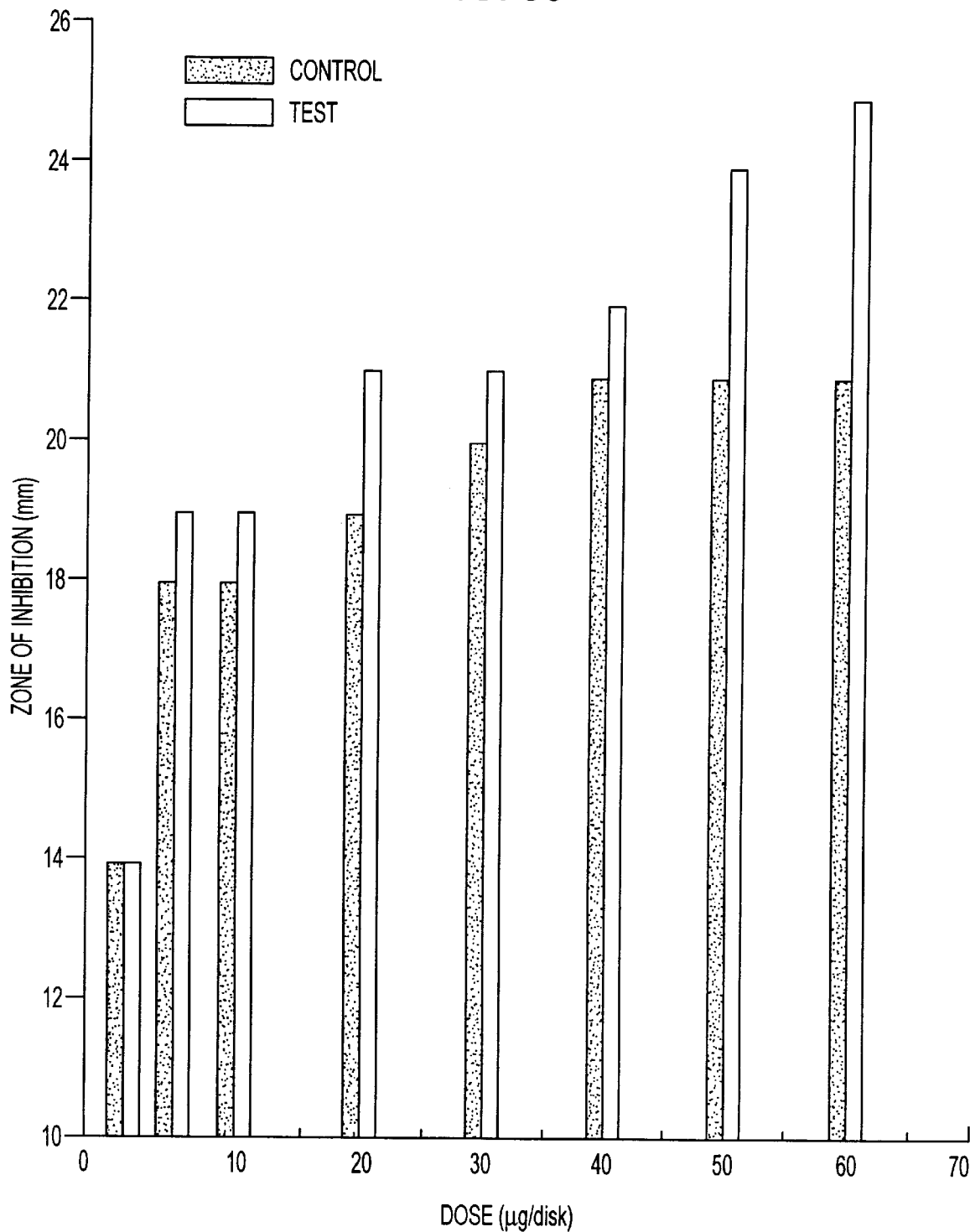
FIG. 36 shows the results of a control and test ceftazidime dose-response experiment.

A ceftazidime dose-response study was carried out using *Enterobacter aerogenes* as the test organism and differing doses of control and test ceftazidime as indicated (FIG. 36). These results show that at higher doses, the effectiveness of test ceftazidime relative to control is greater. This provides further evidence suggesting that modification of ceftazidime changes its spectrum of activity as well as potency.

A tube dilution study was carried out according to the previous protocols as a repeat of a previous study (FIG. 37). These results confirm the previous study suggesting that modified ceftazidime has either an enhanced spectrum of activity against *E. aerogenes* or is more potent.

These results indicate that the drug modification process which we used is specific. Both Penicillin V and ceftazidime have had their spectrum of activity altered. A new finding, however, is that the potency of the antibiotics is altered. In other words, the drugs can be effective against bacteria traditionally not sensitive to these drugs, both the doses needed to affect growth of traditionally sensitive bacteria can also be altered.

The following antibiotics are related to penicillin V and the same effect should occur with deuteration according to the above described procedure:
amoxicillin
ampicillin
bacampicillin
pivampicillin
pivmecillinam
carbenicillin
piperacillin
ticarcillin
penicillin G The following are pencilinnase resistant but we would predict increased potency and increased penicillin resistance after deuteration:
cloxacillin
fluceoxacillin
nafcillin
methicillin Additional compounds that can be deuterated according to the methods described here are the following:

Penicillin V, penicillin G, ricarcillin, cloxacillin, methicillin, piperacillin, cefaclor, cefmandole, cefazolin, cefotaxime, cefoxitin ceftazidime, gentamycin, tobramycin, amikacin, erythromycin, clindamycin, rifampin, minocycline, isoniazid, trimethoprin, sulfamethoxazole, ciprofloxacin, metronidazole, choloroquine, quinacrine, pyrimethamine, clotrimazole, ketoconazole, amphotericin, fluconazole, pentamidine, acyclovir, guancyclovir, didanosine, foscarnet, ganciclovir, amantadine, zalcitabine, zidovudine, asprin, acetominophen, ibuprofen, indomethacin, ketoprofen, sulindac, piroxicam, imuran, dexamethasone, prednisone, adriamycin, cisplatin, methotrexate, fluorouracil, cyclophosphamide, tamoxifen, L-dopa, benztropine, propranolol, sotalol, atenolol, acebutolol, isoproterenol, lidocaine, procainamide, quinidine, amiodarone, nifedipine, nicardipine, nitrendipine, diltiazem, verapamil, flunarizine, nitroglycerine, diisopyramide, furosemide, dobutamine, digoxin, ace inhibitors, β2 agonists, short-acting nitrates, diazepam, alprazolam, lorazepam, amitriptyline, fluvoxamine, sertraline, fluoxetine, phenytoin, valproic acid, haloperidol, chlorpromazine,captopril, hydrochlorthizide, prazosin, etidronate, misoprostil, omeprazole, ranitidine, cimetadine, dimenhydrinate, cisapride, Losec, metaclopramide, 5-aminosalicylate, glyburide, metformin, niacin, lovastatin, gemfibrazol, salbutamol, betamethasone, teophylline, cyclosporin.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solution can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with suitable amount of carrier so as to provide the form for proper administration to the host. While intravenous injection is a very effective form of administration, other modes can be employed.

Further variations and modifications of the foregoing will be apparent to those skilled in the art and such variations and modifications are intended to be encompassed by the claims that are appended hereto.

We claim:

1. A pharmaceutical composition comprising:

a dihydropyridine compound which is enriched with deuterium having the formula:

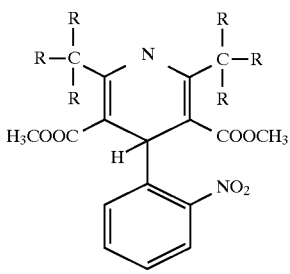

wherein R is either hydrogen or deuterium and at least one R is deuterium and a pharmaceutically acceptable carrier.

2. The pharmaceutical composition according to claim 1 wherein at least one of the methyl groups attached to position 2 and 6 of the dihydropyridine ring is substituted with $CD_3$.

3. The pharmaceutical composition according to claim 2, wherein said deuterated dihydropyridine is deuterated nifedipine having the formula

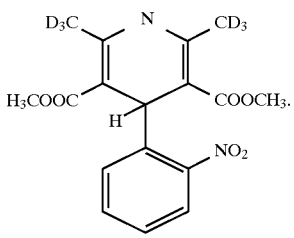

4. Deuterated nifedipine having the formula

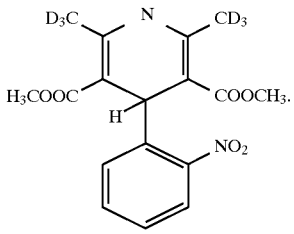

5. A method for making the deuterated nifedipine of claim 4, said method comprising:

dissolving nifedipine in a mixture of deuterochloroform and deuterium oxide to form a solution, adding trifluoroacetic anhydride and deuteroacetone to said solution, freezing and sealing said solution within a vessel, heating said solution at a temperature and for a period of time sufficient to deuterate all of the hydrogen atoms at the 2 and 6 position on said nifedipine, and recovering said deuterated nifedipine.

6. A pharmaceutical preparation comprising as the active component the deuterated nifedipine of claim 4 and a pharmaceutically acceptable carrier.

7. The method according to claim 5, said method comprising:

dissolving 80 mg of nifedipine in a mixture of about 2 ml of deuterochloroform and about 0.5 ml of deuterium oxide to form a solution, adding about 0.2 ml of trifluoracetic anhydride and 2 ml of deuteroacetone to said solution and mixing therewith, freezing and sealing said solution within a vessel, heating said solution at a temperature of about 50° to about 65° C. for a period of time of about 150 to 180 hours, cooling said heated solution and recovering said deutrated nifedipine.

8. A method for the treatment of hypertension in an animal suffering therefrom comprising:

administering to said animal a therapeutically effective amount of the pharmaceutical composition of claim 1.

9. A method for the prolongation of the duration of action of a drug comprising, administering to a patient in need thereof a pharmaceutical preparation as in claim 1, wherein the active ingredient thereof is a deuterated pharmacologically active compound.

10. A method for the treatment of hypertension in an animal suffering therefrom comprising:

administering to said animal a therapeutically effective amount of the pharmaceutical composition of claim 3.

* * * * *